United States Patent
Chuang

(10) Patent No.: US 10,870,684 B2
(45) Date of Patent: Dec. 22, 2020

(54) DISINTEGRIN VARIANTS AND PHARMACEUTICAL USES THEREOF

(71) Applicant: National Cheng Kung University, Tainan (TW)

(72) Inventor: Woei-Jer Chuang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 16/556,952

(22) Filed: Aug. 30, 2019

(65) Prior Publication Data

US 2020/0010516 A1    Jan. 9, 2020

Related U.S. Application Data

(62) Division of application No. 15/505,357, filed as application No. PCT/US2015/046322 on Aug. 21, 2015, now Pat. No. 10,508,137.

(60) Provisional application No. 62/040,503, filed on Aug. 22, 2014.

(51) Int. Cl.
| | |
|---|---|
| C07K 14/00 | (2006.01) |
| C07K 14/46 | (2006.01) |
| C12N 9/64 | (2006.01) |
| C07K 16/28 | (2006.01) |
| A61K 38/00 | (2006.01) |
| C12N 15/09 | (2006.01) |

(52) U.S. Cl.
CPC .......... *C07K 14/46* (2013.01); *C07K 16/2848* (2013.01); *C12N 9/6418* (2013.01); *A61K 38/00* (2013.01); *C07K 16/2839* (2013.01); *C07K 16/2842* (2013.01); *C07K 2318/20* (2013.01); *C12N 15/09* (2013.01)

(58) Field of Classification Search
None
See application file for complete search history.

(56) References Cited

U.S. PATENT DOCUMENTS

| 5,380,646 A | 1/1995 | Knight et al. |
|---|---|---|
| 7,220,724 B2 | 5/2007 | Markland, Jr. et al. |
| 10,508,137 B2* | 12/2019 | Chuang .................... A61P 9/10 |
| 2004/0171123 A1 | 9/2004 | Rosen et al. |
| 2007/0207952 A1 | 9/2007 | Silva et al. |
| 2008/0188413 A1 | 8/2008 | Chuang et al. |
| 2011/0152192 A1 | 6/2011 | Chuang et al. |
| 2011/0166072 A1 | 7/2011 | Chuang et al. |
| 2013/0225495 A1 | 8/2013 | Feng |
| 2016/0317610 A1 | 11/2016 | Markland, Jr. et al. |
| 2019/0194271 A1* | 6/2019 | Wu .......................... A61K 38/00 |
| 2020/0181214 A1* | 6/2020 | Wu .......................... A61K 38/00 |

FOREIGN PATENT DOCUMENTS

WO    2017001990 A1    1/2017

OTHER PUBLICATIONS

Int'l Search Report dated Jan. 20, 2016 in Int'l Application No. PCT/US2015/046322.
Written Opinion dated Jan. 20, 2016 in Int'l Application No. PCT/US2015/046322.
Int'l Preliminary Report on Patentability dated Feb. 28, 2017 in Int'l Application No. PCT/US2015/046322.
Sumathipala et al, "The "Linker" Region (Amino Acids 38-47) of the Disintegrin Elegantin is a Novel Inhibitory Domain of Integrin alpha 5beta1-Dependent Cell Adhesion of Fibronectin," Journal of Biological Chemistry, vol. 281, No. 49, pp. 37686-37696 (2006).
Lu et al. Preferential antagonism of the interactions of the integrin alpha IIb beta 3 with immobilized glycoprotein ligands by snake-venom RGD (Arg-Giy-Asp) proteins. Biochem J. Dec. 15, 1994; 304(Pt 3): 929-936. (Year: 1994).
Kini et al. Scientific and Standardization Committee Communications: Inventory of Exogenous Inhibitors of Platelet Aggregation From Animal Sources. Posted on ISTH Website Oct. 11, 2000, pp. 1-29 (Year 2000).
Huang TF., What have snakes taught us about integrins? CML, Cell. Mol., Life Sci. 54 (1998) 527-540. (Year: 1998).
Shiu et al. Effect of P to A Mutation of the N-Terminal Residue Adjacent to the Rgd Motif on Rhodostomin: Importance of Dynamics in Integrin Recognition. PLoS ONE 7(1): e28833. 2012 (Year 2012).
Q92119-1 (Nov. 1, 1996), Atrolysin e—Protobothrops mucrosquamatus (Taiwan habu). pp. 1-5 (Year: 1996).
Koivunen et al. Identification of Receptor Ligands with Phage Display Peptide Libraries(J Nucl Med; 40:883-888, 1999). (Year 1999).
Koivunen E, Wang B, Ruoslahti E. Phage libraries displaying cyclic peptides with different ring sizes: ligand specificities of the RGD-directed integrins. Bio/Technology. 1995:13:265-270. (Year 1995).

* cited by examiner

*Primary Examiner* — Maher M Haddad
(74) *Attorney, Agent, or Firm* — Ice Miller LLP

(57) ABSTRACT

Disintegrin variants that bind specifically to one or more of α5β1 and αv integrins, such as αvβ1, αvβ3, αvβ5, αvβ6 and αvβ8, but with reduced binding activity to αIIbβ3, are described. Also described are uses of the disintegrin variants for the treatment or prevention of a disease associated with an αv integrin or an α5β1 integrin.

8 Claims, 13 Drawing Sheets

Specification includes a Sequence Listing.

US 10,870,684 B2

DISINTEGRIN VARIANTS AND PHARMACEUTICAL USES THEREOF

CROSS-REFERENCE TO RELATED APPLICATIONS

This application is divisional of U.S. patent application Ser. No. 15/505,357, filed Feb. 21, 2017, which is a Section 371 of International Application No. PCT/US2015/046322, filed Aug. 21, 2015, which was published in the English language on Feb. 25, 2016, under International Publication No. WO 2016/029131 A1, which claims priority under 35 U.S.C. § 119(e) to U.S. Provisional Patent Application No. 62/040,503, filed Aug. 22, 2014, and the disclosures of which are herein incorporated by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing_688947-1U1.txt", creation date of Jul. 8, 2019, and having a size of 161.8 KB. The sequence listing submitted via EFS-Web is part of the specification and is herein incorporated by reference in its entirety.

FIELD OF THE INVENTION

The invention relates to disintegrin variants that bind specifically to one or more of α5β1 and αv integrins, such as αvβ1, αvβ3, αvβ5, αvβ6 and αvβ8, but with reduced binding activity to αIIbβ3, and uses of the disintegrin variants for the treatment and prevention of a disease associated with an αv integrin or α5β1 integrin.

BACKGROUND OF THE INVENTION

Integrins are transmembrane receptors that bind extracellular matrix proteins or other adhesion receptors on neighboring cells. Heterodimeric pairing of integrin α and β subunits confers specificity of binding to one or more substrates (Weis et al., 2011, *Cold Spring Harb Perspect Med;* 1:a006478). This family of adhesion molecules plays a pivotal role in broad contexts of biology, including inflammation, innate and antigen specific immunity, homeostasis, wound healing, tissue morphogenesis, and regulation of cell growth and differentiation. Dysregulation of integrins is involved in the pathogenesis of many disease states, from autoimmunity to thrombotic vascular diseases to cancer metastasis. Extensive efforts have been directed towards the discovery and development of integrin antagonists for clinical applications.

The αv integrins, each having an αv subunit paired with a β1, β3, β5, β6 or β8 subunit, appear to be particularly important during the tissue remodeling associated with wound repair, angiogenesis, and cancer (Weis et al., 2011, supra). The αv integrins are being targeted for cancer, ophthalmological and orthopedic indications. Integrins αvβ3 and αvβ5 have also been associated with tumors, arthritis, psoriasis and age-related macular degeneration (AMD). In particular, αvβ3 integrin is important in mediating angiogenesis and in inhibiting tumor migration, and αvβ6 integrin is upregulated in some cancers. The other αv integrins present in the cornea (αvβ5, αvβ6, and αvβ8) mediate transforming growth factor β (TGFβ) activation.

It was reported that the integrins α5β1, αvβ3 and αvβ5 play an important role in the process of angiogenesis and are expressed in a variety of malignancies, including, but not limited to, melanoma, breast cancer, prostate cancer, colon cancer, and gliomas (Staunton et al., 2006, *Adv Immunol.,* 91:111-57). The intratumoral expression of these integrins has been associated with progression and metastasis in tumors, such as melanoma, breast cancer, and prostate cancer (Staunton et al., 2006, supra). They have been shown to signal through multiple pathways and contribute to endothelial cell migration and proliferation. In vivo, they are overexpressed on tumor neovasculature and on tumor cells themselves, which suggests that their function may potentiate tumor progression by multiple mechanisms. Antagonistic antibodies and small molecules directed against integrins α5β1, αvβ3, and αvβ5 have been shown to inhibit angiogenesis in vitro and in vivo. Inhibitors of integrins α5β1, αvβ3, and αvβ5 are able to inhibit signaling through ERK, Akt and FAK, resulting in decreased adhesion, migration and proliferation of endothelial and cancer cells. These antagonists have also been found to elicit cell death through caspase-dependent mechanisms. Therefore, the critical role of integrins α5β1, αvβ3 and αvβ5 in angiogenesis and association with tumor progression make them attractive targets for anticancer therapy, and many antagonists of these integrins have been tested in clinical trials.

The αvβ3 integrin shares the same β3 subunit with the αIIbβ3 integrin, as well as several macromolecular ligands including fibrinogen, fibronectin, thrombospondin, von Willebrand factor, and vitronectin. These ligands all contain a triple amino acid sequence arginine-glycine-aspartic acid (RGD). Fibronectin and vitronectin are also ligands for α5β1 and other αv integrins. The αIIbβ3 integrin is a major membrane protein on platelets and plays an important role in platelet aggregation. Several αIIbβ3 integrin antagonists have been developed for the treatment of patients with acute coronary syndrome (ACS). However, because extensive inhibition of platelet aggregation are associated with increased risk of bleeding, ongoing studies are focused on reduction of bleeding and other side effects of αIIbβ3 integrin antagonists. It is essential to design drugs by blocking either a single integrin or multiple αv integrins for different indications (Goodman, 2012. *Trends Pharmacol Sci.* 2012; 33:405-412).

Disintegrins are a family of low-molecular-weight RGD-containing peptides that bind to integrins, such as, αIIbβ3, α5β1, and αvβ3 expressed on platelets and other cells, including vascular endothelial cells and some tumor cells. In addition to their potent anti-platelet activity, studies of disintegrins have revealed new uses in the diagnosis of cardiovascular diseases and the design of therapeutic agents in arterial thrombosis, osteoporosis, and angiogenesis-related tumor growth and metastasis. Rhodostomin (Rho), a disintegrin from the venom of *Colloselasma rhodostoma,* has been found to inhibit platelet aggregation in vitro and in vivo through the blockade of platelet glycoprotein αIIbβ3. It is also found that Rho can bind to integrins αIIbβ3, α5β1, and αvβ3 with high affinity and interact with cancer cells. For example, Rho is reported to inhibit the adhesion of breast and prostate carcinoma cells to both unmineralized and mineralized bone extracellular matrices in a dose-dependent manner, without affecting the viability of tumor cells. Rho also inhibits the migration and invasion of breast and prostate carcinoma cells.

However, because rhodostomin non-specifically binds to integrins αIIbβ3, α5β1, and αvβ3, the pharmaceutical uses of rhodostomin may cause serious side effects, such as bleeding resulting from the inhibition of platelet aggregation. Therefore, a need exists in the art for a disintegrin variant that is selective for integrins α5β1 and αvβ3, but with reduced binding activity to αIIbβ3. Such a need is met by this invention.

SUMMARY OF THE INVENTION

The invention relates to disintegrin variants having one or more mutations in one or more of the linker region, the RGD loop and the C-terminus of a disintegrin, such as rhodostomin, that have reduced binding activity to αIIbβ3 integrin, thus a weak inhibition on the platelet aggregation, but bind specifically to one or more of α5β1 and αv integrins, such as αvβ1, αvβ3, αvβ5, αvβ6 and αvβ8.

Accordingly, in one general aspect, the invention relates to a disintegrin variant, comprising at least one selected from the group consisting of:
  (a) a mutant linker comprising at least one mutation at positions 1 to 5 of the amino acid sequence of SEQ ID NO:332 (SRAGKIC);
  (b) a mutant RGD loop comprising the amino acid sequence selected from the group consisting of SEQ ID NOs: 329 to 331; and
  (c) a mutant C-terminus comprising at least one mutation at positions 1-4 of the amino acid sequence of SEQ ID NO: 334 (PRYH),
wherein the disintegrin variant has reduced binding activity to αIIbβ3 integrin as compared to a disintegrin not having the at least one selected from the group consisting of the mutant linker, the mutant RGD loop and the mutant C-terminus. Preferably, the disintegrin variant also has increased binding activity to at least one of αvβ1, αvβ3, αvβ5, αvβ6, αvβ8 and α5β1 integrins as compared to a disintegrin not having the at least one selected from the group consisting of the mutant linker, the mutant RGD loop and the mutant C-terminus.

According to embodiments of the invention, the disintegrin variant can be a variant of any disintegrin, including, but not limited to a disintegrin selected from the group consisting of rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin. Preferably, the disintegrin variant is a variant of a disintegrin having the amino acid sequence selected from the group consisting of SEQ ID NOs: 1 to 6. More preferably, the disintegrin variant is a variant of rhodostomin having the amino acid sequence of SEQ ID NO: 1.

In a preferred embodiment, the disintegrin variant comprises a mutant RGD loop comprising at least one mutation at positions 1-3, 5, 7 and 8 of the amino acid sequence of SEQ ID NO: 333 (RIPRGDMP) and at least one of the mutant linker and the mutant C-terminus described herein.

In another preferred embodiment of the invention, the disintegrin variant comprises a mutant linker having the amino acid sequence selected from the group consisting of SEQ ID NO:306 to SEQ ID NO: 318.

In yet another preferred embodiment of the invention, the disintegrin variant comprises a mutant C-terminus having the amino acid sequence selected from the group consisting of SEQ ID NO: 319 to SEQ ID NO:328.

In a preferred embodiment of the invention, the disintegrin variant comprises a mutant RGD loop having the amino acid sequence selected from the group consisting of SEQ ID NO: 329 to SEQ ID NO: 331, and at least one of a mutant linker having the amino acid sequence selected from the group consisting of SEQ ID NO:306 to SEQ ID NO: 318, and a mutant C-terminus having the amino acid sequence selected from the group consisting of SEQ ID NO:319 to SEQ ID NO: 328. More preferably, the disintegrin variant comprises the mutant RGD loop, the mutant linker and the mutant C-terminus described herein.

According to embodiments of the invention, the disintegrin variant comprises the amino acid sequence selected from the group consisting of SEQ ID NO: 7 to SEQ ID NO:179. Preferably, the disintegrin variant according to an embodiment of the invention comprises the amino acid sequence selected from the group consisting of SEQ ID NOs: 123, 124, 147, 149 and 171.

Preferably, the disintegrin variant according to an embodiment of the invention is modified, e.g., for improved delivery or stability. For example, the disintegrin variant is pegylated or is conjugated with a fusion partner, such as an albumin or Fc.

Another general aspect of the invention relates to a polynucleotide encoding a disintegrin variant of the invention, which can be an expression vector comprising a regulatory sequence, such as a promoter, operably linked to a DNA sequence encoding the disintegrin variant.

The invention also relates to a recombinant host cell comprising a polynucleotide encoding a disintegrin variant of the invention. The host cell can be a prokaryotic cell, a yeast cell, an insect cell or a mammalian cell.

The invention further relates to a process of making a disintegrin variant of the invention, comprising producing the disintegrin variant from a recombinant host cell according to an embodiment of the invention.

Also provided is a pharmaceutical composition comprising a disintegrin variant of the invention and a pharmaceutically acceptable carrier.

Yet another general aspect of the invention relates to a method for treating a disease associated with at least one of αvβ1, αvβ3, αvβ5, αvβ6, αvβ8 and α5β1 integrins, preferably a disease associated with at least one of integrins α5β1 and αvβ3, in a subject in need thereof. The method comprises administering to the subject a pharmaceutical composition of the invention.

In one embodiment of the invention, the integrin-associated disease is an angiogenesis-related eye disease selected from the group consisting of age-related macular degeneration, diabetic retinopathy, corneal neovascularizing diseases, ischaemia-induced neovascularizing retinopathy, high myopia, and retinopathy of prematurity.

In another embodiment of the invention, the integrin-associated disease is a cancer selected from the group consisting of metastatic melanoma, metastatic prostate cancer, metastatic breast cancer, colorectal carcinoma, liver cancer, ovarian cancer, cervical cancer, pancreatic cancer, non-small-cell lung cancer, and glioblastoma multiforme.

Another general aspect of the invention relates to use of a disintegrin variant of the invention in the manufacture of a medicament for the treatment of a disease associated with at least one of αvβ1, αvβ3, αvβ5, αvβ6, αvβ8 and α5β1 integrins in a subject in need thereof.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 1A is an illustration of the interactions among the linker region, RGD loop, and C-terminal region of rhodostomin; and FIG. 1B shows the amino acid sequences of the regions involved in the interactions between rhodostomin and integrins, where the residues that can be mutated in a disintegrin variant according to an embodiment of the invention are marked as "X";

FIG. 2A is the wild-type Rho, FIG. 2B is AR-NP protein (KKART-ARGRGDNP, SEQ ID NO: 350), a disintegrin variant according to an embodiment of the invention, and FIG. 2C is phosphate buffered saline (PBS);

DETAILED DESCRIPTION OF THE INVENTION

Figure 1A:
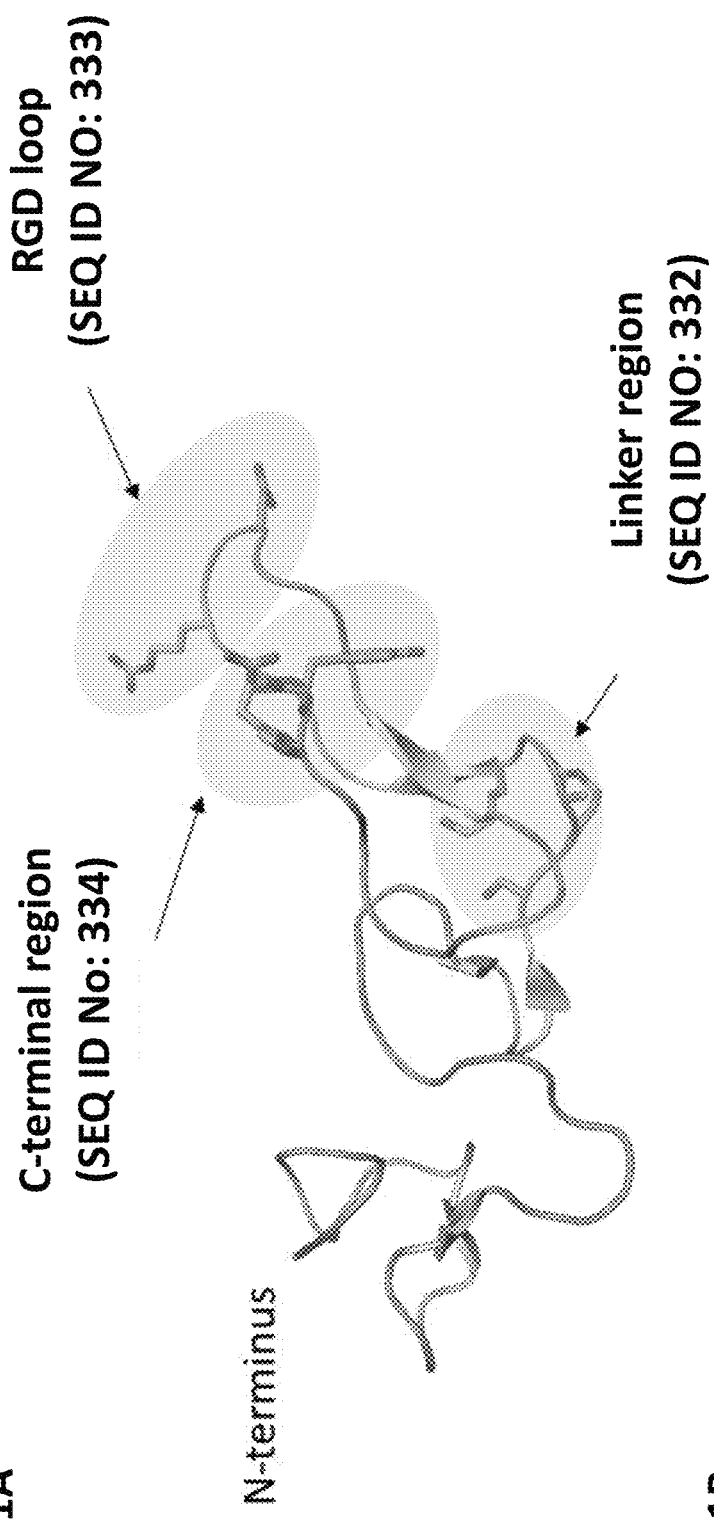
FIGS. 1A and 1B illustrate the interaction map of rhodostomin.
Figure 1B:
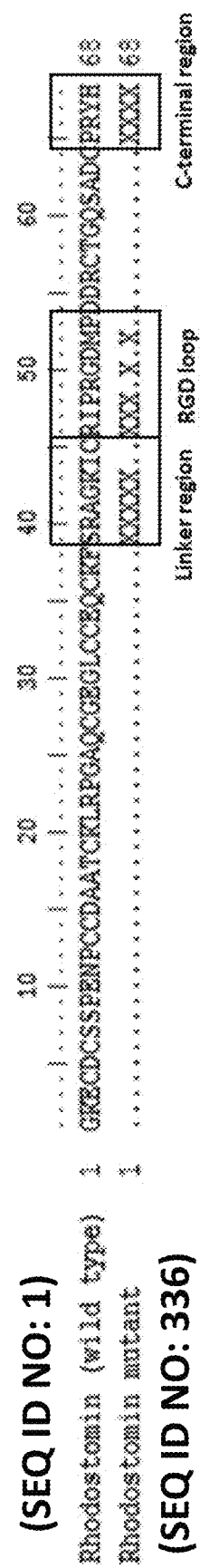

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, a "disintegrin" refers to a class of cysteine-rich proteins that are potent soluble ligands of integrins and are involved in regulating many processes such as cell-cell and cell-extracellular matrix adhesion, migration and invasion, cell cycle progression, differentiation and cell type speciation during development of many metazoan organisms, cell death and apoptosis. The amino acid motif RGD (Arg-Gly-Asp) is conserved in most monomeric disintegrins and is located at the tip of a flexible loop, the integrin-binding loop, which is stabilized by disulfide bonds and protruding from the main body of the polypeptide chain. All disintegrins purified from snake venom selectively bind to or target the fibrinogen receptors, such as αv-integrins, α5β1 integrin, and integrin αIIbβ3, the binding of which results in the inhibition of fibrinogen-dependent platelet aggregation as well as other biological activities mediated by these fibrinogen receptors. Examples of disintegrins useful in the invention include, but are not limited to, rhodostomin, triflavin, rchistatin trimucrin, elegantin, trigramin and applaggin. Exemplary peptide sequences of disintegrins useful in the invention are provided in SEQ ID NOs: 1 to 6.

As used herein, a "disintegrin variant" refers to an engineered, functionally active protein, or a polypeptide or any derivatives thereof, that comprises an amino acid sequence derived or modified or mutated from a wild-type disintegrin. A disintegrin variant contains one or more mutations compared to a naturally occurring disintegrin. The one or more mutations can be a substitution, deletion, or insertion of one or more amino acids to the naturally occurring disintegrin. In one embodiment, a disintegrin variant has a reduced binding activity to αIIbβ3 integrin as compared to the naturally occurring disintegrin not having the one or more mutations. More preferably, a disintegrin variant binds specifically to one or more of integrins αvβ1, αvβ3, αvβ5, αvβ6 and αvβ8, and integrin α5β1. Most preferably, the disintegrin variant has increased binding activity to one or both of integrin αvβ3 and integrin α5β1 as compared to the naturally occurring disintegrin without the one or more mutations.

In certain embodiments, a disintegrin variant comprises a modified Rho protein from venom that contains at least one amino acid substitution, insertion or deletion compared with the naturally occurring Rho. Modified Rho variants and/or different disintegrin can further comprise post translational modifications.

In one embodiment, a disintegrin variant of the invention comprises a mutant RGD loop. As used herein, a "mutant RGD loop" or "mutant RGD region" refers to a peptide comprising one or more mutations in the amino acid sequence that spans the RGD loop of a disintegrin. The RGD loop of a wild-type disintegrin comprises the RGD residues that bind to integrins. For example, the RGD loop of Rho comprises the amino acid sequence of SEQ ID NO: 333 (RIPRGDMP). In preferred embodiments of the invention, a mutant RGD loop comprises at least one mutation at positions 1-3, 5, 7 and 8 of the amino acid sequence of SEQ ID NO: 333. More preferably, a mutant RGD loop comprises the amino acid sequence selected from the group consisting of SEQ ID NOs: 329 to 331.

In another embodiment, a disintegrin variant of the invention comprises a mutant linker. As used herein, a "mutant linker" or "mutant linker region" refers to a peptide comprising one or more mutations in the amino acid sequence that spans the linker region of a disintegrin. The linker region of a disintegrin is located immediately N-terminal to the RGD loop. For example, the linker region of Rho comprises the amino acid sequence of SEQ ID NO:332 (SRAGKIC). In preferred embodiments of the invention, a mutant linker comprises at least one mutation at positions 1 to 5 of the amino acid sequence of SEQ ID NO:332. More preferably, a mutant linker comprises the amino acid sequence selected from the group consisting of SEQ ID NO:306 to SEQ ID NO: 318.

In yet another embodiment, a disintegrin variant of the invention comprises a mutant C-terminus. As used herein, a "mutant C-terminus" or "mutant C-terminal region" refers to a peptide comprising one or more mutations in the amino acid sequence of the C-terminal region of a disintegrin. The C-terminal region of a disintegrin is located at the carboxyl end of the disintegrin. For example, the C-terminus of Rho comprises the amino acid sequence of SEQ ID NO: 334 (PRYH). In preferred embodiments of the invention, a mutant C-terminus comprises at least one mutation at positions 1-4 of the amino acid sequence of SEQ ID NO:334. More preferably, a mutant C-terminus comprises the amino acid sequence selected from the group consisting of SEQ ID NO:319 to SEQ ID NO: 328.

In preferred embodiments, a disintegrin variant of the invention comprises a mutant RGD loop and at least one of a mutant linker and a mutant C-terminus of a disintegrin.

In more preferred embodiments, a disintegrin variant of the invention comprises a mutant RGD loop, a mutant linker and a mutant C-terminus of a disintegrin described herein.

A disintegrin variant of invention can include naturally-occurring and non-naturally occurring amino acids. Examples of naturally-occurring amino acid include, but are not limited to, any of the twenty primary, naturally occurring amino acids which typically form peptides, polypeptides, and proteins. The following table 1 is a tabulation of 20 naturally occurring amino acids.

TABLE 1

Naturally Occurring Amino Acids

| Amino Acid | Three-letter abbreviation | One-letter symbol |
|---|---|---|
| Alanine | Ala | A |
| Arginine | Arg | R |

TABLE 1-continued

Naturally Occurring Amino Acids

| Amino Acid | Three-letter abbreviation | One-letter symbol |
|---|---|---|
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Non-naturally occurring amino acids are non-proteinogenic amino acids that either occur naturally or are chemically synthesized. Examples of non-naturally occurring amino acids include, but are not limited to, β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, N-methyl amino acids, etc.

As used herein, "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution: Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched); Group II: glutamic acid, aspartic acid and non-naturally occurring amino acids with carboxylic acid substituted C1-C4 aliphatic side chains (unbranched or one branch point); Group III: lysine, ornithine, arginine and non-naturally occurring amino acids with amine or guanidino substituted C1-C4 aliphatic side chains (unbranched or one branch point); Group IV: glutamine, asparagine and non-naturally occurring amino acids with amide substituted C1-C4 aliphatic side chains (unbranched or one branch point); and Group V: phenylalanine, phenylglycine, tyrosine and tryptophan.

As used herein, "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in their side chains. Examples of highly conservative substitutions include valine for leucine, threonine for serine, aspartic acid for glutamic acid and phenylglycine for phenylalanine.

The term "isolated protein" or "isolated polypeptide" as used herein refers to a protein encoded by a nucleic acid including, inter alia, genomic DNA, cDNA, recombinant DNA, recombinant RNA, or nucleic acid of synthetic origin or some combination thereof, which (1) is free of at least some proteins with which it would normally be found, (2) is essentially free of other proteins from the same source, e.g., from the same cell or species, (3) is expressed by a cell from a different species, (4) has been separated from at least about 50 percent of polynucleotides, lipids, carbohydrates, or other materials with which it is naturally found when isolated from the source cell, (5) is not linked (by covalent or noncovalent interaction) to all or a portion of a polypeptide to which the "isolated protein" is linked in nature, (6) is operatively linked (by covalent or noncovalent interaction) to a polypeptide with which it is not linked in nature, or (7) does not occur in nature. Preferably, the isolated protein is substantially free from other contaminating proteins or polypeptides or other contaminants that are found in its natural environment that would interfere with its therapeutic, diagnostic, prophylactic or research use.

As used herein, the terms "polynucleotide," "nucleotide," "oligonucleotide," and "nucleic acid" may be used interchangeably to refer to nucleic acid comprising DNA, RNA, derivative thereof, or combination thereof.

As used herein, the terms "polypeptide" and "protein" may be used interchangeably to refer to proteins produced by naturally-occurring and non-recombinant cells, by genetically-engineered or recombinant cells, or by chemical synthesis, and comprise molecules having the amino acid sequence of the native protein, or sequences that have deletions, additions, and/or substitutions of one or more amino acids of the native sequence. In accordance with the instant invention, the disintegrins are polypeptide or protein specifically encompasses modified Rho protein or fragments thereof or variants thereof. In certain particular embodiments, the disintegrins encompasses Rho protein, the fragments or variants thereof that inhibit integrin activity. In certain embodiments, the disintegrin targets αv-integrin isoform, such as any group selected from the αvβ1, αvβ3, αvβ5, αvβ6 and αvβ8, and integrin α5β1. In certain other particular embodiments, the integrin is not αIIbβ3.

As used herein, a "host cell" is an individual cell or cell culture which can be or has been a recipient of any recombinant vector(s) or polynucleotide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vitro or in vivo with a recombinant vector or a polynucleotide of the invention. A host cell which comprises a recombinant vector of the invention may be called a "recombinant host cell." Suitable host cells include prokaryotic or eukaryotic cells, including, for example, bacterial, yeast, fungal, plant, insect, and mammalian cells.

As used herein, the term "binding activity" refers to the binding of a disintegrin or a disintegrin variant to an integrin that results in one or more of inhibiting, blocking, neutralizing, reducing, abrogating or interfering with the integrin activities. In certain embodiments, the disintegrin or disintegrin variant inhibits integrin activities by binding to integrin and sequestering integrin from binding to other molecules, for example other ECM proteins. In certain other embodiments, the disintegrin or disintegrin variant inhibits integrin activities by binding to integrin and preventing integrin from triggering downstream signaling events in the cells.

As used herein, the term "inhibition" or "inhibit" in the context of integrin activity as used herein refers to a property of a disintegrin or disintegrin variant that reduces the activity of integrin as analyzed by various functional assays, including without limitation, binding assays, migration assays, apoptosis assays and cell adhesion assays. In certain embodiments of the invention, the integrin is an αv-integrin isoform, including αvβ1, αvβ3, αvβ5, αvβ6 and αvβ8. In certain other particular embodiments, the integrin is α5β1. In certain further embodiments, the disintegrin or disintegrin variant inhibits integrin activity by from about 0% to about 100% as compared to the control in the absence of the disintegrin or disintegrin variant.

As used herein, the term "selectively bind", "selectively inhibit," "selective binding," "selective inhibition," "differentially bind," "differentially inhibit," "differential binding," or "differential inhibition" refers to the property of disintegrin or disintegrin variant that shows differential specificity for a particular target integrin molecule over one or more other integrins. For example, a disintegrin variant of the invention selectively binds to one or more of integrins αvβ1, αvβ3, αvβ5, αvβ6, α5β1, thus has higher affinity to the one or more of integrins αvβ1, αvβ3, αvβ5, αvβ6, α5β1 than another integrin, such as αIIbβ3 integrin. In certain embodiments, the disintegrin variant comprising a modified Rho fragment selectively inhibits the activity of one or more integrins selected from the group consisting of integrins αvβ1, αvβ3, αvβ5, αvβ6 and integrin α5β1. In preferred embodiments, the disintegrin variant comprising a modified Rho fragment specifically inhibits both integrin αvβ3 and integrin α5β1, inhibits both integrin αvβ5 and integrin α5β1, or both integrin αvβ6 and integrin α5β1 activities. In certain alternative embodiments, the disintegrin variant comprising a modified Rho fragment specifically inhibits all of integrins αvβ1, αvβ3, αvβ5, αvβ6, and integrin α5β1 activities.

The term "homology" or "homologous" as used herein refers to the level of overall sequence similarity and/or identity between corresponding disintegrin fragments, such as a Rho fragment. High sequence homology suggests conservation of protein activity. A number of publicly available algorithms or software programs can be used to determine sequence homology. It is within the ability of one skilled in the art to determine the suitability of additional conservative or non-conservative amino acid substitutions and the level of sequence homology.

As used herein, a "subject" refers to any animal including, but not limited to humans and other primates, rodents (e.g., mice, rats, and guinea pigs), lagamorphs (e.g., rabbits), bovines (e.g., cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, lagamorphs, rodents, birds, etc. It is not intended that the term be limited to a particular age or sex. Thus, adult and newborn subjects, as well as fetuses, whether male or female, are encompassed by the term. Subjects "in need of treatment" are subjects with diseases and/or conditions that can be treated by inhibiting one or more activities of an integrin to achieve a beneficial therapeutic and/or prophylactic result. A beneficial outcome includes a decrease in the severity of symptoms or delay in the onset of symptoms, increased longevity and/or more rapid or more complete resolution of the disease or condition.

A "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

As used herein, "pharmaceutically acceptable salts" refer to derivatives of compounds wherein the parent compound is modified by making acid or base salts thereof.

As used herein, a "disease related to an integrin" refers to any condition, disorder, or syndrome related to the integrin that requires medical intervention or for which medical intervention is desirable. Such medical intervention can include treatment, diagnosis, and/or prevention.

As used herein, "effective amount" or "sufficient amount" refers to an amount of a disintegrin variant as described herein that can be therapeutically effective to inhibit, prevent, or treat a symptom of a particular disease, disorder, condition, or side effect.

The term "treat," "treatment" or "treating" means reducing the frequency, extent, severity and/or duration with a symptom of a particular disease, disorder, condition, or side effect.

The term "prevent," "prevention" or "preventing" means inhibition or the averting of symptoms of a particular disease, disorder, condition, or side effect.

Disintegrin Variants

It is discovered in the invention that variants of disintegrins from snake venom, such as rhodostomin (Rho) from *rhodostoma,* exhibit different capabilities to selectively bind to one or more αv-integrins, such as one or more of αvβ1, αvβ3, αvβ5, αvβ6 and αvβ8, and other integrins, such as α5β1, with reduced binding activity to αvIIbβ3. The capability of selectively binding to certain integrin(s) was enabled by mutating amino acid sequences in one or more of the linker region, the RGD loop and the C-terminus of a disintegrin of interest.

Accordingly, one general aspect of the invention relates to disintegrin variants. According to one embodiment of the invention, a disintegrin variant has reduced binding activity to αIIbβ3, and binds specifically to at least one of α5β1, αvβ1, αvβ3, αvβ5, αvβ6 and αvβ8.

Preferably, a disintegrin variant has reduced binding activity to αIIbβ3, but increased binding activity to at least one of α5β1 and αvβ3 as compared to the wild-type disintegrin from which the disintegrin variant derived.

For example, it was found that a Rho mutation in the RGD loop can increase specificity for αVβ3 and/or α5β1 integrin, a mutation in the C-terminal region can cause less binding to αIIbβ3 (thus weaker inhibition on platelet aggregation and less bleeding side effect) and a mutation in the linker region can also reduce binding to αIIbβ3, wherein each of the three regions are identified by the amino acid residue numbers in the wild-type Rho, and the amino acid residues that can be modified, e.g., by an insertion, deletion, or substitution, according to embodiments of the invention are each independently marked as "X."

According to embodiments of the invention, a disintegrin variant comprises a mutation in the RGD loop, i.e., a mutant RGD loop.

In one embodiment, a disintegrin variant comprises a mutant RGD loop having a consensus sequence of $^{49}RXD^{51}$. Examples of such variants include, but are not limited to, those having the amino acid sequences selected from the group consisting of SEQ ID NOs: 7-24.

In another embodiment, a disintegrin variant comprises a mutant RGD loop having a consensus sequence of $^{48}XRGD^{51}$ (SEQ ID NO: 341). Examples of such variants include, but are not limited to, those having the amino acid sequences selected from the group consisting of SEQ ID NOs: 25-42.

In another embodiment, a disintegrin variant comprises a mutant RGD loop having a consensus sequence of $^{48}XRGDXP^{53}$ (SEQ ID NO: 342). Examples of such variants include, but are not limited to, those having the amino acid sequences selected from the group consisting of SEQ ID NOs: 44-61.

In another embodiment, a disintegrin variant comprises a mutant RGD loop having a consensus sequence of $^{48}XRGDMX^{53}$ (SEQ ID NO: 343). Examples of such variants include, but are not limited to, those having the amino acid sequences selected from the group consisting of SEQ ID NOs: 63-78.

In another embodiment, a disintegrin variant comprises a mutant RGD loop having a consensus sequence of $^{46}XXPRGD^{51}$ (SEQ ID NO: 344). Examples of such variants include, but are not limited to, those having the amino acid sequences selected from the group consisting of SEQ ID NOs: 79-94.

In another embodiment, a disintegrin variant comprises a mutant RGD loop having a consensus sequence of $^{48}XRXDXP^{53}$ (SEQ ID NO: 345). Examples of such variants include, but are not limited to, those having the amino acid sequences selected from the group consisting of SEQ ID NOs: 95-101.

According to other embodiments of the invention, a disintegrin variant comprises a mutation in the C-terminal region, i.e., a mutant C-terminus.

In one embodiment, a disintegrin variant comprises a mutant C-terminus having a consensus sequence of $^{65}PRXXXXX^{71}$ (SEQ ID NO: 346). Examples of such variants include, but are not limited to, those having the amino acid sequences selected from the group consisting of SEQ ID NOs: 102-107.

In another embodiment, a disintegrin variant comprises a mutant C-terminus having a consensus sequence of $^{65}PRXXXXX^{71}$ (SEQ ID NO: 346), and further comprises a mutant RGD loop, such as those described herein. For example, the mutant RGD loop can have a consensus sequence of $^{48}ARGDMP^{53}$ (SEQ ID NO: 335). Examples of such variants include, but are not limited to, those having the amino acid sequences selected from the group consisting of SEQ ID NOs: 115-119.

According to yet other embodiments of the invention, a disintegrin variant comprises a mutation in the linker region, i.e., a mutant linker.

In one embodiment, a disintegrin variant comprises a mutant linker having a consensus sequence of $^{39}KKKR-TIC^{47}$ (SEQ ID NO: 306). Preferably, the disintegrin variant further comprises a mutant RGD loop such as those described herein. For example, the mutant RGD loop can have a consensus sequence of $^{48}XRXDXP^{53}$ (SEQ ID NO: 345). Examples of such variants include, but are not limited to, those having the amino acid sequences selected from the group consisting of SEQ ID NOs: 108-114.

According to further embodiments of the invention, a disintegrin variant comprises a mutation in the linker region, a mutation in the RGD loop and a mutation in the C-terminal region. Examples of such variants include, but are not limited to, those having the amino acid sequences selected from the group consisting of SEQ ID NOs:120-179.

A disintegrin variant of the invention can be made by any method suitable to the aims of the invention in view of the present disclosure. For example, a disintegrin variant can be constructed by a site-directed mutagenesis method. The disintegrin variant of the invention can be expressed using methods known in the art in view of the present disclosure. Cell-based methods and cell-free methods are suitable for producing peptides of the invention. Cell-based methods generally involve introducing a nucleic acid construct into a host cell in vitro and culturing the host cell under conditions suitable for expression, then harvesting the peptide, either from the culture medium or from the host cell, (for example, by disrupting the host cell), or both. The invention also provides methods of producing a disintegrin variant using cell-free in vitro transcription/translation methods, which are well known in the art.

The disintegrin variant can be encoded by a modified disintegrin nucleotide sequence that encodes a modified amino acid sequence resulting in said polypeptide having substantially reduced integrin αIIbβ3 receptor-blocking activity, and/or increased specificity to one or more of αvβ1, αvβ3, αvβ5, αvβ6 and αvβ8, and other integrins, such as α5β1. The coding sequence for a disintegrin variant can be obtained by modifying a coding sequence for a disintegrin derived from a snake venom. The disintegrin can be chosen from one of rhodostomin, albolabrin, applagin, basilicin, batroxostatin, bitistatin, cereberin, cerastin, crotatroxin, durissin, elegantin, flavoridin, flavostatin, halysin, halystatin, jararacin, jarastatin, kistrin, lachesin, lutosin, molossin, salmosin, saxatilin, tergeminin, trimestatin, trimucrin, trimutase, ussuristatin, and viridin.

Thus, another general aspect of the invention relates to a polynucleotide encoding a disintegrin variant of the invention. Yet another general aspect of the invention relates to host cells comprising a polynucleotide encoding a disintegrin variant of the invention.

Typically, a heterologous peptide, whether modified or unmodified, may be expressed on its own, as described above, or as a fusion protein, and may include not only secretion signals, but also a secretory leader sequence. A secretory leader sequence of the invention may direct certain proteins to the endoplasmic reticulum (ER) or periplasma. The ER separates the membrane-bound proteins from other proteins. Once localized to the ER, proteins can be further directed to the Golgi apparatus for distribution to vesicles, including secretory vesicles, the plasma membrane, lysosomes, and other organelles. In the case of periplasma, the protein is secreted into the periplasma space of a Gram negative bacterium, such as an *Escherichia coli*.

Additionally, peptide moieties and/or purification tags can be added to the disintegrin variants. Such regions may be removed prior to final preparation of the polypeptide. The addition of peptide moieties to polypeptides to engender secretion or excretion, to improve stability, and to facilitate purification, among other reasons, are familiar and routine techniques in the art. Suitable purification tags include, for example, V5, polyhistidines, avidin, and biotin. Conjugation of peptides to compounds such as biotin can be accomplished using techniques well known in the art. (Hermanson ed. (1996) Bioconjugate Techniques; Academic Press). Peptides can also be conjugated with radioisotopes, toxins, enzymes, fluorescent labels, colloidal gold, nucleic acids, vinorelbine, and doxorubicin using techniques known in the art. (Hermanson ed. (1996) Bioconjugate Techniques; Academic Press; Stefano et al. (2006).

Fusion partners suitable for use in the invention include, for example, fetuin, human serum albumin, immunoglobulin CH2/CH3 domains (Fc), and/or one or more of their fragments. Conjugated proteins, such as polyethylene glycol conjugates, are also provided.

The peptides of the invention can also be chemically synthesized using techniques known in the art (e.g., see Hunkapiller et al., *Nature,* 310:105 111 (1984); Grant ed. (1992) Synthetic Peptides, A Users Guide, W.H. Freeman and Co.; U.S. Pat. No. 6,974,884)). For example, a polypeptide corresponding to a fragment of a polypeptide can be synthesized by use of a peptide synthesizer or through the use of solid-phase methods known in the art.

Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The disintegrin variant of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In one embodiment, high performance liquid chromatography ("HPLC") is employed for purification. Well known techniques for refolding protein may be employed to regenerate active conformation when the polypeptide is denatured during isolation and/or purification.

A disintegrin variant of the invention can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran, and dextran derivatives. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S. (1995) Bioconjugate Chem., 6:150-165; Monfardini, C., et al. (1995) Bioconjugate Chem. 6:62-69; U.S. Pat. Nos. 4,640, 835; 4,496,689; 4,301,144; 4,670,417; 4,791,192; 4,179, 337, or WO 95/34326.

Pharmaceutical Compositions

Another general aspect of the invention relates to a pharmaceutical composition comprising a disintegrin variant of the invention and a pharmaceutically acceptable carrier. Depending on the need, the pharmaceutical compositions can be formulated into preparations in solid, semi-solid, liquid, or gaseous forms, such as tablets, capsules, powders, granules, ointments, solutions, suppositories, injections, inhalants and aerosols. The following methods and excipients are merely exemplary and are in no way limiting.

In some embodiments, a disintegrin variant of the invention is provided in formulation with pharmaceutically acceptable carriers, excipients, and diluents, of which a wide variety are known in the art. These pharmaceutical carriers, excipients, and diluents include those listed in the USP pharmaceutical excipients listing. USP and NF Excipients, Listed by Categories, p. 2404-2406, USP 24 NF 19, United States Pharmacopeial Convention Inc., Rockville, Md. (ISBN 1-889788-03-1). Pharmaceutically acceptable excipients, such as vehicles, adjuvants, carriers, or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable carriers include, but are not limited to, water, dextrose, trehalose, histidine, glycerol, saline, ethanol, and combinations thereof. The carrier can contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents can be added as necessary. Percutaneous penetration enhancers such as Azone can also be included.

Actual methods of preparing such dosage forms are known, or will be apparent, to those skilled in the art. The composition or formulation to be administered will, in any event, contain a quantity of the agent adequate to achieve the desired state in the subject being treated.

In certain embodiments, disintegrin variant of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. Other formulations for oral or parenteral delivery can also be used, as conventional in the art.

In pharmaceutical dosage forms, the pharmaceutical compositions of the invention can be administered in the form of their pharmaceutically acceptable salts, or they can also be used alone or in appropriate association, as well as in combination, with other pharmaceutically active compounds. The subject compositions are formulated in accordance to the mode of potential administration. In a preferred embodiment, the pharmaceutical composition is formulated for parental administration, such as in a liquid form for injection.

Methods of Treatment

The invention also relates to uses of the disintegrin variants in treating and/or preventing a disease associated with one or more integrins selected from the group consisting of $\alpha5\beta1$, $\alpha v\beta1$, $\alpha v\beta3$, $\alpha v\beta5$, $\alpha v\beta6$ and $\alpha v\beta8$ in a subject in need thereof. Such diseases include, but are not limited to, osteoporosis, bone tumor or cancer growth and symptoms related thereto, angiogenesis-related tumor growth and metastasis, tumor metastasis in bone, malignancy-induced hypercalcemia, angiogenesis-related eye diseases, Paget's disease, rheumatic arthritis, and osteoarthritis. The method comprises administering to the subject in need of the treatment a pharmaceutical composition comprising a therapeutically effective amount of a disintegrin variant of the invention and a pharmaceutically acceptable carrier.

In one embodiment of the invention, a disintegrin variant of the invention is used for treatment and/or prevention of an angiogenesis-related eye disease, which includes, but is not limited to, age-related macular degeneration, diabetic retinopathy, corneal neovascularizing diseases, ischaemia-induced neovascularizing retinopathy, high myopia, and retinopathy of prematurity.

In another embodiment of the invention, a disintegrin variant of the invention is used for treatment and/or prevention of angiogenesis-related disease, including, but not limited to, cancer, eye-related disease, such as macular degeneration, edema.

In another embodiment, the invented disintegrin variant binds to $\alpha v$-integrins present in the cornea ($\alpha v\beta5$, $\alpha v\beta6$, and $\alpha v\beta8$), mediates transforming growth factor $\beta$ (TGF$\beta$) activation, resulting in treatment of related diseases. These diseases include eye disease, arthritis and cancer. In a further aspect, the invented polypeptide is an anti-angiogenic drugs for relieving the arthritic pain and preventing bone joint destruction caused by these pathological and destructive blood vessels. The invented polypeptides can also prove to be useful when combined with conventional chemotherapy or radiation therapy, as part of a "multiple warhead" approach to attack cancer via different strategies simultaneously.

In still another embodiment of the invention, a disintegrin variant of the invention is used for treatment and/or prevention of osteoporosis. The osteoporosis is associated with a pathological condition chosen from post-menopausal estrogen deficiency, secondary osteoporosis, rheumatoid arthritis, ovariectomy, Paget's disease, bone cancer, bone tumor, osteoarthritis, increased osteoclast formation, and increased osteoclast activity. Furthermore, the osteoporosis includes, but is not limited to, an ovariectomy-induced osteoporosis or bone loss and post-menopausal osteoporosis or bone loss.

Yet another embodiment of the invention is a method of using the disintegrin variant for treatment and/or prevention of physiological changes in a mammal including a human induced by ovariectomy or post-menopausal osteoporosis. The method includes administering to the mammal in need thereof a therapeutically effective amount of an isolated polypeptide, or a pharmaceutically acceptable salt thereof, which has integrin $\alpha v\beta1$, $\alpha v\beta3$, $\alpha v\beta5$, $\alpha v\beta6$ or $\alpha5\beta1$ receptor-antagonist activity and substantially reduced integrin $\alpha IIb\beta3$ receptor-blocking activity as compared to a wild-type disintegrin, and thereby resulting in treatment and/or prevention of the ovariectomy-induced physiological change in the mammal.

In other aspect, the invention provides a method for inhibiting platelet aggregation, comprising administering an effective amount of a disintegrin variant of the invention or a pharmaceutical composition of the invention to a subject in need of such treatment.

A disintegrin variant of the invention can be administered to a subject in need of treatment by systemic injection, such as by intravenous injection; or by injection or application to the relevant site, such as by direct injection, or direct application to the site when the site is exposed in surgery; or by topical application, such as if the disorder is on the skin, for example.

A disintegrin variant of the invention can be used as monotherapy. Alternatively, the disintegrin variant of the invention can be used in combination with standard regimens to treat integrin associated diseases. For example, the peptides of the invention can be used in a combinational therapy with a therapeutically effective amount of one or more other pharmaceutical agents. Preferably, another pharmaceutical agent is selected from the group consisting of an anti-cancer agent, an anti-inflammatory agent, an immune-modulating agent and an anti-osteoporosis agent. Preferably, an anti-cancer agent is selected from the group consisting of an anti-angiogenic agent, a cytotoxic agent and an anti-neoplastic agent. The other pharmaceutical agent(s) can be administered prior to, together with, or after administration of the peptides of the invention.

In some embodiments, a disintegrin variant of the invention is particularly effective against cancers which are associated with a highly expressed osteopontin. In preferred embodiments, the polypeptides of the invention can inhibit osteopontin-induced tumor invasion.

Administration of disintegrin variants can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation.

The following examples of the invention are to further illustrate the nature of the invention. It should be understood that the following examples do not limit the invention and that the scope of the invention is to be determined by the appended claims.

EXAMPLES

Example 1

Construction of Expression Vectors Expressing Wild-Type Rho and Rho Mutants (Disintegrin Variants)

The DNA encoding Rho was composed of codons preferentially used in *Pichia pastoris*. Rho DNA was amplified by the polymerase chain reaction (PCR) with the sense primer 5'-GAATTCGAATTCCATCATCATCATCATCAT-CATGGTAAGGAATGTGACTGTTCT-3' (SEQ ID NO: 183) that had Eco R1 recognition site and encodes six histidine residues for facilitating purification. The antisense primer has the sequence of 5'-CCGCGGCCGCGGTCAGTGGTATCTTGGACAGTCAGC-3' (SEQ ID NO: 180) or 5'-CCGCGGCCGCGGT-TAGTGGTATCTTGGACAGTCAGC-3' (SEQ ID NO: 184) with Sac II recognition and a TCA (or TTA) stop codon. The PCR product was purified and then ligated into the Eco R1 and Sac II sites of the yeast recombination vector, pPICZα A. The recombinant plasmid was used to transform a DH5α strain, and colonies were selected on agar plates with low salt LB (1% tryptone, 0.5% yeast extract, 0.5% NaCl, 1.5% agar at pH 7.0) and 25 μg/ml antibiotic Zeocin.

The various DNA constructs encoding the mutants of Rho were synthesized and amplified by the PCR using an overlapping oligonucleotide strategy with primers containing Eco RI and Sac II restriction sites. For illustration purpose, Table 2 lists the consensus sequences of some disintegrin variants, and the primers used to construct these variants according to embodiments of the invention, wherein the primer sequences are presented from the 5' to 3' (left to the right).

Expression vectors encoding other variants encompassed by the invention have been or can be constructed in similar manner in view of the present disclosure. Various primers used for synthesizing or confirming disintegrin variants are listed in SEQ ID NOs: 180-305.

Example 2

Expression and Purification of Rho Mutants

The protein expression of rhodostomin mutants and variants in *Pichia pastoris* was performed according to the protocols of the *Pichia* EasyComp™ Kit with minor modifications. Briefly, a total of 10 μg plasmids containing DNA encoding rhodostomin or the variants of disintegrin were purified and digested with Sac I to linearize the plasmids. *Pichia* strain X33 was transformed with the linearized constructs by a heat shock method, using a *Pichia* Easy-Comp™ kit from Invitrogen®. The transformant integrated at the 5'AOX1 locus by a single crossover. PCR was used to analyze *Pichia* integrants to determine if the Rho gene had been integrated into the *Pichia* genome, and cells were lysed by Lyticase (Sigma). Colonies were selected on agar plates containing YPD (1% yeast extract, 2% peptone, 2% glucose, and 2% agar) and 100 μg/ml Zeocin. A number of clones with multiple copies of disintegrin insertions were selected to pick the clone for the highest variants of disintegrin protein expression.

Recombinant Rho mutants were produced as follows: selected colonies were grown in the YPD medium (1% yeast extract, 2% peptone, and 2% dextrose) containing 100 μg/ml Zeocin at 30° C. After 48 hours, cells were collected by centrifugation and grown in 1 liter of minimal methanol medium (containing 1.34% yeast nitrogen base with ammonium sulfate without amino acids and $4 \times 10^{-5}$% biotin). A total of 1% methanol was added once every 24 hours to induce Rho or variant expression for 2 days. The supernatant was collected by centrifugation and dialyzed twice against 5 liter buffer A (5 mM EDTA, 8M urea and 10 mM Na-phosphate buffer, pH 7.7). The final solution was loaded into a nickel-chelating column and eluted with a gradient of 200 mM imidazole. The recombinant rhodostomin and the variants of disintegrin were further purified by HPLC (reverse phase C18 HPLC). The purified recombinant variants of the disintegrin had a purity of greater than 95% as judged by tricine-SDS-PAGE.

TABLE 2

| Illustration of Primers Used to Construct Rho and Rho Variants | | | |
|---|---|---|---|
| Rho/Variant | | Primer Sequence | SEQ ID NO |
| RGDM | Sense | AGAGGTGACATG | (SEQ ID NO. 181) |
| GRGDM | Annse | CATGTCACCTCTACCGATTCTAC | (SEQ ID NO. 182) |

TABLE 2-continued

Illustration of Primers Used to Construct Rho and Rho Variants

| Rho/Variant | | Primer Sequence | SEQ ID NO |
|---|---|---|---|
| Rho-1 | Sense | GAATTCGAATTCCATCATCATCATCA TCATGGTAAGGAATGTGACTGTTCT | (SEQ ID NO. 183) |
| Rho-2 | Antisense | CCGCGGCCGCGGTTAGTGGTATCTTG GACAGTCAGC | (SEQ ID NO. 184) |
| LRGDM | Antisense | CATGTCACCTCTCAAGATTCTAC | (SEQ ID NO. 185) |
| RRGDM | Antisense | CATGTCACCTCTTCTGATTCTAC | (SEQ ID NO. 186) |
| VRGDM | Antisense | CATGTCACCTCTAACGATTCTAC | (SEQ ID NO. 187) |
| HRGDM | Antisense | CATGTCACCTCTATGGATTCTAC | (SEQ ID NO. 188) |
| WRGDM | Antisense | CATGTCACCTCTCCAGATTCTAC | (SEQ ID NO. 189) |
| FRGDM | Antisense | CATGTCACCTCTAAAGATTCTAC | (SEQ ID NO. 190) |
| P48A-1 | Sense | TGTAGAATCGCTAGAGGTGACATG | (SEQ ID NO. 191) |
| P48A-2 | Antisense | CATGTCACCTCTAGCGATTCTACA | (SEQ ID NO. 192) |
| SRGDM | Antisense | CATGTCACCTCTAGAGATTCTAC | (SEQ ID NO. 193) |
| MRGDM | Antisense | CATGTCACCTCTCATGATTCTAC | (SEQ ID NO. 194) |
| TRGDM | Antisense | CATGTCACCTCTAGTGATTCTAC | (SEQ ID NO. 195) |
| NRGDM | Antisense | CATGTCACCTCTGTTGATTCTAC | (SEQ ID NO. 196) |
| QRGDM | Antisense | CATGTCACCTCTTTGGATTCTAC | (SEQ ID NO. 197) |
| YRGDM | Antisense | CATGTCACCTCTGTAGATTCTAC | (SEQ ID NO. 198) |
| IRGDM | Antisense | CATGTCACCTCTAATGATTCTAC | (SEQ ID NO. 199) |
| KRGDM | Antisense | CATGTCACCTCTCTTGATTCTAC | (SEQ ID NO. 200) |
| ERGDM | Antisense | CATGTCACCTCTTTCGATTCTAC | (SEQ ID NO. 201) |
| DRGDM | Antisense | CATGTCACCTCTATCGATTCTAC | (SEQ ID NO. 202) |
| RAD | Sense | GTAGAATCCCAAGAGCTGACATGCC | (SEQ ID NO. 203) |
| RRD | Sense | GTAGAATCCCAAGAAGAGACATGCC | (SEQ ID NO. 204) |
| RND | Sense | GTAGAATCCCAAGAAACGACATGCC | (SEQ ID NO. 205) |
| RDD | Sense | GTAGAATCCCAAGAGATGACATGCC | (SEQ ID NO. 206) |
| RED | Sense | GTAGAATCCCAAGAGAAGACATGCC | (SEQ ID NO. 207) |
| RQD | Sense | GTAGAATCCCAAGACAAGACATGCC | (SEQ ID NO. 208) |
| RKD | Sense | GTAGAATCCCAAGAAAGGACATGCC | (SEQ ID NO. 2(9) |
| RMD | Sense | GTAGAATCCCAAGAATGGACATGCC | (SEQ ID NO. 210) |
| RFD | Sense | GTAGAATCCCAAGATTTGACATGCC | (SEQ ID NO. 211) |

Example 3

Rho Mutants Selectively Inhibited Cell Attachment Mediated by Different αv Integrins and α5β1 Integrin The inhibitory activities of Rho mutants and variants were evaluated by cell adhesion inhibition assays as described previously (Zhang, et al., 1998 *J Biol Chem* 73:7345-7350). The adhesions of CHO-αIIbβ3 cells to fibrinogen, CHO-αvβ3 cells to fibrinogen, K562 cells to fibronectin, HT-29 cells to vitronectin, and HT-29 cells to fibronectin were used to determine the inhibitory activities of tested protein to integrins αIIbβ3, αvβ3, α5β1, αvβ5, and αvβ6. Briefly, 96-well Immulon-2 microtiter plates (Costar, Corning, N.Y.) were coated with 100 µl of phosphate-buffered saline (PBS: 10 mM phosphate buffer, 0.15M NaCl, pH 7.4) containing substrates at a concentration of 50-500 nM, and incubated overnight at 4° C. The substrates and their coating concentrations were fibrinogen (Fg) 200 µg/ml, vitronectin (Vn) 50 µg/ml, and fibronectin (Fn) 25 µg/ml. Non-specific protein binding sites were blocked by incubating each well with 200 µL of heat-denatured 1% bovine serum albumin (BSA)

(Calbiochem) at room temperature for 1.5 h. The heat-denatured BSA was discarded and each well was washed twice with 200 µL of PBS.

CHO cells that expressed the integrins αvβ3 (CHO-αvβ3) and αIIbβ3 (CHO-αIIbβ3) were kindly provided by Dr. Y. Takada (Scripps Research Institute) and maintained in DMEM. Human erythroleukemia K562 and colorectal adenocarcinoma HT-29 cells were purchased from ATCC and cultured in Roswell Park Memorial Institute (RPMI)-1640 medium containing 5% FCS. Harvested K562 and HT-29 cells were washed in PBS buffer containing 1 mM EDTA and resuspended in Tyrode's buffer (150 mM NaCl, 5 mM KCl, and 10 mM Hepes) [pH 7.35] containing 1 mM $MgSO_4$, 2 mM $CaCl_2$, and 500 µM $MnCl_2$. Cells (CHO, K562, and HT-29) were diluted to $3 \times 10^5$ cells/mL, and 100 µL of the cells were used for the assay. Rho and its mutants were added to the cultured cells and incubated at 37° C., 5% $CO_2$ for 15 minutes. Rho and its variants were used as inhibitors at the concentrations of 0.001-500 µM. The treated cells were then added into the coated plate and reacted at 37° C., 5% $CO_2$ for 1 hour. The incubation solution was then discarded and non-adhered cells were removed by washing twice with 200 µL PBS.

Bound cells were quantified by crystal violet staining. Briefly, the well was fixed with 100 µL of 10% formalin for 10 minutes and dried. Fifty microliters of 0.05% crystal violet were then added into the well at room temperature for 20 minutes. Each well was washed with 200 µL of distilled water four times and dried. Colorization was carried out by adding 150 µL of colorizing solution (50% alcohol and 0.1% acetic acid). The resulting absorbance was read at 600 nm and the readings were correlated with the number of adhering cells. Inhibition was defined as % inhibition=100−[$OD_{600}$ (Rho wild type or disintegrin-treated sample)/$OD_{600}$ (untreated sample)]×100.

$IC_{50}$ was defined as the concentration (nM) of a disintegrin variant required for 50% inhibition of the cell adhesion mediated by a particular integrin. Therefore, lower $IC_{50}$ indicates greater specificity or potency of the disintegrin variant in inhibiting the cell adhesion activity of the respective integrin, thus higher binding activity (or selectivity) of the disintegrin variant to the respective integrin. The $IC_{50}$ results are summarized in Tables 3 to 14 below.

A series of Rho mutants involved in the RGD loop region ($R^{50}XD$, $^{48}XRGD$ (SEQ ID NO: 341), $XRGD^{52}XP$ (SEQ ID NO: 342), $XRGDMX^{53}$ (SEQ ID NO: 343), $^{46}X^{47}XPRGD$ (SEQ ID NO: 344), and $ARGD^{51}X^{52}X$ (SEQ ID NO: 340)), the linker region, and C-terminal region were recombinantly expressed and purified to homogeneity. The cell adhesion and platelet aggregation assays were used to determine their integrin-binding affinity. It was found that variants of rhodostomin or disintegrins with one or more modifications in these regions have different selective binding affinity to αVβ3, αVβ5, αVβ6, α5β1 and αIIbβ3 (Tables 3-14).

For example, it was found that Rho variants with certain mutations in the RXD motif, in which the "Gly50 (G)" residue was replaced by Leu (L), Val (V), Ile (I), Glu (E), Asp (D), Gln (Q), Phe (F), Trp (W), His (H), Lys (K), or Arg (R), had their highest effects on integrins in the following order: αIIbβ3 (~1686-fold)>α5β1 (~586-fold)>αvβ5 (~348-fold)>αvβ6 (~179-fold)>αvβ3 (~26-fold), showing their binding selectivity to αVβ3 (Table 3). Rho variants with the mutation in the XRGD (SEQ ID NO: 341) motif, in which the $P^{48}$ residue was replaced by other amino acids, had their highest effects on integrins in the following order: α5β1 (~71-fold)>αIIbβ3 (~41-fold)>αvβ3 (~5-fold) (Table 4). Rho variants with the mutation in the XRGDXP (SEQ ID NO: 342) motif, in which the M52 residue was replaced by other amino acids, had their highest effects on integrins in the following order: αIIbβ3 (~209-fold)>α5β1 (~122-fold)>αVβ3 (~14-fold) (Table 5). Rho variants with the mutation in the XRGDMX (SEQ ID NO: 343) motif, in which the $P^{53}$ residue was replaced by other amino acids, had their highest effects on integrins in the following order: αIIbβ3 (~258-fold)>α5β1 (~45-fold)>αVβ3 (~40-fold) (Table 6). Rho variants with the mutation in the XXPRGD (SEQ ID NO: 344) motif, in which the R46 and I47 residues were replaced by other amino acids, had their highest effects on integrins in the following order: αIIbβ3 (~73-fold)>α5β1 (~19-fold)>αVβ3 (~10-fold) (Table 7). These results showed that the mutations in the RGD loop exhibited significant effect on the inhibitory activity in integrins αIIbβ3 and α5β1, but not αVβ3 integrin.

Mutants of rhodostomin or disintegrins with one or more modifications in addition to the RGD motif, e.g., in the linker region or the C-terminus, exhibited the capability to selectively binding to αVβ3, αVβ5, αVβ6, α5β1 or αIIbβ3 (Table 8-14). For example, Rho variants with the mutation in the linker region, in which the SRAGKIC (SEQ ID NO: 332) was replaced by KKKRTIC (SEQ ID NO: 306), KKARTIC (SEQ ID NO: 313), MKKGTIC (SEQ ID NO: 307), IEEGTIC (SEQ ID NO: 308), LKEGTIC (SEQ ID NO: 310), AKKRTIC (SEQ ID NO: 311), KAKRTIC (SEQ ID NO: 312), KGAGKIC (SEQ ID NO: 309), KKKATIC (SEQ ID NO: 314), KKKRAIC (SEQ ID NO: 315), KAKRAIC (SEQ ID NO: 316), and SKAGTIC (SEQ ID NO: 317) amino acids, had their highest effects on integrins in the following order: αIIbβ3 (~2-fold)>α5β1 (~5-fold)>αVβ3 (~14-fold) (Table 8). These results showed that the mutations in the linker region of Rho exhibited significant effect on the inhibitory activity in integrin αVβ3.

Rho variants with the mutation in the C-terminal region, in which the PRYH (SEQ ID NO: 334) was replaced by PGLYG (SEQ ID NO: 324), PRNRFH (SEQ ID NO: 321), PRNRFHA (SEQ ID NO: 322), PRWNDL (SEQ ID NO: 319), PRNGLYG (SEQ ID NO: 323), and PRNPWNG (SEQ ID NO: 320) amino acids, had their highest effects on integrins in the following order: αIIbβ3 (~13-fold)>αVβ5 (~8-fold)=αVβ6 (~8-fold)>αVβ3 (~4-fold)>α5β1 (~2-fold) (Table 9). These results showed that the mutations on the C-terminal region of Rho exhibited significant effect on the inhibitory activity in integrins αIIbβ3, αVβ5, and αVβ6.

Rho variants with the mutation in the C-terminal region, in which PRYH (SEQ ID NO: 334) was replaced by PGLYG (SEQ ID NO: 324), PPLYG (SEQ ID NO: 327), PRLYG (SEQ ID NO: 328), PGLY (SEQ ID NO: 325), PYLYG (SEQ ID NO: 352) and PELYG (SEQ ID NO: 337) amino acids, had their highest effects on integrins in the following order: αIIbβ3 (~6493-fold)>α5β1 (~40-fold)>αvβ5 (~8-fold)>αvβ6 (~6-fold)>αvβ3 (~1-fold), showing its significant effect on integrins αIIbβ3 and α5β1 (Table 10).

Disintegrin (Rho) variants specific to integrins αvβ3 and α5β1 were successfully obtained by modifying the RGD loop region, the linker region, and C-terminal region of Rho. For example, the mutant $^{39}$KKART-$^{46}$ARGRGDNP-$^{66}$DLYG (SEQ ID NO: 147) exhibited an excellent inhibitory activity to integrins αvβ3 and α5β1 but not to αIIbβ3, αvβ5, and αvβ6 (Table 11). The mutations in the RGD loop and linker region increased its activity in inhibiting integrins αvβ3 and α5β1 and significantly decreased its activity in inhibiting integrin αIIbβ3. The mutations in the C-terminal region decreased its activity in inhibiting integrins αvβ5, and αvβ6.

Disintegrin (Rho) variants specific to integrins αvβ3, αvβ5, and α5β1 were successfully obtained by modifying the RGD loop region, the linker region, and C-terminal region of Rho. For example, the mutant $^{39}$KKART-$^{46}$AR-GRGDDL-$^{66}$GLYG (SEQ ID NO: 339) exhibited an excellent inhibitory activity to αvβ3, αvβ5, and α5β1 but not to αIIbβ3 and αvβ6 (Table 12). The mutations of SRAGKIC (SEQ ID NO: 332) into KKARTIC (SEQ ID NO: 313) in the linker region increased its activity in inhibiting RGD-binding integrins. The mutations of R46A, I47R, P48A, M52D, and P53L in the RGD loop decreased its activity in inhibiting integrins αIIbβ3 and αVβ6. The mutations of PRYH (SEQ ID NO: 334) into PGLYG (SEQ ID NO: 324) in the C-terminal region decreased its activity in inhibiting integrin αIIbβ3.

Disintegrin (Rho) variants specific to integrins αvβx and α5β1 were successfully obtained by modifying the RGD loop region, the linker region, and C-terminal region of Rho. For example, the mutant $^{39}$KKART-$^{46}$ARGRGDNP-$^{66}$RYH (SEQ ID NO: 123) exhibit an excellent inhibitory to integrins αvβ3 and α5β1 but not to αIIbβ3, αvβ5, and αvβ6 (Table 13). The mutations in the RGD loop and linker region increased its activity in inhibiting integrins αVβ3 and α5β1 and significantly decreased its activity in inhibiting integrin αIIbβ3. The mutations on the C-terminal region decreased its activity in inhibiting integrins αvβ5, and αvβ6.

Example 4

Inhibition of Platelet Aggregation by Rho Mutants

Disintegrin (Rho) variants were also tested for their ability to inhibit platelet aggregation that is mediated by αIIbβ3. Venous blood (9 parts) samples from healthy donors who had not received any medication for at least two weeks were collected in 3.8% sodium citrate (1 part). Blood samples were centrifuged at 150×g for 10 min to obtain platelet-rich plasma (PRP) and allowed to stand for 5 min, and PRP was collected. The platelet-poor plasma (PPP) was prepared from the remaining blood by centrifuging at 2000×g for 25 min. The PPP platelet count was measured on a hematology analyzer and diluted to 250,000 platelets/μl. A solution of 190 μl of PRP and 10 μl of either Rho or PBS buffer were incubated for 5 min in a Hema Tracer 601 aggregometer at 37° C. Ten microliters of 200 μM adenosine diphosphate (ADP) were further added to monitor the response of platelet aggregation by light transmission. The results on inhibition of platelet aggregation are also summarized in Tables 3 to 14 below.

TABLE 3

Integrin Selectivity and Inhibition of Platelet Aggregation by the RXD Disintegrin Variants

| | Consensus Sequence | IC$_{50}$ (nM) [Interaction towards targets] | | | Platelet Aggregation (nM) |
|---|---|---|---|---|---|
| | | α5β1 | αVβ3 | αIIbβ3 | |
| | $^{49}$RGD (Rho wild type) (SEQ ID NO: 1) | 216.0 | 11.4 | 17.8 | 77.5 |
| 1. | RAD (SEQ ID NO: 7) | 14425.3 | 74.6 | 299.1 | 176.5 |
| 2. | RPD (SEQ ID NO: 8) | 104452.5 | 2275.0 | 6122.3 | 1236.0 |
| 3. | RVD (SEQ ID NO: 9) | 3296.0 | 63.9 | 2554.3 | 523.8 |
| 4. | RLD (SEQ ID NO: 10) | 3043.3 | 32.4 | 1998.8 | 480.3 |
| 5. | RID (SEQ ID NO: 11) | 2604.3 | 119.9 | 4895.0 | 669.6 |
| 6. | RMD (SEQ ID NO: 12) | 4915.6 | 188.7 | 185.4 | 414.4 |
| 7. | RFD (SEQ ID NO: 13) | 3325.3 | 274.6 | 5486.6 | 652.6 |
| 8. | RYD (SEQ ID NO: 14) | 1231.7 | 247.5 | 2001.6 | 508.3 |
| 9. | RWD (SEQ ID NO: 15) | 1104.8 | 291.0 | 2425.8 | 476.5 |
| 10. | RSD (SEQ ID NO: 16) | 6254.5 | 78.1 | 142.2 | 189.9 |
| 11. | RTD (SEQ ID NO: 17) | 5420.6 | 54.1 | 1154.3 | 281.7 |

TABLE 3 -continued

Integrin Selectivity and Inhibition of Platelet Aggregation by the RXD Disintegrin Variants

| | Consensus Sequence | IC$_{50}$ (nM) [Interaction towards targets] | | | Platelet Aggregation (nM) |
|---|---|---|---|---|---|
| | | α5β1 | αVβ3 | αIIbβ3 | |
| 12. | RND (SEQ ID NO: 18) | 43192.0 | 88.0 | 647.1 | 186.7 |
| 13. | RQD (SEQ ID NO: 19) | 77335.0 | 132.3 | 2920.6 | 539.4 |
| 14. | RDD (SEQ ID NO: 20) | 131702.0 | 123.5 | 10688.3 | 1216.5 |
| 15. | RED (SEQ ID NO: 21) | 86954.5 | 89.9 | 35411.3 | 2162.3 |
| 16. | RHD (SEQ ID NO: 22) | 6489.0 | 131.6 | 2109.0 | 465.7 |
| 17. | RKD (SEQ ID NO: 23) | 150186.5 | 387.8 | 33915.7 | 1527.3 |
| 18. | RRD (SEQ ID NO: 23) | 111949.0 | 404.2 | 4372.3 | 401.7 |

TABLE 4

Integrin Selectivity and Inhibition of Platelet Aggregation by the XRGD Disintegrin Variants

| | Consensus Sequence | IC$_{50}$ (nM) [Interaction towards targets] | | | Platelet Aggregation (nM) |
|---|---|---|---|---|---|
| | | αvβ3 | α5β1 | αIIbβ3 | |
| | $^{48}$ERGD (Rho wild type) (SEQ ID NO: 1) | 13.0 | 256.8 | 21.0 | 83.2 |
| 1. | DRGD (SEQ ID NO: 26) | 15.3 | 4188.3 | 860.2 | 631.3 |
| 2. | ERGD (SEQ ID NO: 27) | 12.9 | 522.2 | 677.2 | 528.1 |
| 3. | GRGD (SEQ ID NO: 25) | 19.6 | 92.2 | 68.4 | 370.2 |
| 4. | ARGD (SEQ ID NO: 32) | 15.8 | 59.0 | 31.6 | 110.3 |
| 5. | IRGD (SEQ ID NO: 34) | 20.4 | 139.4 | 38.6 | 214.6 |
| 6. | SRGD (SEQ ID NO: 33) | 12.9 | 251.3 | 28.5 | 115.1 |
| 7. | VRGD (SEQ ID NO: 41) | 11.4 | 310.6 | 20.4 | 68.9 |
| 8. | MRGD (SEQ ID NO: 42) | 41.0 | 248.2 | 39.8 | 142.0 |
| 9. | FRGD (SEQ ID NO: 40) | 14.9 | 282.1 | 36.1 | 124.0 |

TABLE 4 -continued

Integrin Selectivity and Inhibition of Platelet Aggregation by the XRGD Disintegrin Variants

| | Consensus Sequence | IC$_{50}$ (nM) [Interaction towards targets] | | | Platelet Aggregation (nM) |
|---|---|---|---|---|---|
| | | αvβ3 | α5β1 | αIIbβ3 | |
| 10. | LRGD (SEQ ID NO: 29) | 11.3 | 283.4 | 22.1 | 168.0 |
| 11. | IRGD (SEQ ID NO: 30) | 17.6 | 281.7 | 47.9 | 183.9 |
| 12. | VRGD (SEQ ID NO: 28) | 19.5 | 194.7 | 47.6 | 136.9 |
| 13. | MRGD (SEQ ID NO: 31) | 11.3 | 222.7 | 26.4 | 137.4 |
| 14. | QRGD (SEQ ID NO: 36) | 8.8 | 190.9 | 60.9 | 128.9 |
| 15. | NRGD (SEQ ID NO: 35) | 8.0 | 264.6 | 28.5 | 274.4 |
| 16. | KRGD (SEQ ID NO: 38) | 24.1 | 246.6 | 22.3 | 157.0 |
| 17. | RRGD (SEQ ID NO: 37) | 15.5 | 214.4 | 30.0 | 179.4 |
| 18. | HRGD (SEQ ID NO: 39) | 11.6 | 194.8 | 24.4 | 115.2 |

TABLE 5

Integrin Selectivity and Inhibition of Platelet Aggregation by the ARGDXP Disintegrin Variants

| | Consensus Sequence | IC$_{50}$ (nM) [Interaction towards targets] | | | Platelet Aggregation (nM) |
|---|---|---|---|---|---|
| | | αvβ3 | α5β1 | αIIbβ3 | |
| 1. | $^{48}$ARGDWP (wild type) (SEQ ID NO: 1) | 13.0 | 256.8 | 21.0 | 83.2 |
| 2. | ARGDYP (SEQ ID NO: 32) | 15.8 | 59.0 | 31.6 | 110.3 |
| 3. | ARGDDP (SEQ ID NO: 44) | 45.3 | 5044.5 | 850.9 | 752.7 |
| 4. | ARGDEP (SEQ ID NO: 45) | 156.3 | 2436.0 | 1063.0 | 518.8 |
| 5. | ARGDLP (SEQ ID NO: 46) | 19.6 | 517.4 | 72.5 | 100.5 |
| 6. | ARGDVP (SEQ ID NO: 47) | 21.5 | 368.2 | 36.2 | 145.7 |
| 7. | ARGDIP (SEQ ID NO: 48) | 34.5 | 139.7 | 112.5 | 200.0 |
| 8. | ARGDKP (SEQ ID NO: 49) | 18.8 | 199.7 | 70.5 | 106.9 |

TABLE 5-continued

Integrin Selectivity and Inhibition of Platelet Aggregation by the ARGDXP Disintegrin Variants

| | Consensus Sequence | IC$_{50}$ (nM) [Interaction towards targets] | | | Platelet Aggregation (nM) |
|---|---|---|---|---|---|
| | | αvβ3 | α5β1 | αIIbβ3 | |
| 9. | ARGDXP (SEQ ID NO: 50) | 11.1 | 199.1 | 247.4 | 149.4 |
| 10. | ARGDSP (SEQ ID NO: 51) | 36.9 | 138.8 | 71.6 | 146.2 |
| 11. | ARGDIP (SEQ ID NO: 52) | 26.9 | 178.7 | 51.4 | 167.7 |
| 12. | ARGDNP (SEQ ID NO: 53) | 18.3 | 44.1 | 262.7 | 213.6 |
| 13. | ARGDQP (SEQ ID NO: 54) | 18.5 | 88.1 | 68.1 | 171.9 |
| 14. | ARGDAP (SEQ ID NO: 55) | 29.6 | 52.0 | 12.4 | 129.8 |
| 15. | ARGDYP (SEQ ID NO: 56) | 38.5 | 45.2 | 44.7 | 76.2 |
| 16. | ARGDEP (SEQ ID NO: 57) | 17.5 | 51.1 | 16.6 | 99.4 |
| 17. | ARGDFP (SEQ ID NO: 58) | 55.0 | 91.9 | 39.1 | 97.8 |
| 18. | ARGDRP (SEQ ID NO: 59) | 3.0 | 49.1 | 51.2 | 77.1 |
| 19. | ARGDGP (SEQ ID NO: 60) | 224.7 | 840.5 | 2643.3 | 359.6 |
| 20. | ARGDEP (SEQ ID NO: 61) | 40940.0 | 62460.0 | 64665.0 | 49410.0 |

TABLE 6

Integrin Selectivity and Inhibition of Platelet Aggregation by the ARGDMX Disintegrin Variants

| | Consensus Sequence | IC$_{50}$ (nM) [Interaction towards targets] | | | Platelet Aggregation (nM) |
|---|---|---|---|---|---|
| | | αvβ3 | α5β1 | αIIbβ3 | |
| | $^{48}$ARGDM (Rho wild type) (SEQ ID NO: 1) | 13.0 | 256.8 | 21.0 | 83.2 |
| 1. | ARGDM (SEQ ID NO: 32) | 15.8 | 59.0 | 135.2 | 110.3 |
| 2. | ARGDMN (SEQ ID NO: 62) | 97.2 | 4496.6 | 557.6 | 240.4 |
| 3. | ARGDMQ (SEQ ID NO: 63) | 93.0 | 6212.3 | 2317.3 | 171.5 |
| 4. | ARGDMD (SEQ ID NO: 64) | 144.6 | 11416.3 | 1198.3 | 196.1 |

TABLE 6-continued

Integrin Selectivity and Inhibition of Platelet Aggregation by the ARGDMX Disintegrin Variants

| | Consensus Sequence | IC$_{50}$ (nM) [Interaction towards targets] | | | Platelet Aggregation |
|---|---|---|---|---|---|
| | | αvβ3 | α5β1 | αIIbβ3 | (nM) |
| 5. | ARGDME (SEQ ID NO: 65) | 196.0 | 5619.7 | 2792.0 | 200.8 |
| 6. | ARGDMH (SEQ ID NO: 66) | 118.7 | 3329.3 | 3297.8 | 216.7 |
| 7. | ARGDMR (SEQ ID NO: 67) | 213.8 | 9787.8 | 1142.4 | 86.5 |
| 8. | ARGDMK (SEQ ID NO: 68) | 398.9 | 16794.7 | 1909.7 | 84.1 |
| 9. | ARGDMG (SEQ ID NO: 69) | 83.5 | 4607.8 | 7057.7 | 224.5 |
| 10. | ARGDML (SEQ ID NO: 70) | 57.4 | 785.6 | 1328.3 | 165.5 |
| 11. | ARGDMW (SEQ ID NO: 71) | 18.6 | 1386.7 | 1002.0 | 130.2 |
| 12. | ARGDMF (SEQ ID NO: 72) | 16.8 | 755.8 | 1280.0 | 187.5 |
| 13. | ARGDMY (SEQ ID NO: 73) | 10.7 | 505.7 | 2212.7 | 160.1 |
| 14. | ARGDMM (SEQ ID NO: 74) | 20.9 | 687.0 | 340.7 | 103.1 |
| 15. | ARGDMA (SEQ ID NO: 75) | 11.3 | 1090.7 | 1237.3 | 138.6 |
| 16. | ARGDMI (SEQ ID NO: 76) | 10.0 | 673.2 | 688.6 | 129.5 |
| 17. | ARGDMV (SEQ ID NO: 77) | 12.9 | 139.1 | 181.6 | 139.3 |
| 18. | ARGDML (SEQ ID NO: 78) | 16.1 | 218.4 | 562.7 | 115.8 |

TABLE 7

Integrin Selectivity and Inhibition of Platelet Aggregation by the XXPRGD Disintegrin Variants

| | Consensus Sequence | IC$_{50}$ (nM) [Interaction towards targets] | | | Platelet Aggregation |
|---|---|---|---|---|---|
| | | αvβ3 | α5β1 | αIIbβ3 | (nM) |
| | $^{46}$RIPRGD (Rho wild type) (SEQ ID NO: 1) | 13.0 | 256.8 | 21.7 | 83.2 |
| 1. | RR (SEQ ID NO: 79) | 3.5 | 69.5 | 22.0 | 122.3 |
| 2. | RM (SEQ ID NO: 80) | 8.3 | 393.3 | 31.5 | 198.4 |

TABLE 7 -continued

Integrin Selectivity and Inhibition of Platelet Aggregation by the XXPRGD Disintegrin Variants

| | Consensus Sequence | IC$_{50}$ (nM) [Interaction towards targets] | | | Platelet Aggregation (nM) |
|---|---|---|---|---|---|
| | | αvβ3 | α5β1 | αIIbβ3 | |
| 3. | RV (SEQ ID NO: 81) | 11.9 | 256.8 | 36.9 | 180.6 |
| 4. | RA (SEQ ID NO: 82) | 15.5 | 383.0 | 94.1 | 178.4 |
| 5. | RQ (SEQ ID NO: 83) | 15.9 | 768.1 | 63.6 | 200.3 |
| 6. | RE (SEQ ID NO: 84) | 13.6 | 1292.3 | 51.1 | 189.7 |
| 7. | RF (SEQ ID NO: 85) | 4.9 | 351.5 | 17.0 | 159.4 |
| 8. | RP (SEQ ID NO: 86) | 18.8 | 460.7 | 89.3 | 397.7 |
| 9. | KR (SEQ ID NO: 87) | 5.1 | 38.1 | 14.3 | 170.0 |
| 10. | KK (SEQ ID NO: 88) | 14.2 | 76.6 | 36.7 | 235.5 |
| 11. | KM (SEQ ID NO: 89) | 9.1 | 481.1 | 34.8 | 205.8 |
| 12. | KI (SEQ ID NO: 90) | 12.1 | 449.8 | 70.3 | 152.7 |
| 13. | | | | | |
| 14. | EI (SEQ ID NO: 91) | 6.3 | 458.6 | 35.5 | 239.3 |
| 15. | QI (SEQ ID NO: 92) | 7.3 | 823.8 | 51.2 | 467.0 |
| 16. | AI (SEQ ID NO: 93) | 62.1 | 1293.3 | 188.7 | 587.2 |
| 17. | BI (SEQ ID NO: 94) | 18.7 | 913.4 | 477.1 | 1468.0 |

TABLE 8

Integrin Selectivity and Inhibition of Platelet Aggregation by the Disintegrin Variants with Mutant RGD Loop, Mutant Linker and/or Mutant C-Terminus

| | Consensus Sequence | IC$_{50}$ (nM) [Interaction towards targets] | | | |
|---|---|---|---|---|---|
| | | Platelet Aggregation | αIIbβ3 | αVβ3 | α5β1 |
| | $^{39}$SRAGK-$^{46}$RIPRGDMP-$^{67}$YH (Rho wild type) (SEQ ID NO: 1) | 64.2 | 33.8 | 18.8 | 223.4 |
| 1. | KKKRT RIPRGDMP YH (SEQ ID NO: 127) | 104.5 | 25.6 | 1.3 | 76.1 |

TABLE 8 -continued

Integrin Selectivity and Inhibition of Platelet Aggregation by the Disintegrin Variants with Mutant RGD Loop, Mutant Linker and/or Mutant C-Terminus

| | Consensus Sequence | IC$_{50}$ (nM) [Interaction towards targets] | | | |
|---|---|---|---|---|---|
| | | Platelet Aggregation | αIIbβ3 | αVβ3 | α5β1 |
| 2. | SRAGK RIARGDNP YH (SEQ ID NO: 128) | 125.4 | 256.0 | 22.6 | 40.0 |
| 3. | KKKRT RIARGDNP YH (SEQ ID NO: 129) | 88.2 | 133.4 | 5.9 | 10.0 |
| 4. | SRAGK RIARGDNP NGLYG (SEQ ID NO: 347) | 195.0 | 146.1 | 23.0 | 53.0 |
| 5. | KKKRT RIARGDNP NGLYG (SEQ ID NO: 131) | 160.2 | 31.7 | 3.7 | 11.5 |
| 6. | SRAGK RRARGDNP NGLYG (SEQ ID NO: 130) | 233.7 | 98.7 | 2.5 | 2.2 |
| 7. | KKKRT RRARGDNP NGLYG (SEQ ID NO: 132) | 153.5 | 44.3 | 3.2 | 1.6 |
| 8. | AKKRT RIARGDNP NGLYG (SEQ ID NO: 138) | 132.2 | 27.6 | 6.9 | 64.0 |
| 9. | KAKRT RIARGDNP NGLYG (SEQ ID NO: 139) | 190.2 | 65.5 | 16.0 | 47.6 |
| 10. | KKART RIARGDNP NGLYG (SEQ ID NO: 140) | 157.5 | 34.2 | 3.5 | 15.5 |
| 11. | KKKAT RIARGDNP NGLYG (SEQ ID NO: 141) | 140.9 | 26.7 | 6.9 | 21.0 |
| 12. | KKKRA RIARGDNP NGLYG (SEQ ID NO: 142) | 192.2 | 78.4 | 19.2 | 58.2 |
| 13. | KAKRA RIARGDNP NGLYG (SEQ ID NO: 143) | 156.6 | 25.0 | 1.9 | 68.4 |
| 14. | SKAGT RIARGDNP NGLYG (SEQ ID NO: 144) | 174.6 | 124.4 | 23.7 | 71.3 |
| 15. | IEEGT RIARGDNP NGLYG (SEQ ID NO: 135) | 206.1 | 401.0 | 15.7 | 50.6 |
| 16. | KGAGK RIARGDNP NGLYG (SEQ ID NO: 136) | 176.0 | 43.8 | 9.8 | 116.1 |
| 17. | LKEGT RIARGDNP NGLYG (SEQ ID NO: 137) | 187.9 | 80.6 | 8.2 | 118.2 |
| 18. | MKKGT RIARGDNP NGLYG (SEQ ID NO: 134) | 178.5 | 151.8 | 4.0 | 113.4 |
| 19. | SRAGK RRARGDNP NGLYG (SEQ ID NO: 130) | 199.8 | 85.0 | 9.6 | 10.9 |

TABLE 8 -continued

Integrin Selectivity and Inhibition of Platelet Aggregation by the Disintegrin Variants with Mutant RGD Loop, Mutant Linker and/or Mutant C-Terminus

| | Consensus Sequence | Platelet Aggregation | αIIbβ3 | αVβ3 | α5β1 |
|---|---|---|---|---|---|
| | | IC$_{50}$ (nM) [Interaction towards targets] | | | |
| 20. | KKKRT RRARGDNP NGLYG (SEQ ID NO: 132) | 147.6 | 31.4 | 3.6 | 2.7 |
| 21. | KKKRT RIARGDNP NGLYG (SEQ ID NO: 131) | 160.2 | 31.7 | 3.7 | 11.5 |

TABLE 9

Integrin Selectivity and Inhibition of Platelet Aggregation by the Disintegrin Variants with Mutant C-Terminus

| Consensus Sequence | αvβ3 | αvβ5 | αvβ6 | α5β1 | αIIbβ3 | Platelet Aggregation |
|---|---|---|---|---|---|---|
| PRGDMP-$^{65}$PRYH (Rho wild type) (SEQ ID NO: 1) | 13.0 | 94.4 | 176.2 | 256.8 | 52.2 | 83.2 |
| 1. PRGDMP-$^{65}$PRWNDL (SEQ ID NO: 102) | 9.8 | 88.5 | 133.7 | 365.9 | 53.7 | 100.9 |
| 2. PRGDMP-$^{65}$PRNRFH (SEQ ID NO: 103) | 15.0 | 162.9 | 140.8 | 590.8 | 81.8 | 107.9 |
| 3. PRGDMP-$^{65}$PRNRFHA (SEQ ID NO: 104) | 26.6 | 712.3 | 192.7 | 309.7 | 290.9 | 154.7 |
| 4. PRGDMP-$^{65}$PRNPWNG (SEQ ID NO: 105) | 40.7 | 681.1 | 160.2 | 260.0 | 235.2 | 121.9 |
| 5. PRGDMP-$^{65}$PRNGLYG (SEQ ID NO: 106) | 26.7 | 258.3 | 282.5 | 238.1 | 186.0 | 96.6 |
| 6. PRGDMP-$^{65}$PGLYG (SEQ ID NO: 107) | 30.1 | 274.8 | 1062.6 | 157.0 | 710.6 | 204.7 |

TABLE 10

Integrin Selectivity and Inhibition of Platelet Aggregation by the Disintegrin Variants

| Consensus Sequence | αvβ3 | αvβ5 | αvβ6 | α5β1 | αIIbβ3 | Platelet Aggregation |
|---|---|---|---|---|---|---|
| $^{39}$SRAGK-$^{46}$RIHRGDMP-$^{65}$PRYH (Rho wild type) (SEQ ID NO: 1) | 13.0 | 94.4 | 176.2 | 256.8 | 52.2 | 83.2 |
| 1. $^{39}$KKART-$^{46}$ARGRGDNP-$^{65}$PGLYG (SEQ ID NO: 124) | 12.0 | 445.3 | 1081.8 | 27.8 | 133335.0 | 35253.2 |

TABLE 10 -continued

Integrin Selectivity and Inhibition of Platelet Aggregation by the Disintegrin Variants

| | Consensus Sequence | $\alpha v\beta 3$ | $\alpha v\beta 5$ | $\alpha v\beta 6$ | $\alpha 5\beta 1$ | $\alpha IIb\beta 3$ | Platelet Aggregation |
|---|---|---|---|---|---|---|---|
| | | \multicolumn{6}{c}{$IC_{50}$ (nM) [Interaction towards targets]} |
| 2. | $^{39}$KKART-$^{46}$ARGRGDNP-$^{65}$P☐LYG (SEQ ID NO: 160) | 7.1 | 410.2 | 245.6 | 35.8 | >95011.0 | 23790.5 |
| 3. | $^{39}$KKART-$^{46}$ARGRGDNP-$^{65}$P☐LYG (SEQ ID NO: 149) | 6.8 | 363.5 | 417.0 | 6.5 | 43085.5 | 5208.5 |
| 4. | $^{39}$KKART-$^{46}$ARGRGDNP-$^{65}$P☐LYG (SEQ ID NO: 120) | 9.5 | 413.8 | 989.9 | 21.6 | >136245.0 | 30285.5 |
| 5. | $^{39}$KKART-$^{46}$ARGRGDNP-$^{65}$P☐LYG (SEQ ID NO: 121) | 13.6 | 720.2 | 986.8 | 15.3 | >338956.0 | 46147.5 |

TABLE 11

Disintegrin Variants Specific to Integrins $\alpha v\beta 3$ and $\alpha 5\beta 1$

| | Consensus Sequence | $\alpha v\beta 3$ | $\alpha v\beta 5$ | $\alpha v\beta 6$ | $\alpha 5\beta 1$ | $\alpha IIb\beta 3$ | Platelet Aggregation |
|---|---|---|---|---|---|---|---|
| | | \multicolumn{6}{c}{$IC_{50}$ (nM) [Interaction towards targets]} |
| | $^{39}$SRAGK-$^{46}$RIPRGDMP-$^{66}$RYH (Rho wild-type) (SEQ ID NO: 1) | 13.0 | 94.4 | 176.2 | 256.8 | 52.2 | 83.2 |
| 1. | $^{39}$KKART-$^{46}$ARGRGDNP-$^{66}$GLYG (SEQ ID NO: 124) | 12.0 | 445.3 | 1081.8 | 27.8 | 133335.0 | 35253.2 |
| 2. | $^{39}$KKART-$^{46}$ARGRGDNP-$^{66}$YLYG (SEQ ID NO: 120) | 11.0 | 413.8 | 1072.7 | 7.5 | 136245.0 | 30285.5 |
| 3. | $^{39}$KKART-$^{46}$ARGRGDNP-$^{66}$ELYG (SEQ ID NO: 121) | 13.6 | 720.2 | 979.4 | 16.9 | 643101.0 | 46147.5 |
| 4. | $^{39}$KKART-$^{46}$ARGRGDNP-$^{66}$DLYG (SEQ ID NO: 147) | 6.6 | 833.7 | 1996.2 | 15.4 | 450958.0 | 84719.0 |

TABLE 12

Disintegrin Variants Specific to Integrins αvβ3, αvβ5, and α5β1

| Consensus Sequence | IC$_{50}$ (nM) [Interaction towards targets] | | | | | |
|---|---|---|---|---|---|---|
| | αvβ3 | αvβ5 | αvβ6 | α5β1 | αIIbβ3 | Platelet Aggregation |
| $^{39}$SRAGK-$^{46}$RIPRGDMP-$^{66}$RYH (Rho wild-type) (SEQ ID NO: 1) | 13.0 | 94.4 | 176.2 | 256.8 | 52.2 | 83.2 |
| 1. $^{39}$SRAGK-$^{46}$RIARGDMP-$^{66}$RYH (SEQ ID NO: 43) | 15.8 | 70.6 | 217.4 | 59.0 | 126.2 | 110.3 |
| 2. $^{39}$SRAGK-$^{46}$RIARGDDP-$^{66}$RYH (SEQ ID NO: 44) | 45.3 | 6886.0 | 14980.5 | 5044.5 | 5117.2 | 752.7 |
| 3. $^{39}$SRAGK-$^{46}$RIARGDDL-$^{66}$RYH (SEQ ID NO: 338) | 41.3 | 226.6 | 15734.5 | 526.7 | 1518.1 | 454.6 |
| 4. $^{39}$KKART-$^{46}$ARGRGDDL-$^{66}$GLYG (SEQ ID NO: 339) | 42.5 | 242.5 | 17323.3 | 562.3 | 44232.2 | 47329.0 |

TABLE 13

Disintegrin Variants Specific to Integrins αvβx and α5β1

| Consensus Sequence | IC$_{50}$ (nM) [Interaction towards targets] | | | | | |
|---|---|---|---|---|---|---|
| | αvβ3 | αvβ5 | αvβ6 | α5β1 | αIIbβ3 | Platelet Aggregation |
| $^{39}$SRAGK-$^{46}$RIPRGDMP-$^{66}$RYH (Rho wild-type) (SEQ ID NO: 1) | 13.0 | 94.4 | 176.2 | 256.8 | 52.2 | 83.2 |
| 1. $^{39}$SRAGK-$^{46}$RIARLDDL-$^{66}$RYH (SEQ ID NO: 125) | 42.0 | 941.4 | 20683.3 | 14539.0 | 23171.0 | 10380.0 |
| 2. $^{39}$SRAGK-$^{46}$DDPRGDMP-$^{66}$RYH (SEQ ID NO: 126) | 25.1 | 500.0 | 1251.5 | 8653.0 | >44540.0 | 18922.3 |
| 3. $^{39}$KKART-$^{46}$ARGRGDNP-$^{66}$RYH (KG, AR-NP) (SEQ ID NO: 123) | 5.0 | 445.7 | 317.0 | 28.8 | 37925.0 | 4478.3 |
| 4. $^{39}$KKART-$^{46}$ARGRGDNP-$^{66}$GLYG (KG-P) (SEQ ID NO: 124) | 12.0 | 445.3 | 1081.8 | 27.8 | 133335.0 | 35253.2 |
| 5. $^{39}$KKART-$^{46}$ARGRGDNP-$^{66}$RWNDL (KG-WN) (SEQ ID NO: 171) | 1.8 | 43.7 | 108 | 25.6 | 27985 | 4533 |

TABLE 14

Integrin Selectivity and Inhibition of Platelet Aggregation by Varying One or More of the Linker, RGD Loop and the C-Terminus

| Consensus Sequence of Disintegrin Variant | IC$_{50}$ (nM) [Interaction towards targets] | | | Platelet Aggregation |
|---|---|---|---|---|
| | α5β1 | αVβ3 | αIIbβ3 | |
| 1. -----$^{48}$ARGD$^{65}$PR (SEQ ID NO: 115) | 3636.5 | 479.6 | 1588.3 | 107.1 |
| 2. -----$^{48}$ARGD$^{65}$PRNGL (SEQ ID NO: 348) | 5161.0 | 146.0 | 1086.3 | 69.9 |
| 3. -----$^{48}$ARGD$^{65}$PRNGLYG (SEQ ID NO: 119) | 9529.3 | 1191.8 | 245.2 | 83.4 |
| 4. -----$^{48}$ARGD$^{65}$PRNPWNG (SEQ ID NO: 118) | 2679.0 | 1259.0 | 184.7 | 132.7 |
| 5. $^{39}$KKKRT-$^{48}$ARGDN$^{53}$P-$^{67}$NGLY$^{71}$G (SEQ ID NO: 131) | 11.5 ± 1.3 | 3.7 ± 0.9 | 31.7 ± 4.7 | 160.2 ± 16.9 |
| 6. $^{39}$MKKGT-$^{48}$ARGDN$^{53}$P-$^{67}$NGLY$^{71}$G (SEQ ID NO: 349) | 113.4 ± 2.3 | 4.0 ± 0.8 | 151.8 ± 23.7 | 178.5 ± 10.3 |
| 7. $^{39}$IEEGT-$^{48}$ARGDN$^{53}$P-$^{67}$NGLY$^{71}$G (SEQ ID NO: 135) | 50.6 ± 5.0 | 15.7 ± 2.2 | 401.0 ± 77.9 | 206.1 ± 17.9 |
| 8. $^{39}$SRAGK-$^{48}$ARGDN$^{53}$P-$^{67}$NGLY$^{71}$G (SEQ ID NO: 347) | 53.0 ± 7.8 | 23.0 ± 7.1 | 146.1 ± 30.9 | 195.0 ± 45.7 |
| 9. $^{39}$KGAGK-$^{48}$ARGDN$^{53}$P-$^{67}$NGLY$^{71}$G (SEQ ID NO: 136) | 116.1 ± 19.9 | 9.8 ± 1.8 | 43.8 ± 3.5 | 176.0 ± 35.9 |
| 10. $^{39}$LKEGT-$^{48}$ARGDN$^{53}$P-$^{67}$NGLY$^{71}$G (SEQ ID NO: 137) | 118.2 ± 6.2 | 8.2 ± 0.5 | 80.6 ± 2.5 | 187.9 ± 25.7 |
| 11. $^{39}$AKKR$^{34}$T-$^{48}$ARGDN$^{53}$P-$^{67}$NGLY$^{71}$G (SEQ ID NO: 138) | 64.0 ± 3.9 | 6.9 ± 1.0 | 27.6 ± 6.5 | 132.2 ± 27.1 |
| 12. K$^{40}$AKR$^{43}$T-$^{48}$ARGDN$^{53}$P-$^{67}$NGLY$^{71}$G (SEQ ID NO: 139) | 47.6 ± 9.5 | 16.0 ± 2.4 | 65.5 ± 3.5 | 190.2 ± 16.5 |
| 13. KK$^{41}$AR$^{43}$T-$^{48}$ARGDN$^{53}$P-$^{67}$NGLY$^{71}$G (SEQ ID NO: 140) | 15.5 ± 3.2 | 3.5 ± 0.4 | 34.2 ± 5.3 | 157.5 ± 10. |
| 14. KKK$^{42}$A$^{43}$T-$^{48}$ARGDN$^{53}$P-$^{67}$NGLY$^{71}$G (SEQ ID NO: 141) | 21.0 ± 2.2 | 6.9 ± 1.3 | 26.7 ± 4.7 | 140.9 ± 10.6 |
| 15. KKKR$^{43}$A-$^{48}$ARGDN$^{53}$P-$^{67}$NGLY$^{71}$G (SEQ ID NO: 142) | 58.2 ± 6.7 | 19.2 ± 1.2 | 78.4 ± 11.5 | 192.2 ± 6.9 |
| 16. $^{39}$KAKRA$^{43}$-$^{48}$ARGDN$^{53}$P-$^{67}$NGLY$^{71}$G (SEQ ID NO: 143) | 68.4 | 1.9 | 25.0 ± 4.4 | 156.6 ± 28.2 |
| 17. $^{39}$SKAGT$^{43}$-$^{48}$ARGDN$^{53}$P-$^{67}$NGLY$^{71}$G (SEQ ID NO: 144) | 71.3 | 23.7 | 124.4 ± 0.9 | 174.6 ± 23.7 |
| 18. $^{39}$SRAGKICR-$^{47}$RARGDN$^{53}$P-$^{67}$NGLY$^{71}$G (SEQ ID NO: 130) | 2.2 | 2.5 | 98.7 ± 9.1 | 233.7 ± 22.3 |
| 19. $^{39}$KKKRTICR-$^{47}$RARGDN$^{53}$P-$^{67}$NGLY$^{71}$G (SEQ ID NO: 132) | 1.6 | 3.2 | 44.3 ± 10.1 | 153.5 ± 5.4 |
| 20. $^{9}$KKKRT-$^{46}$ARARGDN$^{53}$P-$^{67}$NGLY$^{71}$G (SEQ ID NO: 169) | 2.7 | 3.6 | 31.4 | 147.6 |
| 21. $^{39}$KKKR$^{43}$T-$^{48}$PRGDM$^{53}$P-$^{67}$Y$^{68}$H (SEQ ID NO: 127) | 76.1 ± 22.3 (3) | 1.3 ± 0.2 (2) | 25.6 ± 7.0 (3) | 104.5 ± 23.0 |
| 22. $^{39}$SRAG$^{43}$K-$^{48}$ARGDN$^{53}$P-$^{67}$Y$^{68}$H (SEQ ID NO: 128) | 40.0 ± 5.8 (2) | 22.6 ± 3.7 (2) | 256.0 ± 8.5 (2) | 125.4 ± 25.4 |
| 23. $^{39}$KKKR$^{43}$T-$^{48}$ARGDN$^{53}$P-$^{67}$Y$^{68}$H (SEQ ID NO: 166) | 10.0 ± 2.4 (3) | 5.9 ± 1.0 (3) | 133.4 ± 15.1 (3) | 88.2 ± 17.2 |

Example 5

Inhibition of Cell Migration by Disintegrin Variant and Wild Type of Rhodostomin Transwell filters were equilibrated in serum containing DMEM for 2 h before use. DMEM containing 10% FBS was added to the lower compartments of the migration filters. In a volume of 100 ml serum-free DMEM, $2\times10^4$ A375 human melanoma cells were plated per transwell filter. Cells were allowed to migrate for 6 h at 37° C. in 5% $CO_2$, and were subsequently fixed by immersion of the filters in methanol for 15 min at room temperature. Rhodostomin, AR-NP (see Table 13 for consensus sequence), or PBS buffer were added into upper chamber. Filters were washed once with water, and were stained in 0.2% crystal violet in a 20% methanol/water solution for 10 min. Cells were removed from the upper surface of the membrane with a cotton swab. Cells that had migrated to the underside of the membrane were counted at 200× magnification from five random fields per membrane.

Figure 2A:
FIGS. 2A, 2B, and 2C show the inhibitory activity of various tested agents on the migration of A375 human melanoma cells.
Figure 2B:
Figure 2C:
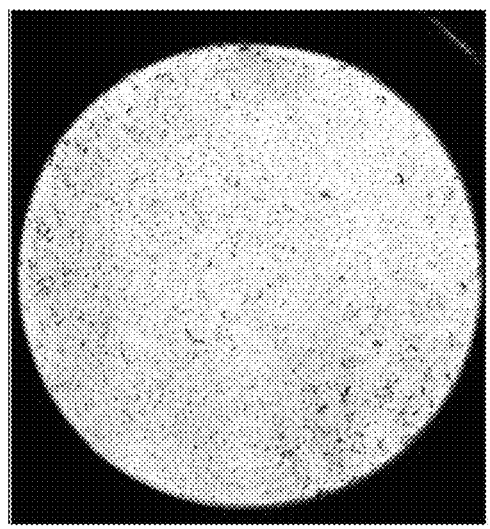

The inhibitory activity of Rho, AR-NP, or PBS buffer in this study as shown in FIGS. 2A, 2B, and 2C. Briefly, AR-NP markedly inhibited the migration of A375 human melanoma cells.

Example 6

Inhibition of Angiogenesis by Disintegrin Variants in Matrigel Angiogenesis Assay The matrigel containing VEGF (100 ng/ml) and heparin (24-26 U/ml) is subcutaneously injected into B6 mice. After 5 days the gels are recovered, weighed and processed for hemoglobin quantification or histology as previously described. Hemoglobin content is measured with a Drabkin reagent kit 525 (Sigma). For histological analyses, the matrigel pellets are fixed in 4% paraformaldehyde and embedded in paraffin; four micron sections are stained with hematoxylin-eosin by standard procedures.

Figure 3A:
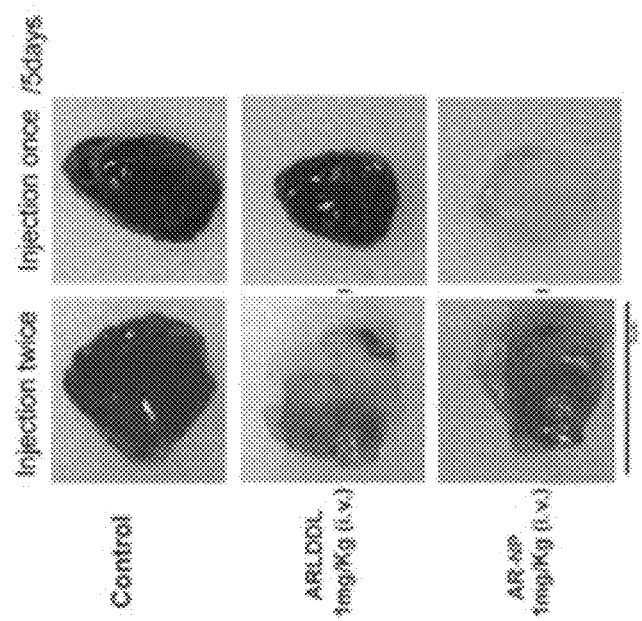
FIG. 3A are photographs showing a reduced blood vessel density in MATRIGEL™ plugs from C57BL/6 mice treated with AR-NP protein or ARLDDL protein (SEQ ID NO: 351), in comparison with untreated control mice.
Figure 3C:
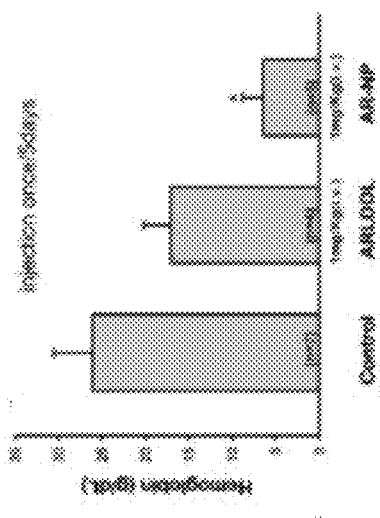
FIG. 3C is a graph showing a reduced hemoglobin content in MATRIGEL™ plugs from C57BL/6 mice treated with AR-NP protein or ARLDDL protein (SEQ ID NO: 351) administrated once daily for 5 days in comparison with untreated control mice.
Figure 3B:
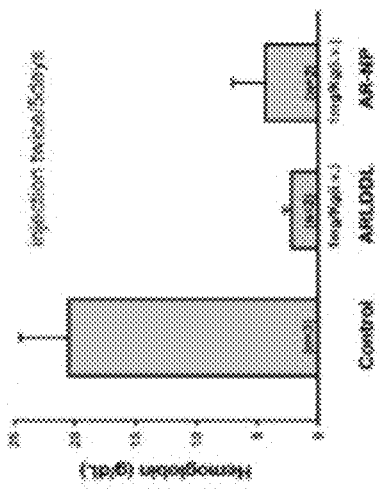
FIG. 3B is a graph showing a reduced hemoglobin content in MATRIGEL™ plugs from C57BL/6 mice treated with AR-NP protein or ARLDDL protein (SEQ ID NO: 351) twice daily after 5 days in comparison with untreated control mice.

An aliquot (300 μL) of MATRIGEL™ (Becton Dickinson Lab.) containing VEGF (150 ng) and heparin (30 IU) was injected subcutaneously into the dorsal region of 6-8 week-old C57BL/6 mice. The MATRIGEL™ formed a plug rapidly. AR-NP (1 mg/kg) or ARLDDL (SEQ ID NO: 351) (1 mg/kg) (see Table 13 for consensus sequence) was administered once intravenously 24 hr later. After 5 days, plugs were taken and photographed (upper panel). Neovessels were quantified by measuring the hemoglobin of the plugs as an indication of blood vessel formation with the Drabkin method and Drabkin reagent kit 525 (Sigma) (B&C). The analysis showed that AR-NP was more effective than ARLDDL (SEQ ID NO: 351) when the drug was injected only once during 5 days angiogenesis period. See FIGS. 3A, 3B, and 3C.

Example 7

Inhibition of Angiogenesis by Hyperoxia/Normoxia-Driven Model of Retinopathy of Prematurity (ROP)

One-week-old C57BL/6j mice or ICR mice and their mothers are exposed to 75%±2% oxygen for 5 days (hyperoxia) and then returned to normoxic conditions for another 5 day (hyperoxic period, P7 to P12) for inducing relative hypoxic conditions, and were then housed in room air for a further 7 days (hypoxic-induced angiogenic period, P12 to P19). AR-NP (1 pg) was administered via intravitreous route on Day 12 and the mice were sacrificed on Day-19. Unexposed control animals are kept in room air. The animals are maintained at a constant temperature of 21±1° C. and on a 12-hour light-dark cycle. Oxygen concentration is measured with an oximeter. At the end of the oxygen exposure (day 12) and 5 days after return to normoxic conditions (day 17), the pups are killed, and retinal angiogenesis is evaluated by neovessels and endothelial cells.

Figure 4A:
FIG. 4A are photographs showing angiogenesis in a mouse model of retinopathy of prematurity (ROP), and reduced angiogenesis in a ROP mouse treated with AR-NP protein, arrows indicate blood vessel profiles (BVPs) of new vessels.
Figure 4B:
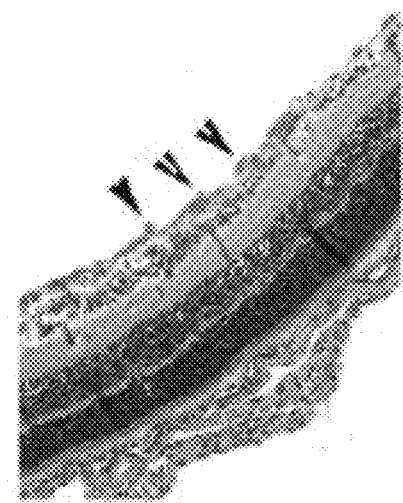
FIG. 4B is a graph showing reduced BVPs of the new vessels in a mouse model of retinopathy of prematurity (ROP) treated with AR-NP protein.
Figure 4B:
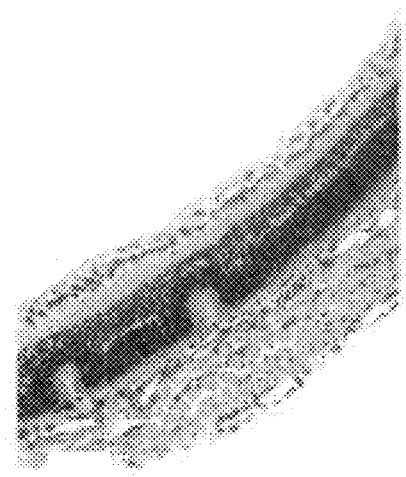
Figure 4B:
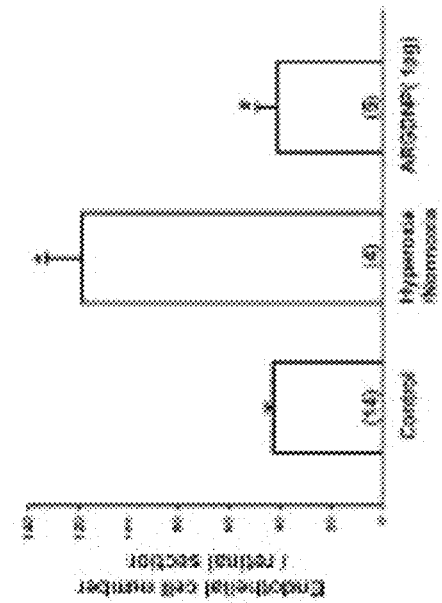
Figure 4C:
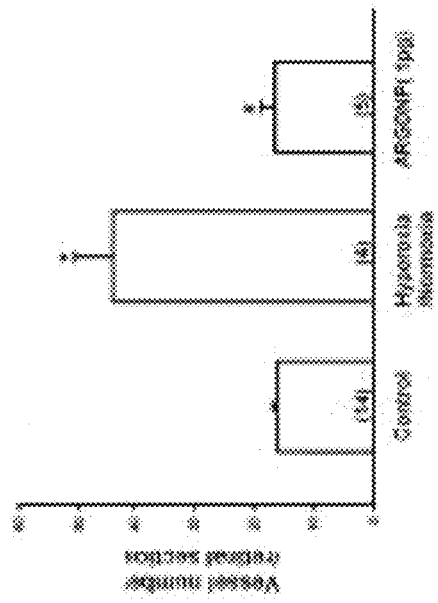
FIG. 4C is a graph showing reduced BVPs of the endothelial cells in a mouse model of retinopathy of prematurity (ROP) treated with AR-NP protein.

The results of this study were shown in FIGS. 4A, 4B, and 4C. The analysis showed that AR-NP significantly reduced angiogenesis in a mouse model of retinopathy.

Example 8

Inhibition of Angiogenesis by Disintegrin Variants in Mice Aortic Ring Assays The thoracic aortas of mice 8-12 weeks of age are dissected out and cut into rings approximately 0.5 mm in width. The aortic rings are mounted in 200 ml matrigel covered with DMEM supplemented with 2.5% FCS and 30 ng/ml VEGF with or without the appropriate inhibitors or control agents. The experiment was conducted in $CO_2$ incubator at 37° C. After 7 d in culture, the aortic rings are fixed with 4% formaldehyde and stained them with crystal violet. The number of sprouts grown from each ring by using inverted microscope was counted.

Figure 5:
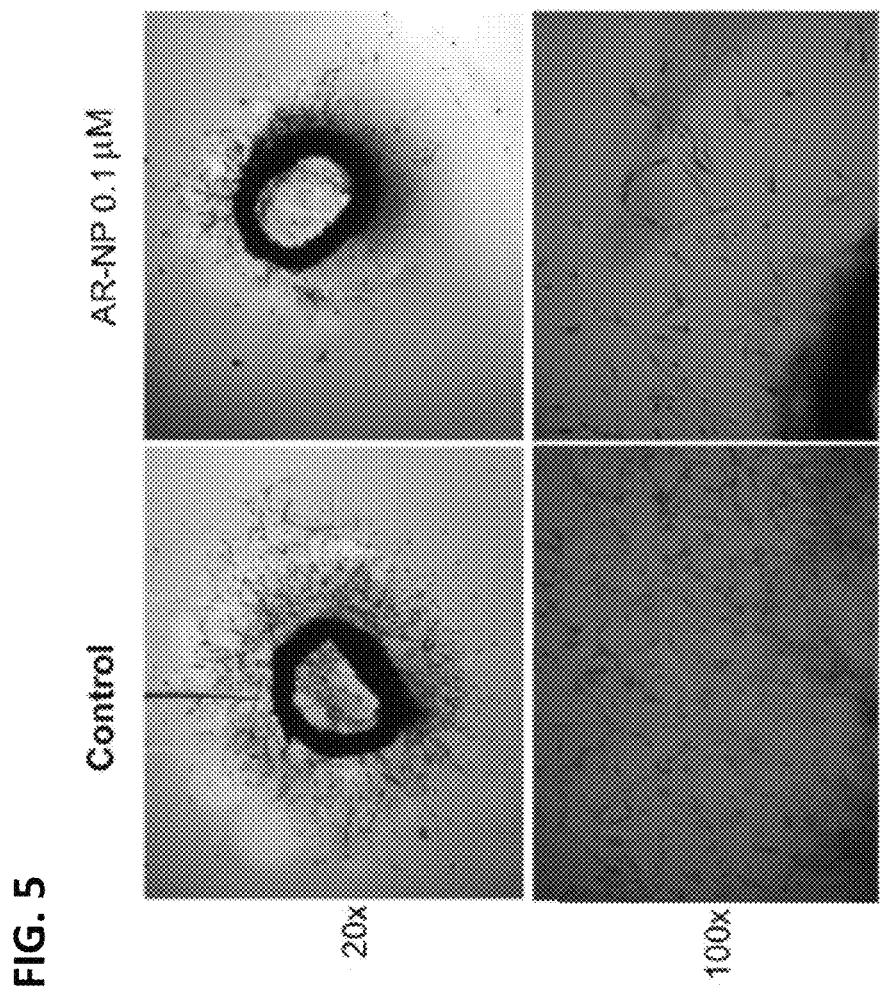
FIG. 5 shows the inhibition of mice aortic ring by AR-NP protein (0.1 µM) for 7 days in comparison with untreated control: upper panel: images taken at magnification ×20; Lower panel: image taken at magnification ×100.

Mouse aortic rings were incubated with VEGF and 0.1 μM AR-NP in matrigel containing 100 mg/ml of fibronectin. The culture medium was changed every 3 days. Graphs showed the microvessel sprouting after 7 days culture. Note that AR-NP significantly reduced the vessel sprouting (see FIG. 5).

Example 9

Figure 6:
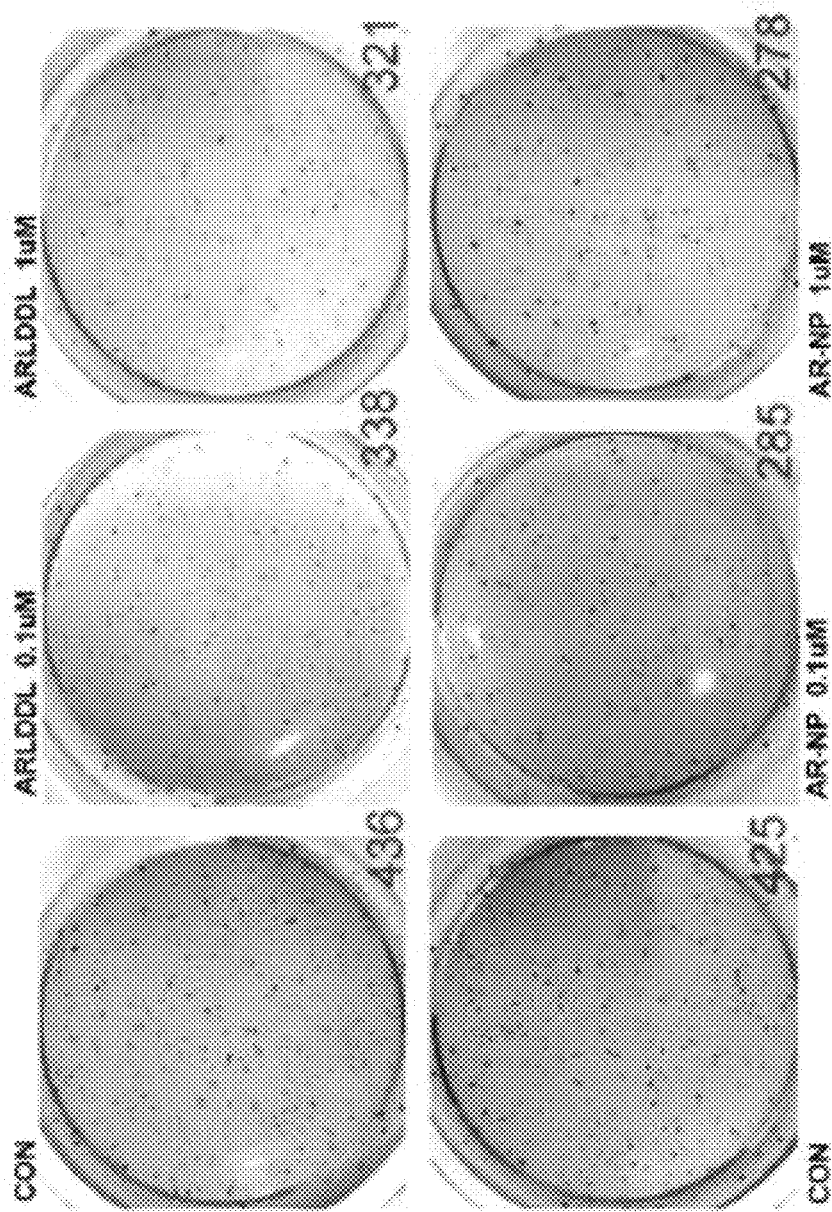
FIG. 6 shows that both ARLDDL (SEQ ID NO: 351) (0.1 µM & 1 µM) and AR-NP (0.1 µM & 1 µM) inhibited colony formation of 4-T1 breast cancer cells.
Figure 7B:
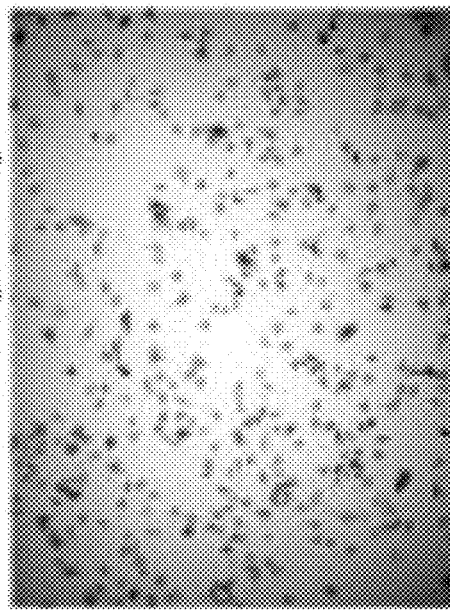
FIGS. 7A, 7B, 7C, and 7D show that AR-NP protein or ARLDDL protein inhibited RANKL-induced osteoclastogenesis in comparison with untreated control: AR-NP protein (FIGS. 7B and 7C); ARLDDL protein (SEQ ID NO: 351) (FIG. 7D); control (FIG. 7A)
Figure 7A:
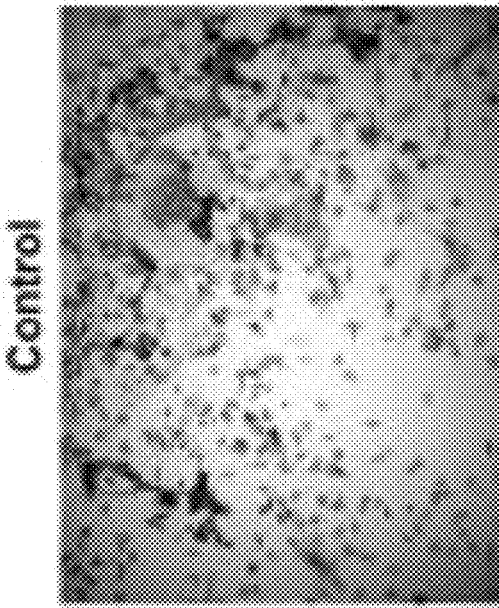
Figure 7D:
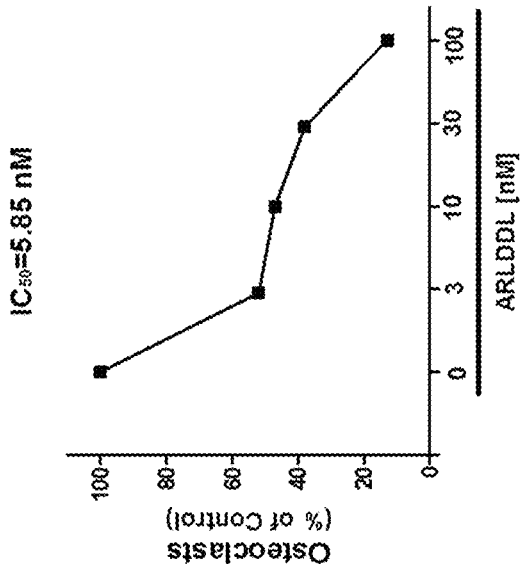
Figure 7C:
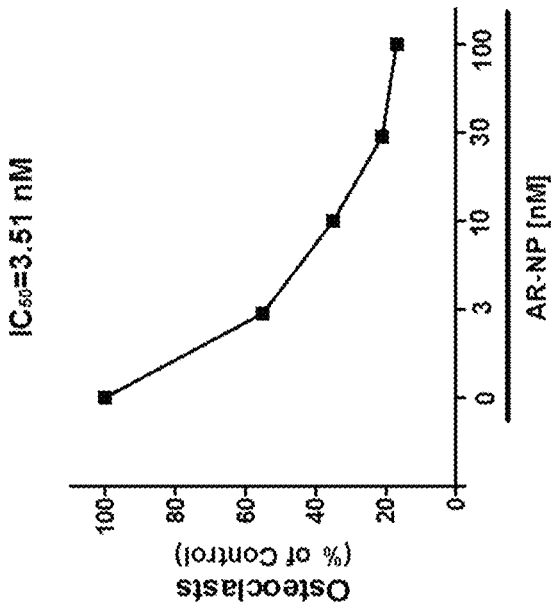

Inhibition of Colony Formation by Disintegrin Variants on Breast Cancer Cells The representative images in FIG. 6 showed the results of colony formation assay. 4-T1 breast cancer cells were plated in 6-well dishes with a top layer of 0.35% agar and a bottom layer of 0.7% agar in medium. 0.3 mL of medium is supplemented every 3 days. After 18 days, the number of cell clusters per dish is identified by crystal violet staining and counted. The analysis showed that both ARLDDL (SEQ ID NO: 351) (0.1 μM & 1 μM) and AR-NP (0.1 μM & 1 μM) inhibited colony formation of 4-T1 breast cancer cells.

Example 10

Inhibition of Osteoclastogenesis by Disintegrin Variants

Six- to eight-week-old SD rats are obtained from the Animal Center of National Laboratory and are kept under controlled conditions including a 22±1° C. room temperature and a 12-h light-dark cycle. Animals are fed with Purina Laboratory Rodent Diet and distilled water ad libitum. Bone marrow cells are prepared by removing from femurs and tibiae and flushing the bone marrow cavity with DMEM (Invitrogen, Carlsbad, Calif.) which is supplemented with 20 mM HEPES and 10% heat-inactivated FBS, 2 mM glutamine, penicillin (100 U/ml) and streptomycin (100 g/ml). The non-adherent cells (hematopoietic cells) are collected after 24 hr and used as osteoclast precursors. Cells are seeded at 1×10⁶ cells/well in 24-well plates in the presence of human recombinant soluble RANKL (50 ng/ml) and M-CSF (20 ng/ml). The culture medium is replaced every 3 days. Osteoclast formation is measured on Day-8 by TRAP staining. In brief, adherent cells are fixed with 10% formaldehyde in PBS for 3 min and then stained with Naphthol AS-MX phosphate and tartrate solution for 1 hr at 37° C. Osteoclast-like cells in each well are scored by counting the number of TRAP-positive and multinucleated cells containing more than three nuclei.

The protein drugs were added on D1~D7. IC50 of osteoclastogenesis for α5β1 and αvβ3 dual integrin AR-NP is 3.61 nM. As shown in FIGS. 7A-7D, AR-NP protein or ARLDDL protein (SEQ ID NO: 351) inhibited RANKL-induced osteoclastogenesis in comparison with untreated control.

Example 11

Inhibition of Glioma Invasion by Disintegrin

Figure 8:
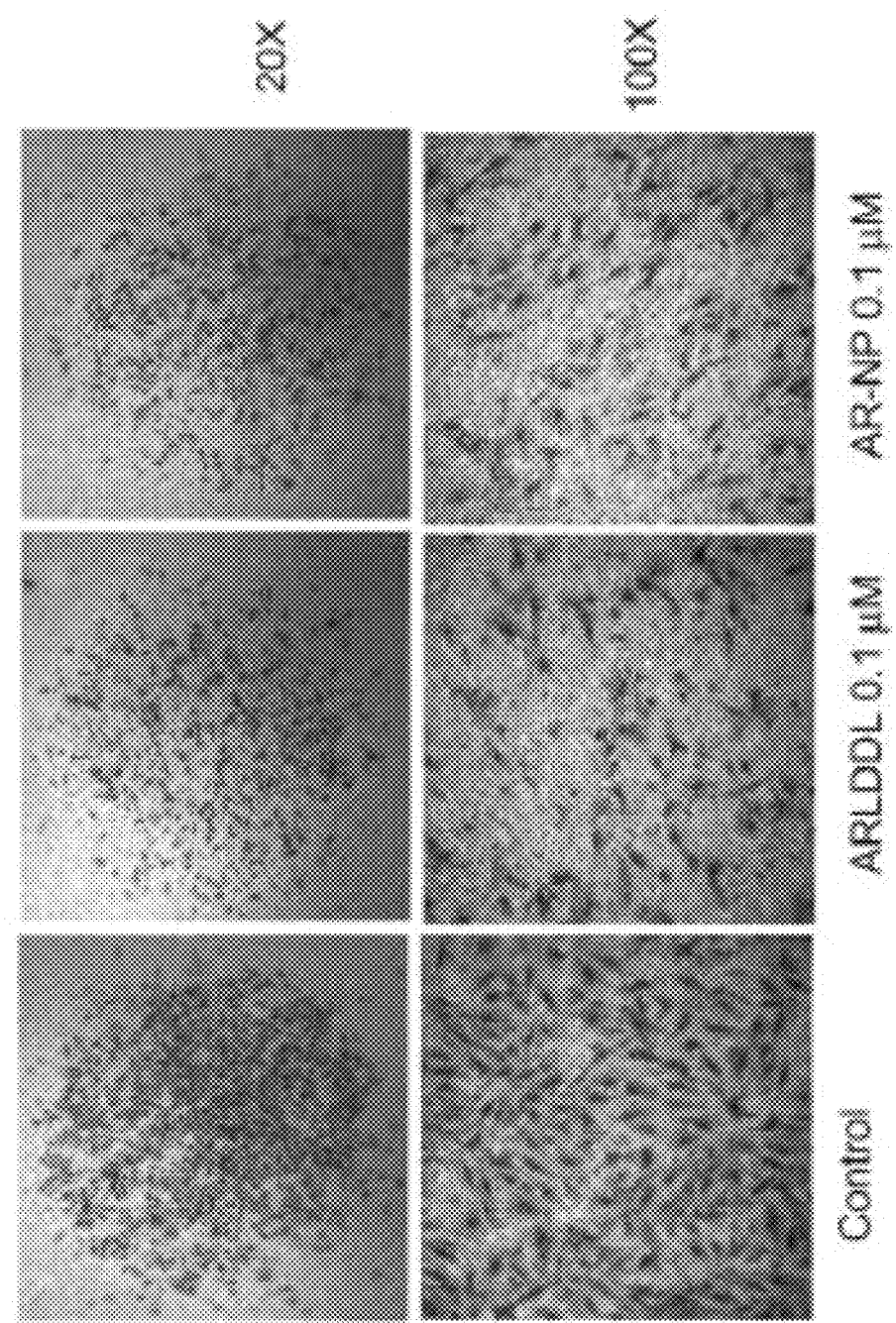
FIG. 8 shows that both ARLDDL (SEQ ID NO: 351) (0.1 µM) and AR-NP (0.1 µM) markedly inhibited glioma invasion.

Human glioma cells (U251) were cultured in upper chamber with matrigel containing 100 g/ml hyaluronan. Disintegrin variant was added in both upper and lower chambers. 24 hours later, the cells in the lower chamber were stained using crestal violet and counted. As shown in FIG. 8, both ARLDDL (SEQ ID NO: 351) (0.1 µM) and AR-NP (0.1 µM) markedly inhibited glioma invasion.

Example 12

Effect of AR-NP on Blood Pressure and Heart Rate

Figure 9A:
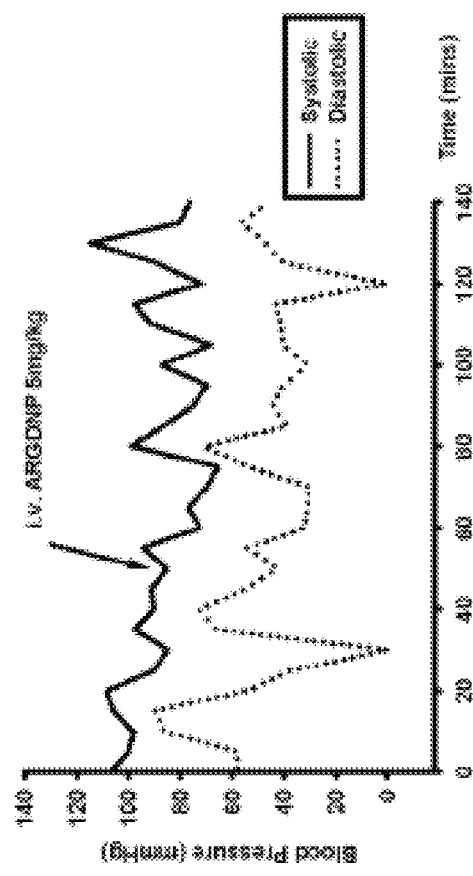
FIGS. 9A and 9B show that AR-NP at 5 mg/kg did not significantly affect blood pressure and heart rate in Wistar rat.
Figure 9B:
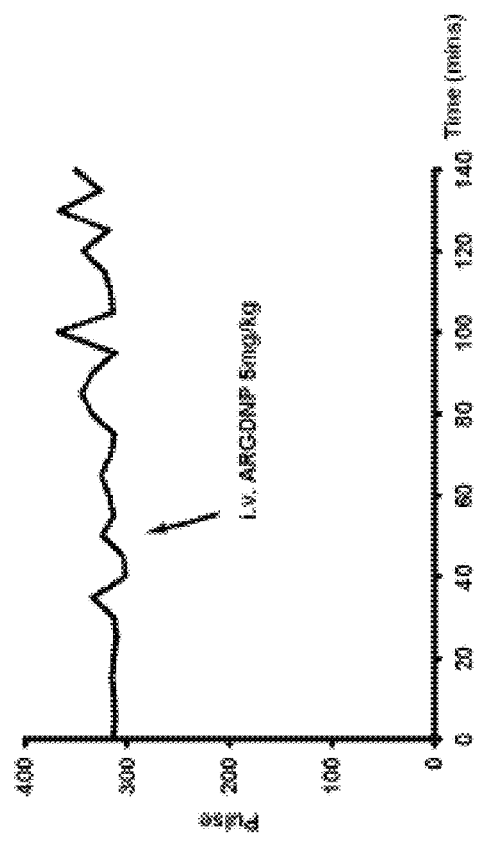

Blood pressure and heart rate were recorded from tail using non-invasive method under isoflurane anesthesia in Wistar rat. AR-NP was administered from tail vein after getting a stable measurement. Note that AR-NP at 5 mg/kg did not significantly affect blood pressure and heart rate (FIGS. 9A and 9B). The usual dose of AR-NP for pharmacological effect is 1 mg/kg.

Example 13

Inhibition of A375 Melanoma Growth by AR-NP

Figure 10:
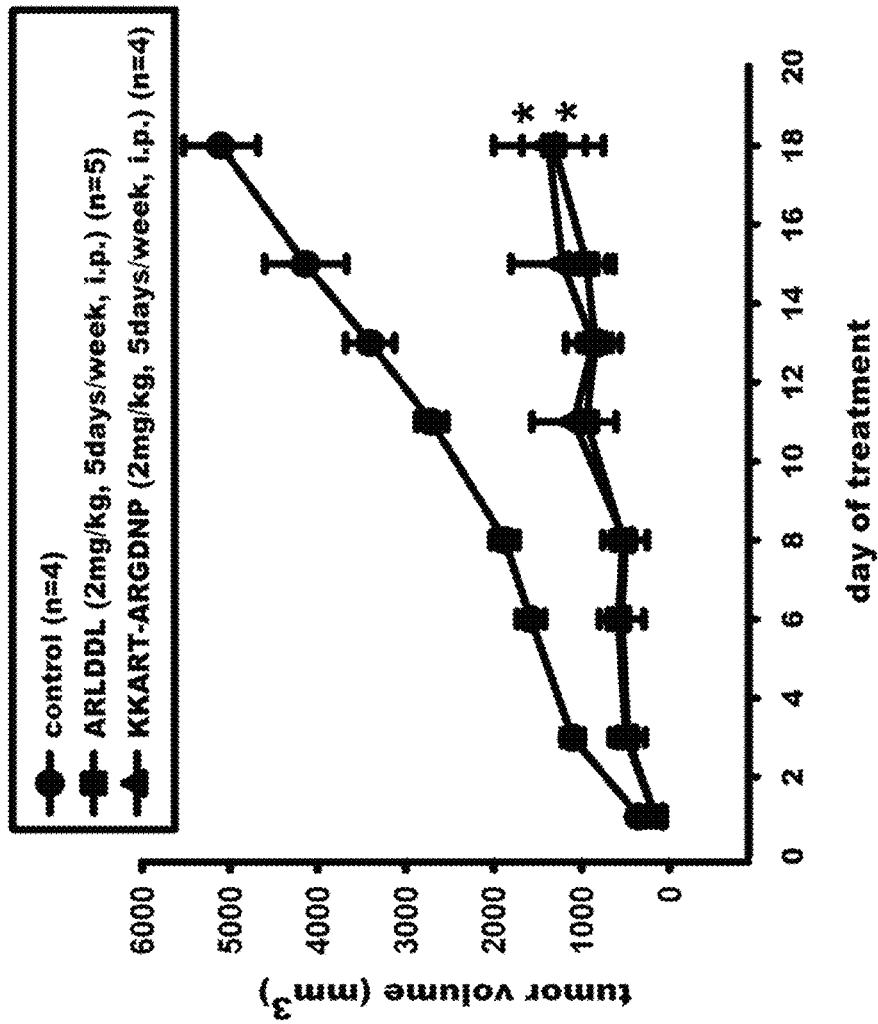
FIG. 10 shows the inhibition of A375 melanoma growth by AR-NP in SCID mice, scale bar: 1 cm.

A375 tumor cells (at 5×10⁶) were injected subcutaneously in the flank of 4-5 week-old male SCID mice. One week after cell implantation, mice were injected with AR-NP (KKART-ARGRGDNP; SEQ ID NO: 350) (2 mg/kg, 5 days/week, i.p.). Tumor volume was measured every two days. Tumors were excised and weighed after 18 days of drug treatment. Scale bar: 1 cm. Note that AR-NP treatment markedly inhibited tumor growth (see FIG. 10).

Example 14

Inhibition of Tumor Growth by KG (AR-NP) in K-rasG12D Transgenic Mice

Figure 11:
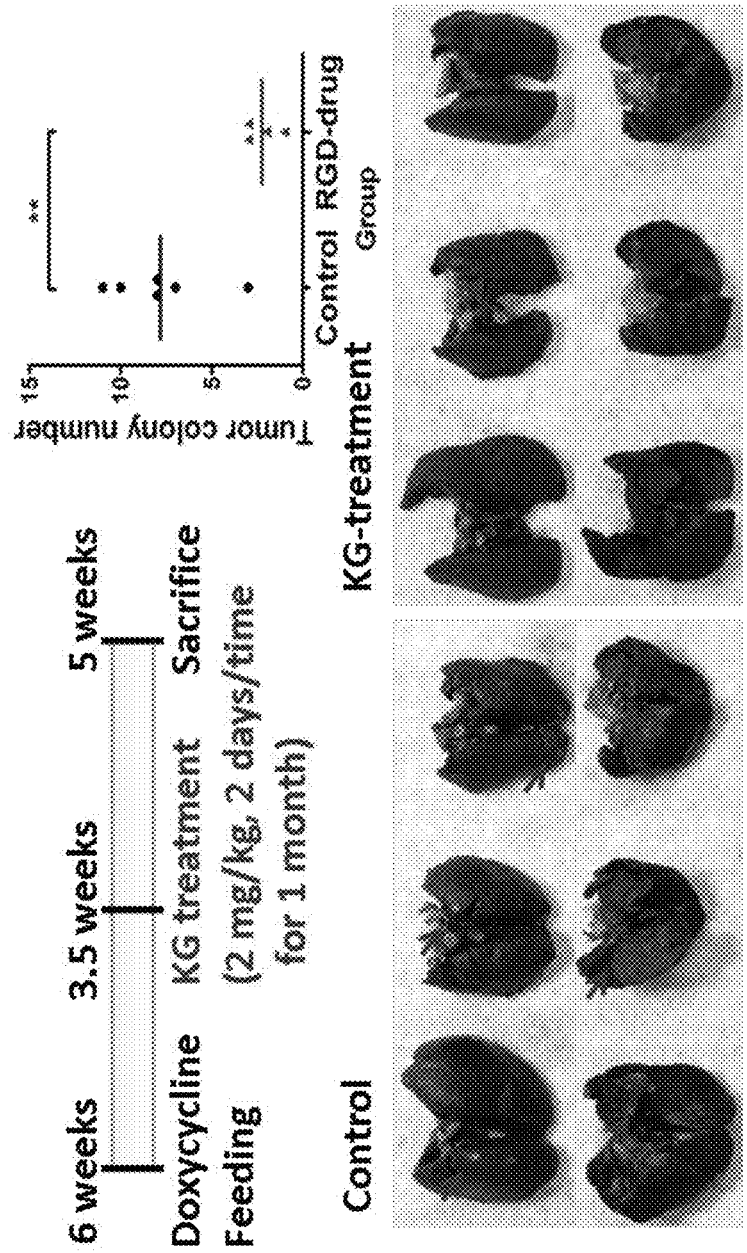
FIG. 11 shows the inhibition of tumor growth by AR-NP (KG) in K-rasG12D transgenic mice.

K-Ras$^{G12D}$ transgenic mice was fed with 400 mg/L doxycycline to induce lung cancer. After 3.5 months, TG mice were intraperitoneally (IP) injected with 2 mg/kg of AR-NP at two days interval for one month. Two weeks after fifteenth treatment, mice were sacrificed. Lungs were injected with India ink and fixated in Fekete's solution. The number of tumor nodules on lung were counted. , P value<0.001. As shown in FIG. 11**, the disintegrin variant (AR-NP) inhibited tumor growth in K-rasG12D transgenic mice.

Example 15

Inhibition of Brain Tumor Growth in U87-Bearing Mice by KG

NOD-SCID mice were originally purchased and bred/maintained in a specific-pathogen-free vivarium with a well-controlled environment with a 12-h/12-h light/dark cycle and controlled humidity and temperature. 8-10 week-old mice weighing approximately 22-25 g were used. The mice were intraperitoneally anesthetized with a mixture of Dexdomitor/Zoletil (20 m/kg/2 mg/kg), then placed in a stereotactic frame, and the skull was exposed by incision. U87-MG cells were harvested and adjusted to a density of 2.5×10⁵ cells/µL in phosphate buffered saline (PBS) before intracranial injection. 2 µL of U87-MG cells were injected into the striatum at the designated coordinates from the Bregma using a micro-infusion pump and 10-ml Hamilton syringe with a 30 S-gage needle. The skull was then cleaned, the hole was sealed with bone wax, and the incision was sutured.

Figure 12:
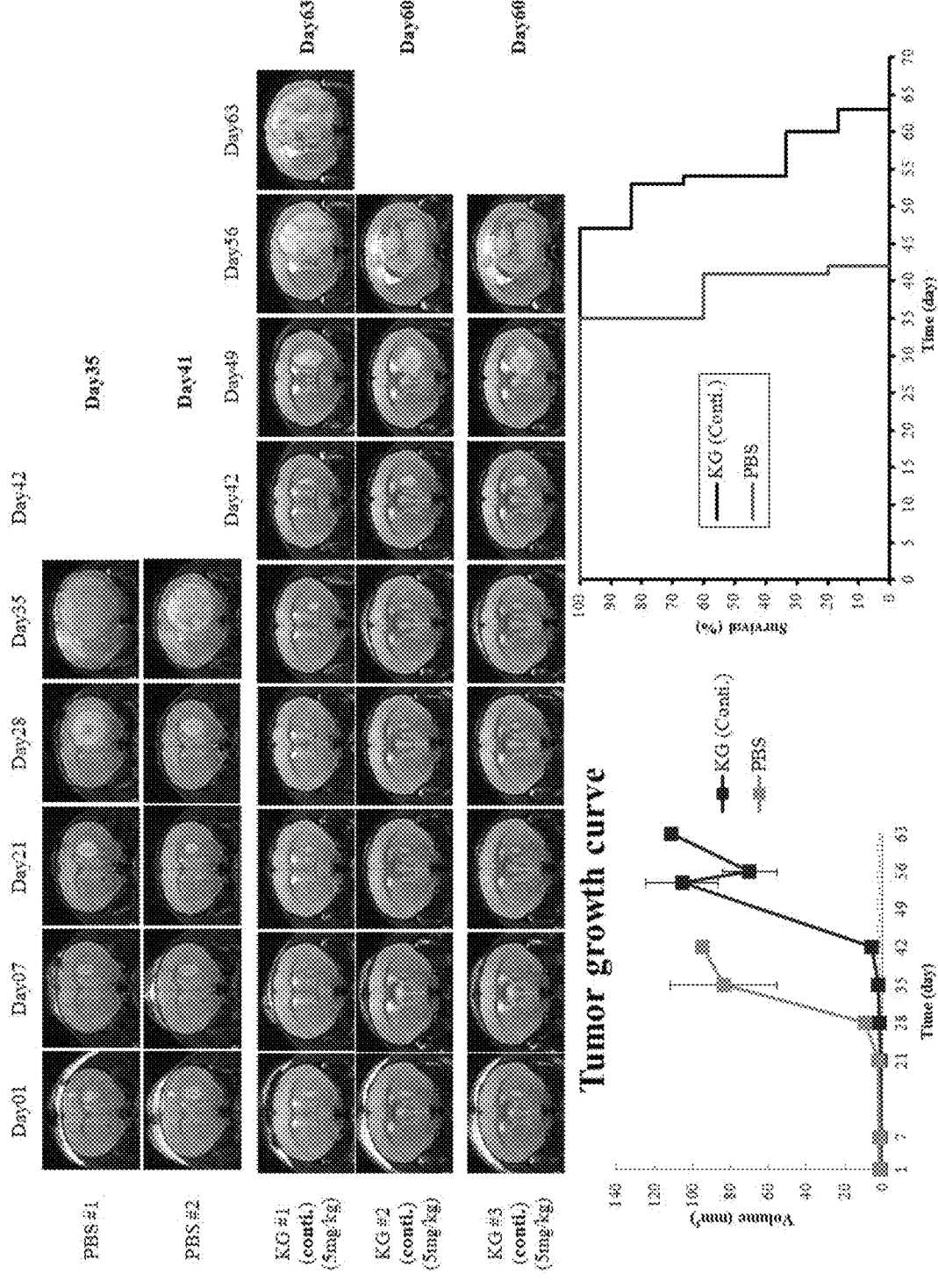
FIG. 12 shows the inhibition of brain tumor growth in U87-bearing mice by AR-NP (KG).

MRI was performed in a horizontal 7.0-T spectrometer with an active shielding gradient of 300 mT/m in 80 µs. The outlines of the tumors were delineated based on the contrast provided by the T2WIs between the tumor and the brain tissues. The total tumor volume (mm³) was calculated by summing the tumor area across the slices covered by tumor using MR Vision software. Growth curves were plotted as the change in tumor volume at each time point. Starting from day 23 after tumor implantation, the mice were treated intravenously via tail vein with the disintegrin variant (AR-NP) only or a mixture at 5 mg/kg once a day, five days a week. As shown by the results in FIG. 12, the disintegrin variant (AR-NP) also inhibited tumor growth in U87-bearing mice.

While the invention has been described in detail, and with reference to specific embodiments thereof, it will be apparent to one of ordinary skill in the art that various changes and modifications can be made therein without departing from the spirit and scope thereof.

The invention claimed is:

1. A polynucleotide encoding a disintegrin variant of rhodostomin comprising the amino acid sequence of SEQ ID NO: 1, wherein the disintegrin variant comprises:
- a mutant RGD loop, wherein the amino acid sequence at positions 46 to 53 of SEQ ID NO: 1 is substituted with an amino acid sequence selected from the group consisting of SEQ ID NOs: 329, 330, 331, 353, and 354, and
- at least one selected from the group consisting of:
  - (a) a mutant linker, wherein the amino acid sequence at positions 39 to 45 of SEQ ID NO: 1 is substituted with an amino acid sequence selected from the group consisting of SEQ ID NO: 306 to SEQ ID NO: 318; and
  - (b) a mutant C-terminus, wherein the amino acid sequence at positions 65 to 68 of SEQ ID NO: 1 is substituted with an amino acid sequence selected from the group consisting of SEQ ID NOs: 319, 323, 324, 326, 327, 328, 337, and 352,
- wherein the disintegrin variant has an increased selectivity for at least one of αvβ1, αvβ3, αvβ5, αvβ6, αvβ8 and α5β1 integrins over αIIbβ3 integrin as compared to wild-type rhodostomin having the amino acid sequence of SEQ ID NO: 1.

2. The polynucleotide of claim 1, wherein the disintegrin variant comprises the mutant RGD loop, the mutant linker and the mutant C-terminus.

3. The polynucleotide of claim 1, wherein the disintegrin variant comprises a mutant RGD loop of SEQ ID NO: 331 and a mutant linker of SEQ ID NO: 313.

4. The polynucleotide of claim 1, wherein the disintegrin variant comprises the amino acid sequence selected from the group consisting of SEQ ID NOs: 120, 121, 123, 124, 129-144, 147, 149, 160, 166, 169, 171, 339, 347, and 349.

5. The polynucleotide of claim 1, wherein the disintegrin variant comprises the amino acid sequence selected from the group consisting of SEQ ID NOs: 123, 124, 147, 149 and 171.

6. The polynucleotide of claim 1, wherein the disintegrin variant is conjugated with albumin or Fc.

7. A recombinant host cell comprising the polynucleotide of claim 1.

8. The polynucleotide of claim 1, wherein the disintegrin variant is further pegylated.

* * * * *

SEQUENCE LISTING

<160> NUMBER OF SEQ ID NOS: 354

<210> SEQ ID NO 1
<211> LENGTH: 68
<212> TYPE: PRT
<213> ORGANISM: Calloselasma rhodostoma
<220> FEATURE:
<221> NAME/KEY: PEPTIDE
<222> LOCATION: (1)..(68)

<400> SEQUENCE: 1

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 2
<211> LENGTH: 70
<212> TYPE: PRT
<213> ORGANISM: Trimeresurus flavoviridis
<220> FEATURE:
<221> NAME/KEY: PEPTIDE
<222> LOCATION: (1)..(70)

<400> SEQUENCE: 2

Gly Glu Glu Cys Asp Cys Gly Ser Pro Ser Asn Pro Cys Cys Asp Ala
1               5                   10                  15

Ala Thr Cys Lys Leu Arg Pro Gly Ala Gln Cys Ala Asp Gly Leu Cys
            20                  25                  30

Cys Asp Gln Cys Arg Phe Lys Lys Lys Arg Thr Ile Cys Arg Ile Ala
        35                  40                  45

Arg Gly Asp Phe Pro Asp Asp Arg Cys Thr Gly Gln Ser Ala Asp Cys
    50                  55                  60

Pro Arg Trp Asn Gly Leu
65              70

<210> SEQ ID NO 3
<211> LENGTH: 49
<212> TYPE: PRT
<213> ORGANISM: Echis carinatus

<400> SEQUENCE: 3

Gln Cys Glu Ser Gly Pro Cys Cys Arg Asn Cys Lys Phe Leu Lys Glu
1               5                   10                  15

Gly Thr Ile Cys Lys Arg Ala Arg Gly Asp Asp Met Asp Asp Tyr Cys
            20                  25                  30

Asn Gly Lys Thr Cys Asp Cys Pro Arg Asn Pro His Lys Gly Pro Ala
        35                  40                  45

Thr

<210> SEQ ID NO 4
<211> LENGTH: 73
<212> TYPE: PRT
<213> ORGANISM: Trimeresurus mucrosquamatus

<400> SEQUENCE: 4

Glu Ala Gly Glu Glu Cys Asp Cys Gly Ser Pro Glu Asn Pro Cys Cys
1               5                   10                  15

Asp Ala Ala Thr Cys Lys Leu Arg Pro Gly Ala Gln Cys Ala Glu Gly
            20                  25                  30

Leu Cys Cys Asp Gln Cys Arg Phe Lys Lys Lys Arg Thr Ile Cys Arg
        35                  40                  45

-continued

Arg Ala Arg Gly Asp Asn Pro Asp Asp Arg Cys Thr Gly Gln Ser Ala
            50                  55                  60

Asp Cys Pro Arg Asn Gly Leu Tyr Gly
65                  70

<210> SEQ ID NO 5
<211> LENGTH: 73
<212> TYPE: PRT
<213> ORGANISM: Trimeresurus elegans

<400> SEQUENCE: 5

Glu Ala Gly Glu Glu Cys Asp Cys Gly Ser Pro Glu Asn Pro Cys Cys
1               5                   10                  15

Asp Ala Ala Thr Cys Lys Leu Arg Pro Gly Ala Gln Cys Ala Asp Gly
            20                  25                  30

Leu Cys Cys Asp Gln Cys Arg Phe Lys Lys Lys Arg Thr Ile Cys Arg
        35                  40                  45

Arg Ala Arg Gly Asp Asn Pro Asp Asp Arg Cys Thr Gly Gln Ser Ala
    50                  55                  60

Asp Cys Pro Arg Asn Gly Leu Tyr Ser
65                  70

<210> SEQ ID NO 6
<211> LENGTH: 62
<212> TYPE: PRT
<213> ORGANISM: Trimeresurus gramineus

<400> SEQUENCE: 6

Glu Ala Gly Glu Asp Cys Asp Cys Gly Ser Pro Ser Asn Pro Cys Cys
1               5                   10                  15

Asp Ala Ala Thr Cys Lys Leu Ile Pro Gly Ala Gln Cys Gly Glu Gly
            20                  25                  30

Leu Cys Cys Asp Gln Cys Ser Phe Ile Glu Glu Gly Thr Val Cys Arg
        35                  40                  45

Ile Ala Arg Gly Asp Asp Leu Asp Asp Tyr Cys Asn Gly Arg
    50                  55                  60

<210> SEQ ID NO 7
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 7

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Ala Asp Met Pro Asp Asp Arg Cys Thr Gly Gln Ser Ala Asp Cys
    50                  55                  60

Pro Arg Tyr His
65

<210> SEQ ID NO 8
<211> LENGTH: 68
<212> TYPE: PRT

<213> ORGANISM: Artificial Sequence
<220> FEATURE:
<223> OTHER INFORMATION: RXD peptide, mutation at X

<400> SEQUENCE: 8

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Pro Asp Met Pro Asp Asp Arg Cys Thr Gly Gln Ser Ala Asp Cys
    50                  55                  60

Pro Arg Tyr His
65
```

<210> SEQ ID NO 9
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 9

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Val Asp Met Pro Asp Asp Arg Cys Thr Gly Gln Ser Ala Asp Cys
    50                  55                  60

Pro Arg Tyr His
65
```

<210> SEQ ID NO 10
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 10

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Leu Asp Met Pro Asp Asp Arg Cys Thr Gly Gln Ser Ala Asp Cys
    50                  55                  60

Pro Arg Tyr His
65
```

<210> SEQ ID NO 11
<211> LENGTH: 68
<212> TYPE: PRT
<213> ORGANISM: Artificial Sequence
<220> FEATURE:
<223> OTHER INFORMATION: RXD peptide, mutation at X

```
<400> SEQUENCE: 11

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Ile Asp Met Pro Asp Arg Cys Thr Gly Gln Ser Ala Asp Cys
    50                  55                  60

Pro Arg Tyr His
65

<210> SEQ ID NO 12
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 12

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Met Asp Met Pro Asp Arg Cys Thr Gly Gln Ser Ala Asp Cys
    50                  55                  60

Pro Arg Tyr His
65

<210> SEQ ID NO 13
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 13

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Phe Asp Met Pro Asp Arg Cys Thr Gly Gln Ser Ala Asp Cys
    50                  55                  60

Pro Arg Tyr His
65

<210> SEQ ID NO 14
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 14

Gly Lys Glu Cys Asp Cys Ser Ser Pro Glu Asn Pro Cys Cys Asp Ala
1               5                   10                  15
```

```
Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Tyr Asp Met Pro Asp Arg Cys Thr Gly Gln Ser Ala Asp Cys
50                  55                  60

Pro Arg Tyr His
65
```

<210> SEQ ID NO 15
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 15

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Trp Asp Met Pro Asp Arg Cys Thr Gly Gln Ser Ala Asp Cys
50                  55                  60

Pro Arg Tyr His
65
```

<210> SEQ ID NO 16
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 16

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Ser Asp Met Pro Asp Arg Cys Thr Gly Gln Ser Ala Asp Cys
50                  55                  60

Pro Arg Tyr His
65
```

<210> SEQ ID NO 17
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 17

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30
```

Cys Glu Gln Cys Lys Phe Ser Arg Ala Gly Lys Ile Cys Arg Ile Pro
            35                  40                  45

Arg Thr Asp Met Pro Asp Asp Arg Cys Thr Gly Gln Ser Ala Asp Cys
    50                  55                  60

Pro Arg Tyr His
65

<210> SEQ ID NO 18
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 18

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
            35                  40                  45

Arg Asn Asp Met Pro Asp Asp Arg Cys Thr Gly Gln Ser Ala Asp Cys
    50                  55                  60

Pro Arg Tyr His
65

<210> SEQ ID NO 19
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 19

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
            35                  40                  45

Arg Gln Asp Met Pro Asp Asp Arg Cys Thr Gly Gln Ser Ala Asp Cys
    50                  55                  60

Pro Arg Tyr His
65

<210> SEQ ID NO 20
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 20

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
            35                  40                  45

Arg Asp Asp Met Pro Asp Asp Arg Cys Thr Gly Gln Ser Ala Asp Cys

Pro Arg Tyr His
65

<210> SEQ ID NO 21
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 21

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Glu Asp Met Pro Asp Arg Cys Thr Gly Gln Ser Ala Asp Cys
    50                  55                  60

Pro Arg Tyr His
65

<210> SEQ ID NO 22
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 22

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg His Asp Met Pro Asp Arg Cys Thr Gly Gln Ser Ala Asp Cys
    50                  55                  60

Pro Arg Tyr His
65

<210> SEQ ID NO 23
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 23

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Lys Asp Met Pro Asp Arg Cys Thr Gly Gln Ser Ala Asp Cys
    50                  55                  60

Pro Arg Tyr His
65

<210> SEQ ID NO 24
<211> LENGTH: 68
<212> TYPE: PRT
<213> ORGANISM: Artificial Sequence
<220> FEATURE:
<223> OTHER INFORMATION: RXD peptide, mutation at X

<400> SEQUENCE: 24

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Pro
            35                  40                  45

Arg Arg Asp Met Pro Asp Asp Arg Cys Thr Gly Gln Ser Ala Asp Cys
        50                  55                  60

Pro Arg Tyr His
65

<210> SEQ ID NO 25
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 25

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Gly
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 26
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 26

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Asp
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 27
<211> LENGTH: 68

<212> TYPE: PRT
<213> ORGANISM: Artificial Sequence
<220> FEATURE:
<223> OTHER INFORMATION: XRGD peptide, mutation at X

<400> SEQUENCE: 27

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Glu
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 28
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 28

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Val
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 29
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 29

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Leu
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 30
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 30

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ile
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 31
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 31

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Met
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 32
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 32

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 33
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 33

Gly Lys Glu Cys Asp Cys Ser Ser Pro Glu Asn Pro Cys Cys Asp Ala

```
                1               5                   10                  15
Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ser
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 34
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 34

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Thr
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 35
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 35

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Asn
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 36
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 36

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30
```

```
Cys Glu Gln Cys Lys Phe Ser Arg Ala Gly Lys Ile Cys Arg Ile Gln
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 37
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 37

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Arg
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 38
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 38

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Lys
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 39
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 39

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile His
            35                  40                  45
```

Arg Gly Asp Met Pro Asp Asp Arg Cys Thr Gly Gln Ser Ala Asp Cys
        50                  55                  60

Pro Arg Tyr His
65

<210> SEQ ID NO 40
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 40

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Phe
        35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 41
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 41

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Tyr
        35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 42
<211> LENGTH: 68
<212> TYPE: PRT
<213> ORGANISM: Artificial Sequence
<220> FEATURE:
<223> OTHER INFORMATION: XRGD peptide, mutation at X

<400> SEQUENCE: 42

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Trp
        35                  40                  45

Arg Gly Asp Met Pro Asp Asp Arg Cys Thr Gly Gln Ser Ala Asp Cys
        50                  55                  60

Pro Arg Tyr His

<210> SEQ ID NO 43
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 43

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 44
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 44

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Asp Pro Asp Asp Arg Cys Thr Gly Gln Ser Ala Asp Cys
    50                  55                  60

Pro Arg Tyr His
65

<210> SEQ ID NO 45
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 45

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Glu Pro Asp Asp Arg Cys Thr Gly Gln Ser Ala Asp Cys
    50                  55                  60

Pro Arg Tyr His
65

<210> SEQ ID NO 46

```
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 46

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
            35                  40                  45

Arg Gly Asp Leu Pro Asp Asp Arg Cys Thr Gly Gln Ser Ala Asp Cys
        50                  55                  60

Pro Arg Tyr His
65

<210> SEQ ID NO 47
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 47

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
            35                  40                  45

Arg Gly Asp Val Pro Asp Asp Arg Cys Thr Gly Gln Ser Ala Asp Cys
        50                  55                  60

Pro Arg Tyr His
65

<210> SEQ ID NO 48
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 48

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
            35                  40                  45

Arg Gly Asp Ile Pro Asp Asp Arg Cys Thr Gly Gln Ser Ala Asp Cys
        50                  55                  60

Pro Arg Tyr His
65

<210> SEQ ID NO 49
<211> LENGTH: 68
<212> TYPE: PRT
<213> ORGANISM: Artificial Sequence
<220> FEATURE:
```

<223> OTHER INFORMATION: XRGDXP peptide, mutation at X

<400> SEQUENCE: 49

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
            35                  40                  45

Arg Gly Asp Lys Pro Asp Asp Arg Cys Thr Gly Gln Ser Ala Asp Cys
        50                  55                  60

Pro Arg Tyr His
65

<210> SEQ ID NO 50
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 50

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
            35                  40                  45

Arg Gly Asp Ala Pro Asp Asp Arg Cys Thr Gly Gln Ser Ala Asp Cys
        50                  55                  60

Pro Arg Tyr His
65

<210> SEQ ID NO 51
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 51

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
            35                  40                  45

Arg Gly Asp Ser Pro Asp Asp Arg Cys Thr Gly Gln Ser Ala Asp Cys
        50                  55                  60

Pro Arg Tyr His
65

<210> SEQ ID NO 52
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 52

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
            35                  40                  45

Arg Gly Asp Thr Pro Asp Asp Arg Cys Thr Gly Gln Ser Ala Asp Cys
        50                  55                  60

Pro Arg Tyr His
65

<210> SEQ ID NO 53
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 53

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
            35                  40                  45

Arg Gly Asp Asn Pro Asp Asp Arg Cys Thr Gly Gln Ser Ala Asp Cys
        50                  55                  60

Pro Arg Tyr His
65

<210> SEQ ID NO 54
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 54

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
            35                  40                  45

Arg Gly Asp Gln Pro Asp Asp Arg Cys Thr Gly Gln Ser Ala Asp Cys
        50                  55                  60

Pro Arg Tyr His
65

<210> SEQ ID NO 55
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 55

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys

-continued

```
            20                  25                  30

Cys Glu Gln Cys Lys Phe Ser Arg Ala Gly Lys Ile Cys Arg Ile Ala
        35                  40                  45

Arg Gly Asp Trp Pro Asp Asp Arg Cys Thr Gly Gln Ser Ala Asp Cys
    50                  55                  60

Pro Arg Tyr His
65

<210> SEQ ID NO 56
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 56

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Tyr Pro Asp Asp Arg Cys Thr Gly Gln Ser Ala Asp Cys
    50                  55                  60

Pro Arg Tyr His
65

<210> SEQ ID NO 57
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 57

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Phe Pro Asp Asp Arg Cys Thr Gly Gln Ser Ala Asp Cys
    50                  55                  60

Pro Arg Tyr His
65

<210> SEQ ID NO 58
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 58

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45
```

```
Arg Gly Asp His Pro Asp Asp Arg Cys Thr Gly Gln Ser Ala Asp Cys
        50                  55                  60

Pro Arg Tyr His
65

<210> SEQ ID NO 59
<211> LENGTH: 68
<212> TYPE: PRT
<213> ORGANISM: Artificial Sequence
<220> FEATURE:
<223> OTHER INFORMATION: RXGDXP peptide, mutation at X

<400> SEQUENCE: 59

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Arg Pro Asp Asp Arg Cys Thr Gly Gln Ser Ala Asp Cys
        50                  55                  60

Pro Arg Tyr His
65

<210> SEQ ID NO 60
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 60

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Gly Pro Asp Asp Arg Cys Thr Gly Gln Ser Ala Asp Cys
        50                  55                  60

Pro Arg Tyr His
65

<210> SEQ ID NO 61
<211> LENGTH: 68
<212> TYPE: PRT
<213> ORGANISM: Artificial Sequence
<220> FEATURE:
<223> OTHER INFORMATION: XRGDXP peptide, mutation at X

<400> SEQUENCE: 61

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Pro Pro Asp Arg Cys Thr Gly Gln Ser Ala Asp Cys
        50                  55                  60
```

Pro Arg Tyr His
65

<210> SEQ ID NO 62
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 62

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Asn Asp Asp Arg Cys Thr Gly Gln Ser Ala Asp Cys
    50                  55                  60

Pro Arg Tyr His
65

<210> SEQ ID NO 63
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 63

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Gln Asp Asp Arg Cys Thr Gly Gln Ser Ala Asp Cys
    50                  55                  60

Pro Arg Tyr His
65

<210> SEQ ID NO 64
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 64

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Asp Asp Asp Arg Cys Thr Gly Gln Ser Ala Asp Cys
    50                  55                  60

Pro Arg Tyr His
65

-continued

<210> SEQ ID NO 65
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 65

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Glu Asp Asp Arg Cys Thr Gly Gln Ser Ala Asp Cys
    50                  55                  60

Pro Arg Tyr His
65

<210> SEQ ID NO 66
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 66

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met His Asp Asp Arg Cys Thr Gly Gln Ser Ala Asp Cys
    50                  55                  60

Pro Arg Tyr His
65

<210> SEQ ID NO 67
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 67

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Arg Asp Asp Arg Cys Thr Gly Gln Ser Ala Asp Cys
    50                  55                  60

Pro Arg Tyr His
65

<210> SEQ ID NO 68
<211> LENGTH: 68
<212> TYPE: PRT
<213> ORGANISM: Artificial Sequence -continued

```
<220> FEATURE:
<223> OTHER INFORMATION: XRGDMX, mutation at X

<400> SEQUENCE: 68

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Lys Asp Asp Arg Cys Thr Gly Gln Ser Ala Asp Cys
    50                  55                  60

Pro Arg Tyr His
65

<210> SEQ ID NO 69
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 69

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Gly Asp Asp Arg Cys Thr Gly Gln Ser Ala Asp Cys
    50                  55                  60

Pro Arg Tyr His
65

<210> SEQ ID NO 70
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 70

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Leu Asp Asp Arg Cys Thr Gly Gln Ser Ala Asp Cys
    50                  55                  60

Pro Arg Tyr His
65

<210> SEQ ID NO 71
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 71
```

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
                35                  40                  45

Arg Gly Asp Met Trp Asp Arg Cys Thr Gly Gln Ser Ala Asp Cys
            50                  55                  60

Pro Arg Tyr His
65

<210> SEQ ID NO 72
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 72

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
                35                  40                  45

Arg Gly Asp Met Phe Asp Arg Cys Thr Gly Gln Ser Ala Asp Cys
            50                  55                  60

Pro Arg Tyr His
65

<210> SEQ ID NO 73
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 73

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
                35                  40                  45

Arg Gly Asp Met Tyr Asp Arg Cys Thr Gly Gln Ser Ala Asp Cys
            50                  55                  60

Pro Arg Tyr His
65

<210> SEQ ID NO 74
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 74

Gly Lys Glu Cys Asp Cys Ser Ser Pro Glu Asn Pro Cys Cys Asp Ala
1               5                   10                  15

```
Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Met Asp Asp Arg Cys Thr Gly Gln Ser Ala Asp Cys
    50                  55                  60

Pro Arg Tyr His
65

<210> SEQ ID NO 75
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 75

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Ala Asp Asp Arg Cys Thr Gly Gln Ser Ala Asp Cys
    50                  55                  60

Pro Arg Tyr His
65

<210> SEQ ID NO 76
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 76

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Ile Asp Asp Arg Cys Thr Gly Gln Ser Ala Asp Cys
    50                  55                  60

Pro Arg Tyr His
65

<210> SEQ ID NO 77
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 77

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
```

```
                35                  40                  45

Arg Gly Asp Met Val Asp Arg Cys Thr Gly Gln Ser Ala Asp Cys
    50                  55                  60

Pro Arg Tyr His
65

<210> SEQ ID NO 78
<211> LENGTH: 68
<212> TYPE: PRT
<213> ORGANISM: Artificial Sequence
<220> FEATURE:
<223> OTHER INFORMATION: XRGDMX, mutation at X

<400> SEQUENCE: 78

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
                35                  40                  45

Arg Gly Asp Met Thr Asp Arg Cys Thr Gly Gln Ser Ala Asp Cys
    50                  55                  60

Pro Arg Tyr His
65

<210> SEQ ID NO 79
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 79

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Arg Pro
                35                  40                  45

Arg Gly Asp Met Pro Asp Arg Cys Thr Gly Gln Ser Ala Asp Cys
    50                  55                  60

Pro Arg Tyr His
65

<210> SEQ ID NO 80
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 80

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Met Pro
                35                  40                  45

Arg Gly Asp Met Pro Asp Arg Cys Thr Gly Gln Ser Ala Asp Cys
    50                  55                  60
```

Pro Arg Tyr His
65

<210> SEQ ID NO 81
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 81

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Val Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 82
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 82

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ala Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 83
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 83

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Gln Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 84
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 84

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Glu Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 85
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 85

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Phe Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 86
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 86

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Pro Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 87
<211> LENGTH: 68
<212> TYPE: PRT

<213> ORGANISM: Artificial Sequence
<220> FEATURE:
<223> OTHER INFORMATION: XXPRGD, mutation at X

<400> SEQUENCE: 87

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Lys Arg Pro
            35                  40                  45

Arg Gly Asp Met Pro Asp Arg Cys Thr Gly Gln Ser Ala Asp Cys
        50                  55                  60

Pro Arg Tyr His
65

<210> SEQ ID NO 88
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 88

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Lys Lys Pro
            35                  40                  45

Arg Gly Asp Met Pro Asp Arg Cys Thr Gly Gln Ser Ala Asp Cys
        50                  55                  60

Pro Arg Tyr His
65

<210> SEQ ID NO 89
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 89

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Lys Met Pro
            35                  40                  45

Arg Gly Asp Met Pro Asp Arg Cys Thr Gly Gln Ser Ala Asp Cys
        50                  55                  60

Pro Arg Tyr His
65

<210> SEQ ID NO 90
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 90

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Lys Ile Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 91
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 91

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Phe Ile Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 92
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 92

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Gln Ile Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 93
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 93

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Ala Ile Pro
        35                  40                  45

Arg Gly Asp Met Pro Asp Arg Cys Thr Gln Ser Ala Asp Cys
    50                  55                  60

Pro Arg Tyr His
65

<210> SEQ ID NO 94
<211> LENGTH: 68
<212> TYPE: PRT
<213> ORGANISM: Artificial Sequence
<220> FEATURE:
<223> OTHER INFORMATION: XXPRGD, mutation at X

<400> SEQUENCE: 94

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Glu Ile Pro
        35                  40                  45

Arg Gly Asp Met Pro Asp Arg Cys Thr Gln Ser Ala Asp Cys
    50                  55                  60

Pro Arg Tyr His
65

<210> SEQ ID NO 95
<211> LENGTH: 68
<212> TYPE: PRT
<213> ORGANISM: Artificial Sequence
<220> FEATURE:
<223> OTHER INFORMATION: XRXDXP, mutation at X

<400> SEQUENCE: 95

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Glu Pro Asp Arg Cys Thr Gln Ser Ala Asp Cys
    50                  55                  60

Pro Arg Tyr His
65

<210> SEQ ID NO 96
<211> LENGTH: 68
<212> TYPE: PRT
<213> ORGANISM: Artificial Sequence
<220> FEATURE:
<223> OTHER INFORMATION: XRXDXP, mutation at X

<400> SEQUENCE: 96

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

```
Cys Glu Gln Cys Lys Phe Ser Arg Ala Gly Lys Ile Cys Arg Ile Arg
            35                  40                  45

Arg Gly Asp Glu Pro Asp Asp Arg Cys Thr Gly Gln Ser Ala Asp Cys
 50                  55                  60

Pro Arg Tyr His
 65

<210> SEQ ID NO 97
<211> LENGTH: 68
<212> TYPE: PRT
<213> ORGANISM: Artificial Sequence
<220> FEATURE:
<223> OTHER INFORMATION: XRXDXP, mutation at X

<400> SEQUENCE: 97

Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
            35                  40                  45

Arg Leu Asp Glu Pro Asp Asp Arg Cys Thr Gly Gln Ser Ala Asp Cys
 50                  55                  60

Pro Arg Tyr His
 65

<210> SEQ ID NO 98
<211> LENGTH: 68
<212> TYPE: PRT
<213> ORGANISM: Artificial Sequence
<220> FEATURE:
<223> OTHER INFORMATION: XRXDXP, mutation at X

<400> SEQUENCE: 98

Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Arg
            35                  40                  45

Arg Leu Asp Glu Pro Asp Asp Arg Cys Thr Gly Gln Ser Ala Asp Cys
 50                  55                  60

Pro Arg Tyr His
 65

<210> SEQ ID NO 99
<211> LENGTH: 68
<212> TYPE: PRT
<213> ORGANISM: Artificial Sequence
<220> FEATURE:
<223> OTHER INFORMATION: XRXDXP, mutation at X

<400> SEQUENCE: 99

Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
            35                  40                  45

Arg Gln Asp Glu Pro Asp Asp Arg Cys Thr Gly Gln Ser Ala Asp Cys
```

```
                50                  55                  60

Pro Arg Tyr His
 65

<210> SEQ ID NO 100
<211> LENGTH: 68
<212> TYPE: PRT
<213> ORGANISM: Artificial Sequence
<220> FEATURE:
<223> OTHER INFORMATION: XRXDXP, mutation at X

<400> SEQUENCE: 100

Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Arg
            35                  40                  45

Arg Gln Asp Glu Pro Asp Arg Cys Thr Gly Gln Ser Ala Asp Cys
        50                  55                  60

Pro Arg Tyr His
 65

<210> SEQ ID NO 101
<211> LENGTH: 68
<212> TYPE: PRT
<213> ORGANISM: Artificial Sequence
<220> FEATURE:
<223> OTHER INFORMATION: XRXDXP, mutation at X

<400> SEQUENCE: 101

Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Arg
            35                  40                  45

Arg Gln Asp Ser Pro Asp Arg Cys Thr Gly Gln Ser Ala Asp Cys
        50                  55                  60

Pro Arg Tyr His
 65

<210> SEQ ID NO 102
<211> LENGTH: 70
<212> TYPE: PRT
<213> ORGANISM: Artificial Sequence
<220> FEATURE:
<223> OTHER INFORMATION: PRGDMP-PRXXXXX, mutation at X

<400> SEQUENCE: 102

Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Pro
            35                  40                  45

Arg Gly Asp Met Pro Asp Arg Cys Thr Gly Gln Ser Ala Asp Cys
        50                  55                  60

Pro Arg Trp Asn Asp Leu
 65                  70
```

<210> SEQ ID NO 103
<211> LENGTH: 70
<212> TYPE: PRT
<213> ORGANISM: Artificial Sequence
<220> FEATURE:
<223> OTHER INFORMATION: PRGDMP-PRXXXXX, mutation at X

<400> SEQUENCE: 103

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Met Pro Asp Arg Cys Thr Gly Gln Ser Ala Asp Cys
    50                  55                  60

Pro Arg Asn Arg Phe His
65                  70
```

<210> SEQ ID NO 104
<211> LENGTH: 71
<212> TYPE: PRT
<213> ORGANISM: Artificial Sequence
<220> FEATURE:
<223> OTHER INFORMATION: PRGDMP-PRXXXXX, mutation at X

<400> SEQUENCE: 104

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Met Pro Asp Arg Cys Thr Gly Gln Ser Ala Asp Cys
    50                  55                  60

Pro Arg Asn Arg Phe His Ala
65                  70
```

<210> SEQ ID NO 105
<211> LENGTH: 71
<212> TYPE: PRT
<213> ORGANISM: Artificial Sequence
<220> FEATURE:
<223> OTHER INFORMATION: PRGDMP-PRXXXXX, mutation at X

<400> SEQUENCE: 105

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Met Pro Asp Arg Cys Thr Gly Gln Ser Ala Asp Cys
    50                  55                  60

Pro Arg Asn Pro Trp Asn Gly
65                  70
```

<210> SEQ ID NO 106
<211> LENGTH: 71

<212> TYPE: PRT
<213> ORGANISM: Artificial Sequence
<220> FEATURE:
<223> OTHER INFORMATION: PRGDMP-PRXXXXX, mutation at X

<400> SEQUENCE: 106

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Met Pro Asp Asp Arg Cys Thr Gly Gln Ser Ala Asp Cys
    50                  55                  60

Pro Arg Asn Gly Leu Tyr Gly
65                  70

<210> SEQ ID NO 107
<211> LENGTH: 69
<212> TYPE: PRT
<213> ORGANISM: Artificial Sequence
<220> FEATURE:
<223> OTHER INFORMATION: PRGDMP-PRXXXXX peptide, mutation at X

<400> SEQUENCE: 107

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Met Pro Asp Asp Arg Cys Thr Gly Gln Ser Ala Asp Cys
    50                  55                  60

Pro Gly Leu Tyr Gly
65

<210> SEQ ID NO 108
<211> LENGTH: 68
<212> TYPE: PRT
<213> ORGANISM: Artificial Sequence
<220> FEATURE:
<223> OTHER INFORMATION: KKKRT-XRXDXP peptide, mutation at X

<400> SEQUENCE: 108

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Arg Thr Ile Cys Arg Ile Ala
        35                  40                  45

Arg Leu Asp Asp Pro Asp Asp Arg Cys Thr Gly Gln Ser Ala Asp Cys
    50                  55                  60

Pro Arg Tyr His
65

<210> SEQ ID NO 109
<211> LENGTH: 68
<212> TYPE: PRT
<213> ORGANISM: Artificial Sequence
<220> FEATURE:
<223> OTHER INFORMATION: KKKRT-XRXDXP peptide, mutation at X

<400> SEQUENCE: 109

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Arg Thr Ile Cys Arg Ile Ala
        35                  40                  45

Arg Met Asp Asp Pro Asp Asp Arg Cys Thr Gly Gln Ser Ala Asp Cys
    50                  55                  60

Pro Arg Tyr His
65

<210> SEQ ID NO 110
<211> LENGTH: 68
<212> TYPE: PRT
<213> ORGANISM: Artificial Sequence
<220> FEATURE:
<223> OTHER INFORMATION: KKKRT-XRXDXP peptide, mutation at X

<400> SEQUENCE: 110

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Arg Thr Ile Cys Arg Ile Ala
        35                  40                  45

Arg Pro Asp Asp Pro Asp Asp Arg Cys Thr Gly Gln Ser Ala Asp Cys
    50                  55                  60

Pro Arg Tyr His
65

<210> SEQ ID NO 111
<211> LENGTH: 68
<212> TYPE: PRT
<213> ORGANISM: Artificial Sequence
<220> FEATURE:
<223> OTHER INFORMATION: KKKRT-XRXDXP peptide, mutation at X

<400> SEQUENCE: 111

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Arg Thr Ile Cys Arg Ile Ala
        35                  40                  45

Arg Leu Asp Met Pro Asp Asp Arg Cys Thr Gly Gln Ser Ala Asp Cys
    50                  55                  60

Pro Arg Tyr His
65

<210> SEQ ID NO 112
<211> LENGTH: 68
<212> TYPE: PRT
<213> ORGANISM: Artificial Sequence
<220> FEATURE:
<223> OTHER INFORMATION: KKKRT-XRXDXP peptide, mutation at X

<400> SEQUENCE: 112

Gly Lys Glu Cys Asp Cys Ser Ser Pro Glu Asn Pro Cys Cys Asp Ala

```
                1               5                  10                 15
Ala Thr Cys Lys Leu Arg Pro Gly Ala Gln Cys Gly Glu Gly Leu Cys
            20                  25                 30

Cys Glu Gln Cys Lys Phe Lys Lys Lys Arg Thr Ile Cys Arg Ile Ala
            35                  40                 45

Arg Leu Asp Asn Pro Asp Asp Arg Cys Thr Gly Gln Ser Ala Asp Cys
    50                  55                 60

Pro Arg Tyr His
65

<210> SEQ ID NO 113
<211> LENGTH: 68
<212> TYPE: PRT
<213> ORGANISM: Artificial Sequence
<220> FEATURE:
<223> OTHER INFORMATION: KKKRT-XRXDXP peptide, mutation at X

<400> SEQUENCE: 113

Gly Lys Glu Cys Asp Cys Ser Ser Pro Glu Asn Pro Cys Cys Asp Ala
1               5                  10                 15

Ala Thr Cys Lys Leu Arg Pro Gly Ala Gln Cys Gly Glu Gly Leu Cys
            20                  25                 30

Cys Glu Gln Cys Lys Phe Lys Lys Lys Arg Thr Ile Cys Arg Ile Ala
            35                  40                 45

Arg Leu Asp Asp Val Asp Asp Arg Cys Thr Gly Gln Ser Ala Asp Cys
    50                  55                 60

Pro Arg Tyr His
65

<210> SEQ ID NO 114
<211> LENGTH: 68
<212> TYPE: PRT
<213> ORGANISM: Artificial Sequence
<220> FEATURE:
<223> OTHER INFORMATION: KKKRT-XRXDXP peptide, mutation at X

<400> SEQUENCE: 114

Gly Lys Glu Cys Asp Cys Ser Ser Pro Glu Asn Pro Cys Cys Asp Ala
1               5                  10                 15

Ala Thr Cys Lys Leu Arg Pro Gly Ala Gln Cys Gly Glu Gly Leu Cys
            20                  25                 30

Cys Glu Gln Cys Lys Phe Lys Lys Lys Arg Thr Ile Cys Arg Ile Ala
            35                  40                 45

Arg Leu Asp Asp Leu Asp Asp Arg Cys Thr Gly Gln Ser Ala Asp Cys
    50                  55                 60

Pro Arg Tyr His
65

<210> SEQ ID NO 115
<211> LENGTH: 66
<212> TYPE: PRT
<213> ORGANISM: Artificial Sequence
<220> FEATURE:
<223> OTHER INFORMATION: ARGDMP-PRXXXXX peptide, mutation at X

<400> SEQUENCE: 115

Gly Lys Glu Cys Asp Cys Ser Ser Pro Glu Asn Pro Cys Cys Asp Ala
1               5                  10                 15

Ala Thr Cys Lys Leu Arg Pro Gly Ala Gln Cys Gly Glu Gly Leu Cys
            20                  25                 30
```

Cys Glu Gln Cys Lys Phe Ser Arg Ala Gly Lys Ile Cys Arg Ile Ala
            35                  40                  45

Arg Gly Asp Met Pro Asp Asp Arg Cys Thr Gly Gln Ser Ala Asp Cys
        50                  55                  60

Pro Arg
65

<210> SEQ ID NO 116
<211> LENGTH: 68
<212> TYPE: PRT
<213> ORGANISM: Artificial Sequence
<220> FEATURE:
<223> OTHER INFORMATION: ARGDMP-PRXXXXX peptide, mutation at X

<400> SEQUENCE: 116

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 117
<211> LENGTH: 69
<212> TYPE: PRT
<213> ORGANISM: Artificial Sequence
<220> FEATURE:
<223> OTHER INFORMATION: ARGDMP-PRXXXXX peptide, mutation at X

<400> SEQUENCE: 117

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
            35                  40                  45

Arg Gly Asp Met Pro Asp Asp Arg Cys Thr Gly Gln Ser Ala Asp Cys
        50                  55                  60

Pro Arg Asn Gly Leu
65

<210> SEQ ID NO 118
<211> LENGTH: 71
<212> TYPE: PRT
<213> ORGANISM: Artificial Sequence
<220> FEATURE:
<223> OTHER INFORMATION: ARGDMP-PRXXXXX peptide, mutation at X

<400> SEQUENCE: 118

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
            35                  40                  45

Arg Gly Asp Met Pro Asp Asp Arg Cys Thr Gly Gln Ser Ala Asp Cys
    50                  55                  60

Pro Arg Asn Pro Trp Asn Gly
65                  70

<210> SEQ ID NO 119
<211> LENGTH: 71
<212> TYPE: PRT
<213> ORGANISM: Artificial Sequence
<220> FEATURE:
<223> OTHER INFORMATION: ARGDMP-PRXXXXX peptide, mutation at X

<400> SEQUENCE: 119

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
            35                  40                  45

Arg Gly Asp Met Pro Asp Asp Arg Cys Thr Gly Gln Ser Ala Asp Cys
    50                  55                  60

Pro Arg Asn Gly Leu Tyr Gly
65                  70

<210> SEQ ID NO 120
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 120

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
    50                  55                  60

Pro Tyr Leu Tyr Gly
65

<210> SEQ ID NO 121
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 121

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
    50                  55                  60

Pro Glu Leu Tyr Gly

<210> SEQ ID NO 122
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 122

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Ala
        35                  40                  45

Arg Gly Asp Asp Leu Asp Asp Arg Cys Thr Gly Gln Ser Ala Asp Cys
    50                  55                  60

Pro Gly Leu Tyr Gly
65
```

<210> SEQ ID NO 123
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 123

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Arg Tyr His
65
```

<210> SEQ ID NO 124
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 124

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Gly Leu Tyr Gly
65
```

<210> SEQ ID NO 125

<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 125

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Ala
            35                  40                  45

Arg Leu Asp Asp Leu Asp Asp Arg Cys Thr Gly Gln Ser Ala Asp Cys
        50                  55                  60

Pro Arg Tyr His
65
```

<210> SEQ ID NO 126
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 126

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Asp Asp Pro
            35                  40                  45

Arg Gly Asp Met Pro Asp Asp Arg Cys Thr Gly Gln Ser Ala Asp Cys
        50                  55                  60

Pro Arg Tyr His
65
```

<210> SEQ ID NO 127
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 127

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Lys Arg Thr Ile Cys Arg Ile Pro
            35                  40                  45

Arg Gly Asp Met Pro Asp Asp Arg Cys Thr Gly Gln Ser Ala Asp Cys
        50                  55                  60

Pro Arg Tyr His
65
```

<210> SEQ ID NO 128
<211> LENGTH: 68
<212> TYPE: PRT
<213> ORGANISM: Artificial Sequence
<220> FEATURE:

<223> OTHER INFORMATION: XXXXX-ICXXXRGDXP-XXXXX peptide, mutation at X

<400> SEQUENCE: 128

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Arg Thr Ile Cys Arg Ile Ala
        35                  40                  45

Arg Gly Asp Asn Pro Asp Asp Arg Cys Thr Gly Gln Ser Ala Asp Cys
        50                  55                  60

Pro Arg Asn Gly Leu Tyr Gly
65                  70

<210> SEQ ID NO 132
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 132

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Arg Thr Ile Cys Arg Arg Ala
        35                  40                  45

Arg Gly Asp Asn Pro Asp Asp Arg Cys Thr Gly Gln Ser Ala Asp Cys
        50                  55                  60

Pro Arg Asn Gly Leu Tyr Gly
65                  70

<210> SEQ ID NO 133
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 133

Gly Lys Glu Cys Asp Cys Ser Ser Pro Glu Asn P

```
                20                  25                  30
Cys Glu Gln Cys Lys Phe Met Lys Lys Gly Thr Ile Cys Arg Ile Ala
            35                  40                  45

Arg Gly Asp Asn Pro Asp Asp Arg Cys Thr Gly Gln Ser Ala Asp Cys
        50                  55                  60

Pro Arg Asn Gly Leu Tyr Gly
65                  70

<210> SEQ ID NO 135
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 135

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ile Glu Glu Gly Thr Ile Cys Arg Ile Ala
            35                  40                  45

Arg Gly Asp Asn Pro Asp Asp Arg Cys Thr Gly Gln Ser Ala Asp Cys
        50                  55                  60

Pro Arg Asn Gly Leu Tyr Gly
65                  70

<210> SEQ ID NO 136
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 136

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Gly Ala Gly Lys Ile Cys Arg Ile Ala
            35                  40                  45

Arg Gly Asp Asn Pro Asp Asp Arg Cys Thr Gly Gln Ser Ala Asp Cys
        50                  55                  60

Pro Arg Asn Gly Leu Tyr Gly
65                  70

<210> SEQ ID NO 137
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 137

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Leu Lys Glu Gly Thr Ile Cys Arg Ile Ala
            35                  40                  45
```

Arg Gly Asp Asn Pro Asp Asp Arg Cys Thr Gly Gln Ser Ala Asp Cys
            50                  55                  60

Pro Arg Asn Gly Leu Tyr Gly
 65                  70

<210> SEQ ID NO 138
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 138

Gly Lys Glu Cys Asp Cys Ser Ser Pro Glu Asn Pro Cys Cys Asp Ala
 1               5                   10                  15

Ala Thr Cys Lys Leu Arg Pro Gly Ala Gln Cys Gly Glu Gly Leu Cys
            20                  25                  30

Cys Glu Gln Cys Lys Phe Ala Lys Lys Arg Thr Ile Cys Arg Ile Ala
        35                  40                  45

Arg Gly Asp Asn Pro Asp Asp Arg Cys Thr Gly Gln Ser Ala Asp Cys
    50                  55                  60

Pro Arg Asn Gly Leu Tyr Gly
 65                  70

<210> SEQ ID NO 139
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE

Pro Arg Asn Gly Leu Tyr Gly
65                  70

<210> SEQ ID NO 141
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 141

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Ala Thr Ile Cys Arg Ile Ala
        35                  40                  45

Arg Gly Asp Asn Pro Asp Asp Arg Cys Thr Gly Gln Ser Ala Asp Cys
    50                  55                  60

Pro Arg Asn Gly Leu Tyr Gly
65                  70

<210> SEQ ID NO 142
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 142

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Arg Ala Ile Cys Arg Ile Ala
        35                  40                  45

Arg Gly Asp Asn Pro Asp Asp Arg Cys Thr Gly Gln Ser Ala Asp Cys
    50                  55                  60

Pro Arg Asn Gly Leu Tyr Gly
65                  70

<210> SEQ ID NO 143
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 143

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Ala Lys Arg Ala Ile Cys Arg Ile Ala
        35                  40                  45

Arg Gly Asp Asn Pro Asp Asp Arg Cys Thr Gly Gln Ser Ala Asp Cys
    50                  55                  60

Pro Arg Asn Gly Leu Tyr Gly
65                  70

```
<210> SEQ ID NO 144
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 144

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Lys Ala Gly Thr Ile Cys Arg Ile Ala
        35                  40                  45

Arg Gly Asp Asn Pro Asp Asp Arg Cys Th

<220> FEATURE:
<223> OTHER INFORMATION: XXXXX-ICXXXRGDXP-XXXXX peptide, mutation at X

<400> SEQUENCE: 147

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Asp Leu Tyr Gly
65

<210> SEQ ID NO 148
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 148

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Lys Leu Tyr Gly
65

<210> SEQ ID NO 149
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 149

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Arg Leu Tyr Gly
65

<210> SEQ ID NO 150
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 150

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Ala
            35                  40                  45

Arg Gly Asp Asp Leu Asp Asp Arg Cys Thr Gly Gln Ser Ala Asp Cys
        50                  55                  60

Pro Gly Leu Tyr Gly
65

<210> SEQ ID NO 151
<211> LENGTH: 70
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 151

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Arg Ile Ala
            35                  40                  45

Arg Ala Arg Gly Asp Asp Leu Asp Asp Arg Cys Thr Gly Gln Ser Ala
        50                  55                  60

Asp Cys Pro Arg Tyr His
65                  70

<210> SEQ ID NO 152
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 152

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
        50                  55                  60

Pro Gly Leu Ala Gly
65

<210> SEQ ID NO 153
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 153

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Gly Leu Pro Gly
65

<210> SEQ ID NO 154
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 154

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Gly Leu Arg Gly
65

<210> SEQ ID NO 155
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 155

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Gly Leu Asp Gly
65

<210> SEQ ID NO 156
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 156

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly

```
            35                  40                  45
Arg Gly Asp Asn Pro Asp Arg Cys Thr Gly Gln Ser

Pro Asp Glu Tyr
65

<210> SEQ ID NO 160
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 160

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Pro Leu Tyr Gly
65

<210> SEQ ID NO 161
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 161

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Asp Leu Tyr
65

<210> SEQ ID NO 162
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 162

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Asp Leu Gly
65

<210> SEQ ID NO 163
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 163

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
        50                  55                  60

Pro Asp Leu Glu
65

<210> SEQ ID NO 164
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 164

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
        50                  55                  60

Pro Asp Leu Lys
65

<210> SEQ ID NO 165
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 165

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
        50                  55                  60

Pro Asp Leu His
65

<210> SEQ ID NO 166
<211> LENGTH: 68
<212> TYPE: PRT

```
<213> ORGANISM: Artificial Sequence
<220> FEATURE:
<223> OTHER INFORMATION: XXXXX-ICXXXRGDXP-XXXXX peptide, mutation at X

<400> SEQUENCE: 166

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Arg Thr Ile Cys Arg Arg Ala
        35                  40                  45

Arg Gly Asp Asn Pro Asp Asp Arg Cys Thr Gly Gln Ser Ala Asp Cys
    50                  55                  60

Pro Arg Tyr His
65

<210> SEQ ID NO 167
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 167

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Arg Thr Ile Cys Ala Ile Ala
        35                  40                  45

Arg Gly Asp Asn Pro Asp Asp Arg Cys Thr Gly Gln Ser Ala Asp Cys
    50                  55                  60

Pro Arg Tyr His
65

<210> SEQ ID NO 168
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 168

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Lys Arg Thr Ile Cys Ala Arg Ala
        35                  40                  45

Arg Gly Asp Asn Pro Asp Asp Arg Cys Thr Gly Gln Ser Ala Asp Cys
    50                  55                  60

Pro Arg Tyr His
65

<210> SEQ ID NO 169
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X
```

```
<400> SEQUENCE: 169

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Arg Thr Ile Cys Ala Arg Ala
            35                  40                  45

Arg Gly Asp Asn Pro Asp Asp Arg Cys Thr Gly Gln Ser Ala Asp Cys
    50                  55                  60

Pro Arg Asn Gly Leu Tyr Gly
65                  70

<210> SEQ ID NO 170
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 170

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
    50                  55                  60

Pro Arg Tyr His
65

<210> SEQ ID NO 171
<211> LENGTH: 70
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 171

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
    50                  55                  60

Pro Arg Trp Asn Asp Leu
65                  70

<210> SEQ ID NO 172
<211> LENGTH: 70
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 172

Gly Lys Glu Cys Asp Cys Ser Ser Pro Glu Asn Pro Cys Cys Asp Ala
1               5                   10                  15
```

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
        50                  55                  60

Pro Arg Asn Arg Phe His
65                   70

<210> SEQ ID NO 173
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 173

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
        50                  55                  60

Pro Arg Asn Pro Phe His Ala
65                   70

<210> SEQ ID NO 174
<211> LENGTH: 69
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 174

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
            35                  40                  45

Arg Gly Asp Asn Pro Asp Asp Arg Cys Thr Gly Gln Ser Ala Asp Cys
        50                  55                  60

Pro Arg Trp Asn Gly
65

<210> SEQ ID NO 175
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 175

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

```
Cys Glu Gln Cys Lys Phe Lys Lys Ala Arg Thr Ile Cys Ala Arg Gly
             35                  40                  45

Arg Gly Asp Asn Pro Asp Arg Cys Thr Gly Gln Ser Ala Asp Cys
 50                  55                  60

Pro Arg Asn Gly Leu Tyr Gly
 65                  70
```

<210> SEQ ID NO 176
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 176

```
Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
             35                  40                  45

Arg Gly Asp Met Pro Asp Arg Cys Thr Gly Gln Ser Ala Asp Cys
 50                  55                  60

Ala Arg Tyr His
 65
```

<210> SEQ ID NO 177
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 177

```
Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
             35                  40                  45

Arg Gly Asp Met Pro Asp Arg Cys Thr Gly Gln Ser Ala Asp Cys
 50                  55                  60

Pro Ala Tyr His
 65
```

<210> SEQ ID NO 178
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 178

```
Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
             20                  25                  30

Cys Glu Gln Cys Lys Phe Ser Arg Ala Gly Lys Ile Cys Arg Ile Pro
             35                  40                  45

Arg Gly Asp Met Pro Asp Asp Arg Cys Thr Gly Gln Ser Ala Asp Cys
```

```
                    50                  55                  60

Pro Arg Ala His
 65

<210> SEQ ID NO 179
<211> LENGTH: 68
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 179

Gly Lys Glu Cys Asp Cys Ser Ser Pro Glu Asn Pro Cys Cys Asp Ala
 1               5                  10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Pro
            35                  40                  45

Arg Gly Asp Met Pro Asp Asp Arg Cys Thr Gly Gln Ser Ala Asp Cys
        50                  55                  60

Pro Arg Tyr Ala
 65

<210> SEQ ID NO 180
<211> LENGTH: 36
<212> TYPE: DNA
<213> ORGANISM: Artificial Sequence
<220> FEATURE:
<223> OTHER INFORMATION: antisense primer

<400> SEQUENCE: 180
ccgcggccgc ggtcagtggt atcttggaca gtcagc                               36

<210> SEQ ID NO 181
<211> LENGTH: 12
<212> TYPE: DNA
<213> ORGANISM: Artificial Sequence
<220> FEATURE:
<223> OTHER INFORMATION: sense primer

<400> SEQUENCE: 181
agaggtgaca tg                                                         12

<210> SEQ ID NO 182
<211> LENGTH: 23
<212> TYPE: DNA
<213> ORGANISM: Artificial Sequence
<220> FEATURE:
<223> OTHER INFORMATION: antisense primer

<400> SEQUENCE: 182
catgtcacct ctaccgattc tac                                             23

<210> SEQ ID NO 183
<211> LENGTH: 51
<212> TYPE: DNA
<213> ORGANISM: Artificial Sequence
<220> FEATURE:
<223> OTHER INFORMATION: sense primer

<400> SEQUENCE: 183
gaattcgaat tccatcatca tcatcatcat ggtaaggaat gtgactgttc t              51
```

```
<210> SEQ ID NO 184
<211> LENGTH: 36
<212> TYPE: DNA
<213> ORGANISM: Artificial Sequence
<220> FEATURE:
<223> OTHER INFORMATION: antisense primer

<400> SEQUENCE: 184
ccgcggccgc ggttagtggt atcttggaca gtcagc                            36

<210> SEQ ID NO 185
<211> LENGTH: 23
<212> TYPE: DNA
<213> ORGANISM: Artificial Sequence
<220> FEATURE:
<223> OTHER INFORMATION: antisense primer

<400> SEQUENCE: 185
catgtcacct ctcaagattc tac                                          23

<210> SEQ ID NO 186
<211> LENGTH: 23
<212> TYPE: DNA
<213> ORGANISM: Artificial Sequence
<220> FEATURE:
<223> OTHER INFORMATION: antisense primer

<400> SEQUENCE: 186
catgtcacct cttctgattc tac                                          23

<210> SEQ ID NO 187
<211> LENGTH: 23
<212> TYPE: DNA
<213> ORGANISM: Artificial Sequence
<220> FEATURE:
<223> OTHER INFORMATION: antisense primer

<400> SEQUENCE: 187
catgtcacct ctaacgattc tac                                          23

<210> SEQ ID NO 188
<211> LENGTH: 23
<212> TYPE: DNA
<213> ORGANISM: Artificial Sequence
<220> FEATURE:
<223> OTHER INFORMATION: antisense primer

<400> SEQUENCE: 188
catgtcacct ctatggattc tac                                          23

<210> SEQ ID NO 189
<211> LENGTH: 23
<212> TYPE: DNA
<213> ORGANISM: Artificial Sequence
<220> FEATURE:
<223> OTHER INFORMATION: antisense primer

<400> SEQUENCE: 189
catgtcacct ctccagattc tac                                          23

<210> SEQ ID NO 190
<211> LENGTH: 23
<212> TYPE: DNA
<213> ORGANISM: Artificial Sequence
<220> FEATURE:
<223> OTHER INFORMATION: antisense primer
```

```
<400> SEQUENCE: 190
catgtcacct ctaaagattc tac                                          23

<210> SEQ ID NO 191
<211> LENGTH: 24
<212> TYPE: DNA
<213> ORGANISM: Artificial Sequence
<220> FEATURE:
<223> OTHER INFORMATION: sense primer

<400> SEQUENCE: 191
tgtagaatcg ctagaggtga catg                                         24

<210> SEQ ID NO 192
<211> LENGTH: 24
<212> TYPE: DNA
<213> ORGANISM: Artificial Sequence
<220> FEATURE:
<223> OTHER INFORMATION: antisense primer

<400> SEQUENCE: 192
catgtcacct ctagcgattc taca                                         24

<210> SEQ ID NO 193
<211> LENGTH: 23
<212> TYPE: DNA
<213> ORGANISM: Artificial Sequence
<220> FEATURE:
<223> OTHER INFORMATION: antisense primer

<400> SEQUENCE: 193
catgtcacct ctagagattc tac                                          23

<210> SEQ ID NO 194
<211> LENGTH: 23
<212> TYPE: DNA
<213> ORGANISM: Artificial Sequence
<220> FEATURE:
<223> OTHER INFORMATION: antisense primer

<400> SEQUENCE: 194
catgtcacct ctcatgattc tac                                          23

<210> SEQ ID NO 195
<211> LENGTH: 23
<212> TYPE: DNA
<213> ORGANISM: Artificial Sequence
<220> FEATURE:
<223> OTHER INFORMATION: antisense primer

<400> SEQUENCE: 195
catgtcacct ctagtgattc tac                                          23

<210> SEQ ID NO 196
<211> LENGTH: 23
<212> TYPE: DNA
<213> ORGANISM: Artificial Sequence
<220> FEATURE:
<223> OTHER INFORMATION: antisense primer

<400> SEQUENCE: 196
catgtcacct ctgttgattc tac                                          23

<210> SEQ ID NO 197
<211> LENGTH: 23
```

```
<212> TYPE: DNA
<213> ORGANISM: Artificial Sequence
<220> FEATURE:
<223> OTHER INFORMATION: antisense primer

<400> SEQUENCE: 197
catgtcacct ctttggattc tac                                          23

<210> SEQ ID NO 198
<211> LENGTH: 23
<212> TYPE: DNA
<213> ORGANISM: Artificial Sequence
<220> FEATURE:
<223> OTHER INFORMATION: antisense primer

<400> SEQUENCE: 198
catgtcacct ctgtagattc tac                                          23

<210> SEQ ID NO 199
<211> LENGTH: 23
<212> TYPE: DNA
<213> ORGANISM: Artificial Sequence
<220> FEATURE:
<223> OTHER INFORMATION: antisense primer

<400> SEQUENCE: 199
catgtcacct ctaatgattc tac                                          23

<210> SEQ ID NO 200
<211> LENGTH: 23
<212> TYPE: DNA
<213> ORGANISM: Artificial Sequence
<220> FEATURE:
<223> OTHER INFORMATION: antisense primer

<400> SEQUENCE: 200
catgtcacct ctcttgattc tac                                          23

<210> SEQ ID NO 201
<211> LENGTH: 23
<212> TYPE: DNA
<213> ORGANISM: Artificial Sequence
<220> FEATURE:
<223> OTHER INFORMATION: antisense primer

<400> SEQUENCE: 201
catgtcacct ctttcgattc tac                                          23

<210> SEQ ID NO 202
<211> LENGTH: 23
<212> TYPE: DNA
<213> ORGANISM: Artificial Sequence
<220> FEATURE:
<223> OTHER INFORMATION: antisense primer

<400> SEQUENCE: 202
catgtcacct ctatcgattc tac                                          23

<210> SEQ ID NO 203
<211> LENGTH: 25
<212> TYPE: DNA
<213> ORGANISM: Artificial Sequence
<220> FEATURE:
<223> OTHER INFORMATION: sense primer

<400> SEQUENCE: 203
```
gtagaatccc aagagctgac atgcc                                          25

<210> SEQ ID NO 204
<211> LENGTH: 25
<212> TYPE: DNA
<213> ORGANISM: Artificial Sequence
<220> FEATURE:
<223> OTHER INFORMATION: sense primer

<400> SEQUENCE: 204
gtagaatccc aagaagagac atgcc                                          25

<210> SEQ ID NO 205
<211> LENGTH: 25
<212> TYPE: DNA
<213> ORGANISM: Artificial Sequence
<220> FEATURE:
<223> OTHER INFORMATION: sense primer

<400> SEQUENCE: 205
gtagaatccc aagaaacgac atgcc                                          25

<210> SEQ ID NO 206
<211> LENGTH: 25
<212> TYPE: DNA
<213> ORGANISM: Artificial Sequence
<220> FEATURE:
<223> OTHER INFORMATION: sense primer

<400> SEQUENCE: 206
gtagaatccc aagagatgac atgcc                                          25

<210> SEQ ID NO 207
<211> LENGTH: 25
<212> TYPE: DNA
<213> ORGANISM: Artificial Sequence
<220> FEATURE:
<223> OTHER INFORMATION: sense primer

<400> SEQUENCE: 207
gtagaatccc aagagaagac atgcc                                          25

<210> SEQ ID NO 208
<211> LENGTH: 25
<212> TYPE: DNA
<213> ORGANISM: Artificial Sequence
<220> FEATURE:
<223> OTHER INFORMATION: sense primer

<400> SEQUENCE: 208
gtagaatccc aagacaagac atgcc                                          25

<210> SEQ ID NO 209
<211> LENGTH: 25
<212> TYPE: DNA
<213> ORGANISM: Artificial Sequence
<220> FEATURE:
<223> OTHER INFORMATION: sense primer

<400> SEQUENCE: 209
gtagaatccc aagaaaggac atgcc                                          25

<210> SEQ ID NO 210
<211> LENGTH: 25
<212> TYPE: DNA
<213> ORGANISM: Artificial Sequence -continued
<220> FEATURE:
<223> OTHER INFORMATION: sense primer

<400> SEQUENCE: 210
gtagaatccc aagaatggac atgcc                                              25

<210> SEQ ID NO 211
<211> LENGTH: 25
<212> TYPE: DNA
<213> ORGANISM: Artificial Sequence
<220> FEATURE:
<223> OTHER INFORMATION: sense primer

<400> SEQUENCE: 211
gtagaatccc aagatttgac atgcc                                              25

<210> SEQ ID NO 212
<211> LENGTH: 25
<212> TYPE: DNA
<213> ORGANISM: Artificial Sequence
<220> FEATURE:
<223> OTHER INFORMATION: sense primer

<400> SEQUENCE: 212
gtagaatccc aagaccagac atgcc                                              25

<210> SEQ ID NO 213
<211> LENGTH: 25
<212> TYPE: DNA
<213> ORGANISM: Artificial Sequence
<220> FEATURE:
<223> OTHER INFORMATION: sense primer

<400> SEQUENCE: 213
gtagaatccc aagatctgac atgcc                                              25

<210> SEQ ID NO 214
<211> LENGTH: 25
<212> TYPE: DNA
<213> ORGANISM: Artificial Sequence
<220> FEATURE:
<223> OTHER INFORMATION: sense primer

<400> SEQUENCE: 214
gtagaatccc aagaactgac atgcc                                              25

<210> SEQ ID NO 215
<211> LENGTH: 25
<212> TYPE: DNA
<213> ORGANISM: Artificial Sequence
<220> FEATURE:
<223> OTHER INFORMATION: sense primer

<400> SEQUENCE: 215
gtagaatccc aagatgggac atgcc                                              25

<210> SEQ ID NO 216
<211> LENGTH: 25
<212> TYPE: DNA
<213> ORGANISM: Artificial Sequence
<220> FEATURE:
<223> OTHER INFORMATION: sense primer

<400> SEQUENCE: 216
gtagaatccc aagagttgac atgcc                                              25

<210> SEQ ID NO 217
<211> LENGTH: 25
<212> TYPE: DNA
<213> ORGANISM: Artificial Sequence
<220> FEATURE:
<223> OTHER INFORMATION: sense primer

<400> SEQUENCE: 217
gtagaatccc aagatacgac atgcc                                          25

<210> SEQ ID NO 218
<211> LENGTH: 14
<212> TYPE: DNA
<213> ORGANISM: Artificial Sequence
<220> FEATURE:
<223> OTHER INFORMATION: antisense primer

<400> SEQUENCE: 218
tcttgggatt ctac                                                      14

<210> SEQ ID NO 219
<211> LENGTH: 24
<212> TYPE: DNA
<213> ORGANISM: Artificial Sequence
<220> FEATURE:
<223> OTHER INFORMATION: sense primer

<400> SEQUENCE: 219
gaatcccaag acttgacatg ccag                                           24

<210> SEQ ID NO 220
<211> LENGTH: 24
<212> TYPE: DNA
<213> ORGANISM: Artificial Sequence
<220> FEATURE:
<223> OTHER INFORMATION: antisense primer

<400> SEQUENCE: 220
ctggcatgtc aagtcttggg attc                                           24

<210> SEQ ID NO 221
<211> LENGTH: 27
<212> TYPE: DNA
<213> ORGANISM: Artificial Sequence
<220> FEATURE:
<223> OTHER INFORMATION: sense primer

<400> SEQUENCE: 221
agaatcccaa gacacgacat gccagac                                        27

<210> SEQ ID NO 222
<211> LENGTH: 27
<212> TYPE: DNA
<213> ORGANISM: Artificial Sequence
<220> FEATURE:
<223> OTHER INFORMATION: antisense primer

<400> SEQUENCE: 222
gtctggcatg tcgtgtcttg ggattct                                        27

<210> SEQ ID NO 223
<211> LENGTH: 27
<212> TYPE: DNA
<213> ORGANISM: Artificial Sequence
<220> FEATURE:
<223> OTHER INFORMATION: sense primer

```
<400> SEQUENCE: 223
agaatcccaa gaatcgacat gccagac                                              27

<210> SEQ ID NO 224
<211> LENGTH: 27
<212> TYPE: DNA
<213> ORGANISM: Artificial Sequence
<220> FEATURE:
<223> OTHER INFORMATION: antisense primer

<400> SEQUENCE: 224
gtctggcatg tcgattcttg ggattct                                              27

<210> SEQ ID NO 225
<211> LENGTH: 25
<212> TYPE: DNA
<213> ORGANISM: Artificial Sequence
<220> FEATURE:
<223> OTHER INFORMATION: sense primer

<400> SEQUENCE: 225
caagaggtga caacccagac gacag                                                25

<210> SEQ ID NO 226
<211> LENGTH: 25
<212> TYPE: DNA
<213> ORGANISM: Artificial Sequence
<220> FEATURE:
<223> OTHER INFORMATION: sense primer

<400> SEQUENCE: 226
caagaggtga cgacccagac gacag                                                25

<210> SEQ ID NO 227
<211> LENGTH: 25
<212> TYPE: DNA
<213> ORGANISM: Artificial Sequence
<220> FEATURE:
<223> OTHER INFORMATION: sense primer

<400> SEQUENCE: 227
caagaggtga cggtccagac gacag                                                25

<210> SEQ ID NO 228
<211> LENGTH: 25
<212> TYPE: DNA
<213> ORGANISM: Artificial Sequence
<220> FEATURE:
<223> OTHER INFORMATION: sense primer

<400> SEQUENCE: 228
caagaggtga ctggccagac gacag                                                25

<210> SEQ ID NO 229
<211> LENGTH: 25
<212> TYPE: DNA
<213> ORGANISM: Artificial Sequence
<220> FEATURE:
<223> OTHER INFORMATION: sense primer

<400> SEQUENCE: 229
caagaggtga cttcccagac gacag                                                25

<210> SEQ ID NO 230
```

```
<211> LENGTH: 25
<212> TYPE: DNA
<213> ORGANISM: Artificial Sequence
<220> FEATURE:
<223> OTHER INFORMATION: sense primer

<400> SEQUENCE: 230
caagaggtga caaaccagac gacag                                            25

<210> SEQ ID NO 231
<211> LENGTH: 25
<212> TYPE: DNA
<213> ORGANISM: Artificial Sequence
<220> FEATURE:
<223> OTHER INFORMATION: sense primer

<400> SEQUENCE: 231
caagaggtga cctgccagac gacag                                            25

<210> SEQ ID NO 232
<211> LENGTH: 25
<212> TYPE: DNA
<213> ORGANISM: Artificial Sequence
<220> FEATURE:
<223> OTHER INFORMATION: sense primer

<400> SEQUENCE: 232
caagaggtga cgcaccagac gacag                                            25

<210> SEQ ID NO 233
<211> LENGTH: 25
<212> TYPE: DNA
<213> ORGANISM: Artificial Sequence
<220> FEATURE:
<223> OTHER INFORMATION: sense primer

<400> SEQUENCE: 233
caagaggtga cgaaccagac gacag                                            25

<210> SEQ ID NO 234
<211> LENGTH: 18
<212> TYPE: DNA
<213> ORGANISM: Artificial Sequence
<220> FEATURE:
<223> OTHER INFORMATION: sense primer

<400> SEQUENCE: 234
tagaggtgat agaccaga                                                    18

<210> SEQ ID NO 235
<211> LENGTH: 18
<212> TYPE: DNA
<213> ORGANISM: Artificial Sequence
<220> FEATURE:
<223> OTHER INFORMATION: sense primer

<400> SEQUENCE: 235
tagaggtgat tctccaga                                                    18

<210> SEQ ID NO 236
<211> LENGTH: 18
<212> TYPE: DNA
<213> ORGANISM: Artificial Sequence
<220> FEATURE:
<223> OTHER INFORMATION: sense primer

<400> SEQUENCE: 236
```

-continued tagaggtgat gttccaga                                    18

<210> SEQ ID NO 237
<211> LENGTH: 18
<212> TYPE: DNA
<213> ORGANISM: Artificial Sequence
<220> FEATURE:
<223> OTHER INFORMATION: sense primer

<400> SEQUENCE: 237
tagaggtgat actccaga                                    18

<210> SEQ ID NO 238
<211> LENGTH: 18
<212> TYPE: DNA
<213> ORGANISM: Artificial Sequence
<220> FEATURE:
<223> OTHER INFORMATION: sense primer

<400> SEQUENCE: 238
tagaggtgat attccaga                                    18

<210> SEQ ID NO 239
<211> LENGTH: 18
<212> TYPE: DNA
<213> ORGANISM: Artificial Sequence
<220> FEATURE:
<223> OTHER INFORMATION: sense primer

<400> SEQUENCE: 239
tagaggtgat caaccaga                                    18

<210> SEQ ID NO 240
<211> LENGTH: 18
<212> TYPE: DNA
<213> ORGANISM: Artificial Sequence
<220> FEATURE:
<223> OTHER INFORMATION: sense primer

<400> SEQUENCE: 240
tagaggtgat ccaccaga                                    18

<210> SEQ ID NO 241
<211> LENGTH: 18
<212> TYPE: DNA
<213> ORGANISM: Artificial Sequence
<220> FEATURE:
<223> OTHER INFORMATION: sense primer

<400> SEQUENCE: 241
tagaggtgat catccaga                                    18

<210> SEQ ID NO 242
<211> LENGTH: 18
<212> TYPE: DNA
<213> ORGANISM: Artificial Sequence
<220> FEATURE:
<223> OTHER INFORMATION: sense primer

<400> SEQUENCE: 242
tagaggtgat tacccaga                                    18

<210> SEQ ID NO 243
<211> LENGTH: 42
<212> TYPE: DNA

```
<213> ORGANISM: Artificial Sequence
<220> FEATURE:
<223> OTHER INFORMATION: antisense primer

<400> SEQUENCE: 243
ccgcggccgc ggttaaccgt acaaaccgtt tcttggacag tc                          42

<210> SEQ ID NO 244
<211> LENGTH: 30
<212> TYPE: DNA
<213> ORGANISM: Artificial Sequence
<220> FEATURE:
<223> OTHER INFORMATION: sense primer

<400> SEQUENCE: 244
ttcaagaaga agagaactat ctgcagaatc                                        30

<210> SEQ ID NO 245
<211> LENGTH: 23
<212> TYPE: DNA
<213> ORGANISM: Artificial Sequence
<220> FEATURE:
<223> OTHER INFORMATION: antisense primer

<400> SEQUENCE: 245
ctcttcttct tgaacttaca ttg                                               23

<210> SEQ ID NO 246
<211> LENGTH: 27
<212> TYPE: DNA
<213> ORGANISM: Artificial Sequence
<220> FEATURE:
<223> OTHER INFORMATION: sense primer

<400> SEQUENCE: 246
tctagagctg gtaagatctg tagacgc                                           27

<210> SEQ ID NO 247
<211> LENGTH: 24
<212> TYPE: DNA
<213> ORGANISM: Artificial Sequence
<220> FEATURE:
<223> OTHER INFORMATION: antisense primer

<400> SEQUENCE: 247
accagctcta gagaatctac attg                                              24

<210> SEQ ID NO 248
<211> LENGTH: 15
<212> TYPE: DNA
<213> ORGANISM: Artificial Sequence
<220> FEATURE:
<223> OTHER INFORMATION: sense primer

<400> SEQUENCE: 248
gctaagaaga gaact                                                        15

<210> SEQ ID NO 249
<211> LENGTH: 27
<212> TYPE: DNA
<213> ORGANISM: Artificial Sequence
<220> FEATURE:
<223> OTHER INFORMATION: antisense primer

<400> SEQUENCE: 249
agttctcttc ttagcgaact tacattg                                           27
```

```
<210> SEQ ID NO 250
<211> LENGTH: 15
<212> TYPE: DNA
<213> ORGANISM: Artificial Sequence
<220> FEATURE:
<223> OTHER INFORMATION: sense primer

<400> SEQUENCE: 250
gctaagagaa ctatc                                                     15

<210> SEQ ID NO 251
<211> LENGTH: 27
<212> TYPE: DNA
<213> ORGANISM: Artificial Sequence
<220> FEATURE:
<223> OTHER INFORMATION: antisense primer

<400> SEQUENCE: 251
gatagttctc ttagccttga acttaca                                        27

<210> SEQ ID NO 252
<211> LENGTH: 15
<212> TYPE: DNA
<213> ORGANISM: Artificial Sequence
<220> FEATURE:
<223> OTHER INFORMATION: sense primer

<400> SEQUENCE: 252
gctactatct gcaga                                                     15

<210> SEQ ID NO 253
<211> LENGTH: 27
<212> TYPE: DNA
<213> ORGANISM: Artificial Sequence
<220> FEATURE:
<223> OTHER INFORMATION: antisense primer

<400> SEQUENCE: 253
tctgcagata gtagccttct tcttgaa                                        27

<210> SEQ ID NO 254
<211> LENGTH: 15
<212> TYPE: DNA
<213> ORGANISM: Artificial Sequence
<220> FEATURE:
<223> OTHER INFORMATION: sense primer

<400> SEQUENCE: 254
gctatctgca gaatc                                                     15

<210> SEQ ID NO 255
<211> LENGTH: 27
<212> TYPE: DNA
<213> ORGANISM: Artificial Sequence
<220> FEATURE:
<223> OTHER INFORMATION: antisense primer

<400> SEQUENCE: 255
gattctgcag atagctctct tcttctt                                        27

<210> SEQ ID NO 256
<211> LENGTH: 15
<212> TYPE: DNA
<213> ORGANISM: Artificial Sequence
<220> FEATURE:
```

<223> OTHER INFORMATION: sense primer

<400> SEQUENCE: 256
ggtactatct gcaga                                                    15

<210> SEQ ID NO 257
<211> LENGTH: 30
<212> TYPE: DNA
<213> ORGANISM: Artificial Sequence
<220> FEATURE:
<223> OTHER INFORMATION: antisense primer

<400> SEQUENCE: 257
gcagatagta ccagccttag agaacttaca                                    30

<210> SEQ ID NO 258
<211> LENGTH: 33
<212> TYPE: DNA
<213> ORGANISM: Artificial Sequence
<220> FEATURE:
<223> OTHER INFORMATION: antisense primer

<400> SEQUENCE: 258
gcagatagta ccttcttcga tgaacttaca ttg                                33

<210> SEQ ID NO 259
<211> LENGTH: 33
<212> TYPE: DNA
<213> ORGANISM: Artificial Sequence
<220> FEATURE:
<223> OTHER INFORMATION: antisense primer

<400> SEQUENCE: 259
gcagatagta ccttccttca agaacttaca ttg                                33

<210> SEQ ID NO 260
<211> LENGTH: 33
<212> TYPE: DNA
<213> ORGANISM: Artificial Sequence
<220> FEATURE:
<223> OTHER INFORMATION: antisense primer

<400> SEQUENCE: 260
gcagatagta cccttcttca tgaacttaca ttg                                33

<210> SEQ ID NO 261
<211> LENGTH: 24
<212> TYPE: DNA
<213> ORGANISM: Artificial Sequence
<220> FEATURE:
<223> OTHER INFORMATION: sense primer

<400> SEQUENCE: 261
aagttcaagg ctaagagagc tatc                                          24

<210> SEQ ID NO 262
<211> LENGTH: 15
<212> TYPE: DNA
<213> ORGANISM: Artificial Sequence
<220> FEATURE:
<223> OTHER INFORMATION: antisense primer

<400> SEQUENCE: 262
agccttgaac ttaca                                                    15

```
<210> SEQ ID NO 263
<211> LENGTH: 24
<212> TYPE: DNA
<213> ORGANISM: Artificial Sequence
<220> FEATURE:
<223> OTHER INFORMATION: sense primer

<400> SEQUENCE: 263
ggtgctggta agatctgcag aatc                                              24

<210> SEQ ID NO 264
<211> LENGTH: 24
<212> TYPE: DNA
<213> ORGANISM: Artificial Sequence
<220> FEATURE:
<223> OTHER INFORMATION: antisense primer

<400> SEQUENCE: 264
cttaccagca cccttgaact taca                                              24

<210> SEQ ID NO 265
<211> LENGTH: 15
<212> TYPE: DNA
<213> ORGANISM: Artificial Sequence
<220> FEATURE:
<223> OTHER INFORMATION: sense primer

<400> SEQUENCE: 265
gctatcccaa gaggt                                                        15

<210> SEQ ID NO 266
<211> LENGTH: 17
<212> TYPE: DNA
<213> ORGANISM: Artificial Sequence
<220> FEATURE:
<223> OTHER INFORMATION: antisense primer

<400> SEQUENCE: 266
tcttgggatg ccagatc                                                      17

<210> SEQ ID NO 267
<211> LENGTH: 20
<212> TYPE: DNA
<213> ORGANISM: Artificial Sequence
<220> FEATURE:
<223> OTHER INFORMATION: sense primer

<400> SEQUENCE: 267
actatctgcg ctatcgcaag                                                   20

<210> SEQ ID NO 268
<211> LENGTH: 16
<212> TYPE: DNA
<213> ORGANISM: Artificial Sequence
<220> FEATURE:
<223> OTHER INFORMATION: antisense primer

<400> SEQUENCE: 268
agcgcagata gttctc                                                       16

<210> SEQ ID NO 269
<211> LENGTH: 23
<212> TYPE: DNA
<213> ORGANISM: Artificial Sequence
<220> FEATURE:
<223> OTHER INFORMATION: sense primer
```

<400> SEQUENCE: 269
actatctgcg ctagagcaag agg                                            23

<210> SEQ ID NO 270
<211> LENGTH: 16
<212> TYPE: DNA
<213> ORGANISM: Artificial Sequence
<220> FEATURE:
<223> OTHER INFORMATION: antisense primer

<400> SEQUENCE: 270
agcgcagata gttctc                                                    16

<210> SEQ ID NO 271
<211> LENGTH: 20
<212> TYPE: DNA
<213> ORGANISM: Artificial Sequence
<220> FEATURE:
<223> OTHER INFORMATION: sense primer

<400> SEQUENCE: 271
gacgaaccag acgacagatg                                                20

<210> SEQ ID NO 272
<211> LENGTH: 18
<212> TYPE: DNA
<213> ORGANISM: Artificial Sequence
<220> FEATURE:
<223> OTHER INFORMATION: antisense primer

<400> SEQUENCE: 272
gtctggttcg tcacctct                                                  18

<210> SEQ ID NO 273
<211> LENGTH: 18
<212> TYPE: DNA
<213> ORGANISM: Artificial Sequence
<220> FEATURE:
<223> OTHER INFORMATION: antisense primer

<400> SEQUENCE: 273
gtctggttcg tcccatct                                                  18

<210> SEQ ID NO 274
<211> LENGTH: 18
<212> TYPE: DNA
<213> ORGANISM: Artificial Sequence
<220> FEATURE:
<223> OTHER INFORMATION: antisense primer

<400> SEQUENCE: 274
gtctggttcg tcctttct                                                  18

<210> SEQ ID NO 275
<211> LENGTH: 20
<212> TYPE: DNA
<213> ORGANISM: Artificial Sequence
<220> FEATURE:
<223> OTHER INFORMATION: sense primer

<400> SEQUENCE: 275
gactctccag acgacagatg                                                20

<210> SEQ ID NO 276
<211> LENGTH: 18

```
<212> TYPE: DNA
<213> ORGANISM: Artificial Sequence
<220> FEATURE:
<223> OTHER INFORMATION: antisense primer

<400> SEQUENCE: 276
gtctggagag tcttgtct                                                   18

<210> SEQ ID NO 277
<211> LENGTH: 18
<212> TYPE: DNA
<213> ORGANISM: Artificial Sequence
<220> FEATURE:
<223> OTHER INFORMATION: sense primer

<400> SEQUENCE: 277
atcaagcaag gtgacatg                                                   18

<210> SEQ ID NO 278
<211> LENGTH: 18
<212> TYPE: DNA
<213> ORGANISM: Artificial Sequence
<220> FEATURE:
<223> OTHER INFORMATION: antisense primer

<400> SEQUENCE: 278
gtcaccttgc ttgattct                                                   18

<210> SEQ ID NO 279
<211> LENGTH: 17
<212> TYPE: DNA
<213> ORGANISM: Artificial Sequence
<220> FEATURE:
<223> OTHER INFORMATION: sense primer

<400> SEQUENCE: 279
gatccagacg acagatg                                                    17

<210> SEQ ID NO 280
<211> LENGTH: 32
<212> TYPE: DNA
<213> ORGANISM: Artificial Sequence
<220> FEATURE:
<223> OTHER INFORMATION: antisense primer

<400> SEQUENCE: 280
gtcgtctgga tcatccaatc ttgcgcgtct ac                                   32

<210> SEQ ID NO 281
<211> LENGTH: 32
<212> TYPE: DNA
<213> ORGANISM: Artificial Sequence
<220> FEATURE:
<223> OTHER INFORMATION: antisense primer

<400> SEQUENCE: 281
gtcgtctgga tcatccattc ttgcgcgtct ac                                   32

<210> SEQ ID NO 282
<211> LENGTH: 32
<212> TYPE: DNA
<213> ORGANISM: Artificial Sequence
<220> FEATURE:
<223> OTHER INFORMATION: antisense primer

<400> SEQUENCE: 282
```
gtcgtctgga tcatctggtc ttgcgcgtct ac                                32

<210> SEQ ID NO 283
<211> LENGTH: 29
<212> TYPE: DNA
<213> ORGANISM: Artificial Sequence
<220> FEATURE:
<223> OTHER INFORMATION: antisense primer

<400> SEQUENCE: 283
acatctgtcg tctggcatat ccaatcttg                                    29

<210> SEQ ID NO 284
<211> LENGTH: 29
<212> TYPE: DNA
<213> ORGANISM: Artificial Sequence
<220> FEATURE:
<223> OTHER INFORMATION: antisense primer

<400> SEQUENCE: 284
acatctgtcg tctgggttat ccaatcttg                                    29

<210> SEQ ID NO 285
<211> LENGTH: 26
<212> TYPE: DNA
<213> ORGANISM: Artificial Sequence
<220> FEATURE:
<223> OTHER INFORMATION: antisense primer

<400> SEQUENCE: 285
acatctgtcg tcaacatcat ccaatc                                       26

<210> SEQ ID NO 286
<211> LENGTH: 14
<212> TYPE: DNA
<213> ORGANISM: Artificial Sequence
<220> FEATURE:
<223> OTHER INFORMATION: sense primer

<400> SEQUENCE: 286
gacgacagat gtac                                                    14

<210> SEQ ID NO 287
<211> LENGTH: 19
<212> TYPE: DNA
<213> ORGANISM: Artificial Sequence
<220> FEATURE:
<223> OTHER INFORMATION: sense primer

<400> SEQUENCE: 287
ctatctgtag aatcgcaag                                               19

<210> SEQ ID NO 288
<211> LENGTH: 14
<212> TYPE: DNA
<213> ORGANISM: Artificial Sequence
<220> FEATURE:
<223> OTHER INFORMATION: antisense primer

<400> SEQUENCE: 288
gattctacag atag                                                    14

<210> SEQ ID NO 289
<211> LENGTH: 23
<212> TYPE: DNA
<213> ORGANISM: Artificial Sequence

```
<220> FEATURE:
<223> OTHER INFORMATION: sense primer

<400> SEQUENCE: 289
aagatctgta gaagaccaag agg                                              23

<210> SEQ ID NO 290
<211> LENGTH: 23
<212> TYPE: DNA
<213> ORGANISM: Artificial Sequence
<220> FEATURE:
<223> OTHER INFORMATION: sense primer

<400> SEQUENCE: 290
aagatctgta gagctccaag agg                                              23

<210> SEQ ID NO 291
<211> LENGTH: 23
<212> TYPE: DNA
<213> ORGANISM: Artificial Sequence
<220> FEATURE:
<223> OTHER INFORMATION: sense primer

<400> SEQUENCE: 291
aagatctgta gagttccaag agg                                              23

<210> SEQ ID NO 292
<211> LENGTH: 23
<212> TYPE: DNA
<213> ORGANISM: Artificial Sequence
<220> FEATURE:
<223> OTHER INFORMATION: sense primer

<400> SEQUENCE: 292
aagatctgta gaatgccaag agg                                              23

<210> SEQ ID NO 293
<211> LENGTH: 23
<212> TYPE: DNA
<213> ORGANISM: Artificial Sequence
<220> FEATURE:
<223> OTHER INFORMATION: sense primer

<400> SEQUENCE: 293
aagatctgta gaccaccaag agg                                              23

<210> SEQ ID NO 294
<211> LENGTH: 23
<212> TYPE: DNA
<213> ORGANISM: Artificial Sequence
<220> FEATURE:
<223> OTHER INFORMATION: sense primer

<400> SEQUENCE: 294
aagatctgta gagaaccaag agg                                              23

<210> SEQ ID NO 295
<211> LENGTH: 23
<212> TYPE: DNA
<213> ORGANISM: Artificial Sequence
<220> FEATURE:
<223> OTHER INFORMATION: sense primer

<400> SEQUENCE: 295
aagatctgta gacaaccaag agg                                              23
```

```
<210> SEQ ID NO 296
<211> LENGTH: 23
<212> TYPE: DNA
<213> ORGANISM: Artificial Sequence
<220> FEATURE:
<223> OTHER INFORMATION: sense primer

<400> SEQUENCE: 296
aagatctgta gatttccaag agg                                          23

<210> SEQ ID NO 297
<211> LENGTH: 14
<212> TYPE: DNA
<213> ORGANISM: Artificial Sequence
<220> FEATURE:
<223> OTHER INFORMATION: antisense primer

<400> SEQUENCE: 297
tctacagatc ttac                                                    14

<210> SEQ ID NO 298
<211> LENGTH: 26
<212> TYPE: DNA
<213> ORGANISM: Artificial Sequence
<220> FEATURE:
<223> OTHER INFORMATION: sense primer

<400> SEQUENCE: 298
ggtaagatct gtaagagacc aagagg                                       26

<210> SEQ ID NO 299
<211> LENGTH: 26
<212> TYPE: DNA
<213> ORGANISM: Artificial Sequence
<220> FEATURE:
<223> OTHER INFORMATION: sense primer

<400> SEQUENCE: 299
ggtaagatct gtaagattcc aagagg                                       26

<210> SEQ ID NO 300
<211> LENGTH: 26
<212> TYPE: DNA
<213> ORGANISM: Artificial Sequence
<220> FEATURE:
<223> OTHER INFORMATION: sense primer

<400> SEQUENCE: 300
ggtaagatct gtaagatgcc aagagg                                       26

<210> SEQ ID NO 301
<211> LENGTH: 26
<212> TYPE: DNA
<213> ORGANISM: Artificial Sequence
<220> FEATURE:
<223> OTHER INFORMATION: sense primer

<400> SEQUENCE: 301
ggtaagatct gtaagaagcc aagagg                                       26

<210> SEQ ID NO 302
<211> LENGTH: 26
<212> TYPE: DNA
<213> ORGANISM: Artificial Sequence
<220> FEATURE:
<223> OTHER INFORMATION: sense primer
```

<400> SEQUENCE: 302
ggtaagatct gtgaaatccc aagagg                                           26

<210> SEQ ID NO 303
<211> LENGTH: 26
<212> TYPE: DNA
<213> ORGANISM: Artificial Sequence
<220> FEATURE:
<223> OTHER INFORMATION: sense primer

<400> SEQUENCE: 303
ggtaagatct gtcaaatccc aagagg                                           26

<210> SEQ ID NO 304
<211> LENGTH: 26
<212> TYPE: DNA
<213> ORGANISM: Artificial Sequence
<220> FEATURE:
<223> OTHER INFORMATION: sense primer

<400> SEQUENCE: 304
ggtaagatct gttttatccc aagagg                                           26

<210> SEQ ID NO 305
<211> LENGTH: 14
<212> TYPE: DNA
<213> ORGANISM: Artificial Sequence
<220> FEATURE:
<223> OTHER INFORMATION: antisense primer

<400> SEQUENCE: 305
acagatctta ccag                                                        14

<210> SEQ ID NO 306
<211> LENGTH: 7
<212> TYPE: PRT
<213> ORGANISM: Artificial Sequence
<220> FEATURE:
<223> OTHER INFORMATION: mutant linker

<400> SEQUENCE: 306

Lys Lys Lys Arg Thr Ile Cys
1               5

<210> SEQ ID NO 307
<211> LENGTH: 7
<212> TYPE: PRT
<213> ORGANISM: Artificial Sequence
<220> FEATURE:
<223> OTHER INFORMATION: mutant linker

<400> SEQUENCE: 307

Met Lys Lys Gly Thr Ile Cys
1               5

<210> SEQ ID NO 308
<211> LENGTH: 7
<212> TYPE: PRT
<213> ORGANISM: Artificial Sequence
<220> FEATURE:
<223> OTHER INFORMATION: mutant linker

<400> SEQUENCE: 308

Ile Glu Glu Gly Thr Ile Cys
1               5

```
<210> SEQ ID NO 309
<211> LENGTH: 7
<212> TYPE: PRT
<213> ORGANISM: Artificial Sequence
<220> FEATURE:
<223> OTHER INFORMATION: mutant linker

<400> SEQUENCE: 309

Lys Gly Ala Gly Lys Ile Cys
1               5

<210> SEQ ID NO 310
<211> LENGTH: 7
<212> TYPE: PRT
<213> ORGANISM: Artificial Sequence
<220> FEATURE:
<223> OTHER INFORMATION: mutant linker

<400> SEQUENCE: 310

Leu Lys Glu Gly Thr Ile Cys
1               5

<210> SEQ ID NO 311
<211> LENGTH: 7
<212> TYPE: PRT
<213> ORGANISM: Artificial Sequence
<220> FEATURE:
<223> OTHER INFORMATION: mutant linker

<400> SEQUENCE: 311

Ala Lys Lys Arg Thr Ile Cys
1               5

<210> SEQ ID NO 312
<211> LENGTH: 7
<212> TYPE: PRT
<213> ORGANISM: Artificial Sequence
<220> FEATURE:
<223> OTHER INFORMATION: mutant linker

<400> SEQUENCE: 312

Lys Ala Lys Arg Thr Ile Cys
1               5

<210> SEQ ID NO 313
<211> LENGTH: 7
<212> TYPE: PRT
<213> ORGANISM: Artificial Sequence
<220> FEATURE:
<223> OTHER INFORMATION: mutant linker

<400> SEQUENCE: 313

Lys Lys Ala Arg Thr Ile Cys
1               5

<210> SEQ ID NO 314
<211> LENGTH: 7
<212> TYPE: PRT
<213> ORGANISM: Artificial Sequence
<220> FEATURE:
<223> OTHER INFORMATION: mutant linker

<400> SEQUENCE: 314

Lys Lys Lys Ala Thr Ile Cys
1               5
```

```
<210> SEQ ID NO 315
<211> LENGTH: 7
<212> TYPE: PRT
<213> ORGANISM: Artificial Sequence
<220> FEATURE:
<223> OTHER INFORMATION: mutant linker

<400> SEQUENCE: 315

Lys Lys Lys Arg Ala Ile Cys
1               5

<210> SEQ ID NO 316
<211> LENGTH: 7
<212> TYPE: PRT
<213> ORGANISM: Artificial Sequence
<220> FEATURE:
<223> OTHER INFORMATION: mutant linker

<400> SEQUENCE: 316

Lys Ala Lys Arg Ala Ile Cys
1               5

<210> SEQ ID NO 317
<211> LENGTH: 7
<212> TYPE: PRT
<213> ORGANISM: Artificial Sequence
<220> FEATURE:
<223> OTHER INFORMATION: mutant linker

<400> SEQUENCE: 317

Ser Lys Ala Gly Thr Ile Cys
1               5

<210> SEQ ID NO 318
<211> LENGTH: 7
<212> TYPE: PRT
<213> ORGANISM: Artificial Sequence
<220> FEATURE:
<223> OTHER INFORMATION: mutant linker

<400> SEQUENCE: 318

Lys Lys Lys Arg Thr Ile Cys
1               5

<210> SEQ ID NO 319
<211> LENGTH: 6
<212> TYPE: PRT
<213> ORGANISM: Artificial Sequence
<220> FEATURE:
<223> OTHER INFORMATION: mutant C-terminus

<400> SEQUENCE: 319

Pro Arg Trp Asn Asp Leu
1               5

<210> SEQ ID NO 320
<211> LENGTH: 7
<212> TYPE: PRT
<213> ORGANISM: Artificial Sequence
<220> FEATURE:
<223> OTHER INFORMATION: mutant C-terminus

<400> SEQUENCE: 320

Pro Arg Asn Pro Trp Asn Gly
1               5
```

```
<210> SEQ ID NO 321
<211> LENGTH: 6
<212> TYPE: PRT
<213> ORGANISM: Artificial Sequence
<220> FEATURE:
<223> OTHER INFORMATION: mutant C-terminus

<400> SEQUENCE: 321

Pro Arg Asn Arg Phe His
1               5

<210> SEQ ID NO 322
<211> LENGTH: 7
<212> TYPE: PRT
<213> ORGANISM: Artificial Sequence
<220> FEATURE:
<223> OTHER INFORMATION: mutant C-terminus

<400> SEQUENCE: 322

Pro Arg Asn Arg Phe His Ala
1               5

<210> SEQ ID NO 323
<211> LENGTH: 7
<212> TYPE: PRT
<213> ORGANISM: Artificial Sequence
<220> FEATURE:
<223> OTHER INFORMATION: mutant C-terminus

<400> SEQUENCE: 323

Pro Arg Asn Gly Leu Tyr Gly
1               5

<210> SEQ ID NO 324
<211> LENGTH: 5
<212> TYPE: PRT
<213> ORGANISM: Artificial Sequence
<220> FEATURE:
<223> OTHER INFORMATION: mutant C-terminus

<400> SEQUENCE: 324

Pro Gly Leu Tyr Gly
1               5

<210> SEQ ID NO 325
<211> LENGTH: 4
<212> TYPE: PRT
<213> ORGANISM: Artificial Sequence
<220> FEATURE:
<223> OTHER INFORMATION: mutant C-terminus

<400> SEQUENCE: 325

Pro Gly Leu Tyr
1

<210> SEQ ID NO 326
<211> LENGTH: 5
<212> TYPE: PRT
<213> ORGANISM: Artificial Sequence
<220> FEATURE:
<223> OTHER INFORMATION: mutant C-terminus

<400> SEQUENCE: 326

Pro Asp Leu Tyr Gly
1               5

<210> SEQ ID NO 327
```

```
<211> LENGTH: 5
<212> TYPE: PRT
<213> ORGANISM: Artificial Sequence
<220> FEATURE:
<223> OTHER INFORMATION: mutant C-terminus

<400> SEQUENCE: 327

Pro Pro Leu Tyr Gly
1               5

<210> SEQ ID NO 328
<211> LENGTH: 5
<212> TYPE: PRT
<213> ORGANISM: Artificial Sequence
<220> FEATURE:
<223> OTHER INFORMATION: mutant C-terminus

<400> SEQUENCE: 328

Pro Arg Leu Tyr Gly
1               5

<210> SEQ ID NO 329
<211> LENGTH: 8
<212> TYPE: PRT
<213> ORGANISM: Artificial Sequence
<220> FEATURE:
<223> OTHER INFORMATION: mutant RGD

<400> SEQUENCE: 329

Arg Ile Ala Arg Gly Asp Asn Pro
1               5

<210> SEQ ID NO 330
<211> LENGTH: 8
<212> TYPE: PRT
<213> ORGANISM: Artificial Sequence
<220> FEATURE:
<223> OTHER INFORMATION: mutant RGD

<400> SEQUENCE: 330

Arg Arg Ala Arg Gly Asp Asn Pro
1               5

<210> SEQ ID NO 331
<211> LENGTH: 8
<212> TYPE: PRT
<213> ORGANISM: Artificial Sequence
<220> FEATURE:
<223> OTHER INFORMATION: mutant RGD

<400> SEQUENCE: 331

Ala Arg Gly Arg Gly Asp Asn Pro
1               5

<210> SEQ ID NO 332
<211> LENGTH: 7
<212> TYPE: PRT
<213> ORGANISM: Calloselasma rhodostoma

<400> SEQUENCE: 332

Ser Arg Ala Gly Lys Ile Cys
1               5

<210> SEQ ID NO 333
<211> LENGTH: 8
<212> TYPE: PRT
<213> ORGANISM: Calloselasma rhodostoma
```

-continued

<400> SEQUENCE: 333

Arg Ile Pro Arg Gly Asp Met Pro
1               5

<210> SEQ ID NO 334
<211> LENGTH: 4
<212> TYPE: PRT
<213> ORGANISM: Calloselasma rhodostoma

<400> SEQUENCE: 334

Pro Arg Tyr His
1

<210> SEQ ID NO 335
<211> LENGTH: 6
<212> TYPE: PRT
<213> ORGANISM: Artificial Sequence
<220> FEATURE:
<223> OTHER INFORMATION: synthetic

<400> SEQUENCE: 335

Ala Arg Gly Asp Met Pro
1               5

<210> SEQ ID NO 336
<211> LENGTH: 68
<212> TYPE: PRT
<213> ORGANISM: Artificial Sequence
<220> FEATURE:
<223> OTHER INFORMATION: Rhodostomin Variant
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (66)..(68)
<223> OTHER INFORMATION: Xaa can be any naturally occurring amino acid

<400> SEQUENCE: 336

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30

Cys Glu Gln Cys Lys Phe Xaa Xaa Xaa Xaa Ile Cys Xaa Xaa Xaa
            35                  40                  45

Arg Xaa Asp Xaa Xaa Asp Asp Arg Cys Thr Gly Gln Ser Ala Asp Cys
    50                  55                  60

Pro Xaa Xaa Xaa
65

<210> SEQ ID NO 337
<211> LENGTH: 5
<212> TYPE: PRT

```
<213> ORGANISM: Artificial Sequence
<220> FEATURE:
<223> OTHER INFORMATION: mutant C-terminus

<400> SEQUENCE: 337

Pro Glu Leu Tyr Gly
1               5

<210> SEQ ID NO 338
<211> LENGTH: 68
<212> TYPE: PRT
<213> ORGANISM: Artificial Sequence
<220> FEATURE:
<223> OTHER INFORMATION: ARGDXX peptide, mutation at X

<400> SEQUENCE: 338

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Asp Leu Asp Asp Arg Cys Thr Gly Gln Ser Ala Asp Cys
    50                  55                  60

Pro Arg Tyr His
65

<210> SEQ ID NO 339
<211> LENGTH: 69
<212> TYPE: PRT
<213> ORGANISM: Artificial Sequence
<220> FEATURE:
<223> OTHER INFORMATION: Rhodostomin mutant peptide

<400> SEQUENCE: 339

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asp Leu Asp Asp Arg Cys Thr Gly Gln Ser Ala Asp Cys
    50                  55                  60

Pro Gly Leu Tyr Gly
65

<210> SEQ ID NO 340
<211> LENGTH: 6
<212> TYPE: PRT
<213> ORGANISM: Artificial Sequence
<220> FEATURE:
<223> OTHER INFORMATION: consensus sequence of mutant RGD loop, mutation
      at X
<220> FEATURE:
<221> NAME/KEY: misc_feature
<222> LOCATION: (5)..(6)
<223> OTHER INFORMATION: Xaa can be any naturally occurring amino acid

<400> SEQUENCE: 340

Ala Arg Gly Asp Xaa Xaa
1               5

<210> SEQ ID NO 341
```

```
<211> LENGTH: 4
<212> TYPE: PRT
<213> ORGANISM: Artificial Sequence
<220> FEATURE:
<223> OTHER INFORMATION: consensus sequence of mutant RGD loop, mutation
      at X
<220> FEATURE:
<221> NAME/KEY: misc_feature
<222> LOCATION: (1)..(1)
<223> OTHER INFORMATION: Xaa can be any naturally occurring amino acid

<400> SEQUENCE: 341

Xaa Arg Gly Asp
1

<210> SEQ ID NO 342
<211> LENGTH: 6
<212> TYPE: PRT
<213> ORGANISM: Artificial Sequence
<220> FEATURE:
<223> OTHER INFORMATION: consensus sequence mutant RGD loop, mutation at
      X
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 342

Xaa Arg Gly Asp Xaa Pro
1               5

<210> SEQ ID NO 343
<211> LENGTH: 6
<212> TYPE: PRT
<213> ORGANISM: Artificial Sequence
<220> FEATURE:
<223> OTHER INFORMATION: consensus sequence of mutant RGD loop, mutation
      at X
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 343

Xaa Arg Gly Asp Met Xaa
1               5

<210> SEQ ID NO 344
<211> LENGTH: 6
<212> TYPE: PRT
<213> ORGANISM: Artificial Sequence
<220> FEATURE:
<223> OTHER INFORMATION: consensus sequence of mutant RGD loop, mutation
      at X
<220> FEATURE:
<221> NAME/KEY: misc_feature
<222> LOCATION: (1)..(2)
<223> OTHER INFORMATION: Xaa can be any naturally occurring amino acid

<400> SEQUENCE: 344

Xaa Xaa Pro Arg Gly Asp
1               5
```

```
<210> SEQ ID NO 345
<211> LENGTH: 6
<212> TYPE: PRT
<213> ORGANISM: Artificial Sequence
<220> FEATURE:
<223> OTHER INFORMATION: consensus sequence of mutant RGD loop, mutation
      at X
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 345

Xaa Arg Xaa Asp Xaa Pro
1               5

<210> SEQ ID NO 346
<211> LENGTH: 7
<212> TYPE: PRT
<213> ORGANISM: Artificial Sequence
<220> FEATURE:
<223> OTHER INFORMATION: consensus sequence of mutant C-terminus,
      mutation at X
<220> FEATURE:
<221> NAME/KEY: misc_feature
<222> LOCATION: (3)..(7)
<223> OTHER INFORMATION: Xa

```
                1               5                   10                  15
Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Ala
        35                  40                  45

Arg Gly Asp Met Pro Asp Asp Arg Cys Thr Gly Gln Ser Ala Asp Cys
    50                  55                  60

Pro Arg Asn Gly Leu
65

<210> SEQ ID NO 349
<211> LENGTH: 71
<212> TYPE: PRT
<213> ORGANISM: Artificial Sequence
<220> FEATURE:
<223> OTHER INFORMATION: XXXXX-ICXXXRGDXP-XXXXX peptide, mutation at X

<400> SEQUENCE: 349

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Met Lys Lys Gly Thr Ile Cys Arg Ile Ala
        35                  40                  45

Arg Gly Asp Asn Pro Asp Asp Arg Cys Thr Gly Gln Ser Ala Asp Cys
    50                  55                  60

Pro Arg Asn Gly Leu Tyr Gly
65                  70

<210> SEQ ID NO 350
<211> LENGTH: 17
<212> TYPE: PRT
<213> ORGANISM: Artificial Sequence
<220> FEATURE:
<223> OTHER INFORMATION: AR-NP protein

<400> SEQUENCE: 350

Lys Lys Ala Arg Thr Ile Cys Arg Ile Ala Arg Gly Arg Gly Asp Asn
1               5                   10                  15

Pro

<210> SEQ ID NO 351
<211> LENGTH: 6
<212> TYPE: PRT
<213> ORGANISM: Artificial Sequence
<220> FEATURE:
<223> OTHER INFORMATION: ARLDDL protein

<400> SEQUENCE: 351

Ala Arg Leu Asp Asp Leu
1               5

<210> SEQ ID NO 352
<211> LENGTH: 5
<212> TYPE: PRT
<213> ORGANISM: Artificial Sequence
<220> FEATURE:
<223> OTHER INFORMATION: mutant C terminus

<400> SEQUENCE: 352

Pro Tyr Leu Tyr Gly
1

```
<210> SEQ ID NO 353
<211> LENGTH: 8
<212> TYPE: PRT
<213> ORGANISM: Artificial Sequence
<220> FEATURE:
<223> OTHER INFORMATION: mutant RGD loop sequence

<400> SEQUENCE: 353

Ala Arg Gly Arg Gly Asp Asp Leu
1               5

<210> SEQ ID NO 354
<211> LENGTH: 8
<212> TYPE: PRT
<213> ORGANISM: Artificial Sequence
<220> FEATURE:
<223> OTHER INFORMATION: mutant RGD loop sequence

<400> SEQUENCE: 354

Ala Arg Ala Arg Gly Asp Asn Pro
1               5
```